US011339360B2

(12) United States Patent
He et al.

(10) Patent No.: US 11,339,360 B2
(45) Date of Patent: May 24, 2022

(54) CULTURE SYSTEMS AND METHODS OF USING SAME

(71) Applicant: AUBURN UNIVERSITY, Auburn, AL (US)

(72) Inventors: Qinghua He, Auburn, AL (US); Jin Wang, Auburn, AL (US); Matthew V. Hilliard, Pelham, GA (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 16/934,766

(22) Filed: Jul. 21, 2020

(65) Prior Publication Data

US 2021/0024861 A1 Jan. 28, 2021

Related U.S. Application Data

(60) Provisional application No. 63/047,114, filed on Jul. 1, 2020, provisional application No. 62/877,126, filed on Jul. 22, 2019.

(51) Int. Cl.
*B01D 53/62* (2006.01)
*B01D 53/72* (2006.01)
(Continued)

(52) U.S. Cl.
CPC ............. *C12M 21/02* (2013.01); *B01D 53/62* (2013.01); *B01D 53/72* (2013.01); *B01D 53/85* (2013.01);
(Continued)

(58) Field of Classification Search
CPC ...... C12M 21/02; C12M 23/18; C12M 23/36; C12M 23/58; C12M 27/00; C12M 29/00; C12M 41/00; C12M 43/00; C12M 47/18; C12M 21/04; C12M 33/20; B01D 53/62; B01D 53/72; B01D 53/85; B01D 2251/95; B01D 2257/504; B01D 2257/7022; B01D 2258/05; C02F 3/2806; C02F 3/2813;
(Continued)

(56) References Cited

U.S. PATENT DOCUMENTS

| 4,211,647 A | * | 7/1980 | Friedman | ................ | C02F 3/082 |
| | | | | | 210/603 |
| 4,324,068 A | * | 4/1982 | Anthony | ................ | C12M 25/06 |
| | | | | | 47/1.4 |

(Continued)

FOREIGN PATENT DOCUMENTS

CN 101279324 10/2008

OTHER PUBLICATIONS

Machine-generated English Translation of CN 101279324, dated Sep. 7, 2021.*

(Continued)

*Primary Examiner* — Fred Prince
(74) *Attorney, Agent, or Firm* — Christopher M. Scherer; Daniel A. Blasiole; DeWitt LLP

(57) ABSTRACT

Culture systems and methods of using same. The systems include a housing defining an inner space. The inner space includes a headspace and at least a portion of a reservoir. A surface for immobilizing cells is moveable between the headspace and the reservoir. The systems can be used for coculturing methanotrophs and phototrophs for processing biogas and wastewater, particularly from anaerobic digesters.

27 Claims, 18 Drawing Sheets

(51) Int. Cl.
| | |
|---|---|
| B01D 53/85 | (2006.01) |
| C02F 3/28 | (2006.01) |
| C02F 3/32 | (2006.01) |
| C02F 3/34 | (2006.01) |
| C12M 1/00 | (2006.01) |
| C12M 1/107 | (2006.01) |
| C12M 1/02 | (2006.01) |
| C12M 1/34 | (2006.01) |
| C02F 101/10 | (2006.01) |
| C02F 101/16 | (2006.01) |

(52) U.S. Cl.
CPC .......... *C02F 3/2806* (2013.01); *C02F 3/2813* (2013.01); *C02F 3/2866* (2013.01); *C02F 3/325* (2013.01); *C02F 3/341* (2013.01); *C12M 23/18* (2013.01); *C12M 23/36* (2013.01); *C12M 23/58* (2013.01); *C12M 27/00* (2013.01); *C12M 29/00* (2013.01); *C12M 41/00* (2013.01); *C12M 43/00* (2013.01); *B01D 2251/95* (2013.01); *B01D 2257/504* (2013.01); *B01D 2257/7022* (2013.01); *B01D 2258/05* (2013.01); *C02F 2101/105* (2013.01); *C02F 2101/16* (2013.01); *C02F 2203/006* (2013.01)

(58) Field of Classification Search
CPC ........ C02F 3/2866; C02F 3/325; C02F 3/341; C02F 2101/105; C02F 2101/16; C02F 2203/006; C02F 11/04; C02F 3/308; C02F 3/08; Y02E 50/30; Y02W 10/10; Y02W 10/20; Y02W 10/37
USPC .................. 210/602, 603, 615, 619, 259
See application file for complete search history.

(56) References Cited

U.S. PATENT DOCUMENTS

| | | | |
|---|---|---|---|
| 4,439,315 A | 3/1984 | Whiteside | |
| 4,563,281 A * | 1/1986 | Friedman | C02F 3/082 210/614 |
| 7,850,848 B2 * | 12/2010 | Limcaco | C05F 17/40 210/602 |
| 10,106,765 B2 | 10/2018 | Bernard et al. | |
| 2010/0144017 A1 | 6/2010 | Sims et al. | |
| 2011/0020913 A1 | 1/2011 | Rispoli et al. | |
| 2013/0337548 A1 | 12/2013 | Shepherd | |
| 2020/0048122 A1 * | 2/2020 | Gross | C02F 3/322 |

OTHER PUBLICATIONS

Aas, T. S., Grisdale-Helland, B., Terjesen, B. F., and Helland, S. J. (2006). Improved growth and nutrient utilisation in Atlantic salmon (*Salmo salar*) fed diets containing a bacterial protein meal. Aquaculture 259, 365-376.

Abdel-Raouf, N., Al-Homaidan, A. A., and Ibraheem, I. B. M. (2012). Microalgae and wastewater treatment. Saudi J. Biol. Sci. 19, 257-275.

Abou-Shanab, R. A. I., Ji, M.-K., Kim, H.-C., Paeng, K.-J., and Jeon, B.-H. (2013). Microalgal species growing on piggery wastewater as a valuable candidate for nutrient removal and biodiesel production. J. Environ. Manage. 115, 257-264.

AgSTAR, U.S., 2010. Market opportunities for biogas recovery systems at U.S. livestock facilities.

Angelidaki, I., and Ellegaard, L. (2003). Codigestion of manure and organic wastes in centralized biogas plants. Appl. Biochem. Biotechnol. 109, 95-105.

Badr, K., Hilliard, M., Roberts, N., He, Q. P., and Wang, J. (2019). Photoautotroph-Methanotroph Coculture—A Flexible Platform for Efficient Biological CO2-CH4 Co-utilization. IFAC-PapersOnLine 52, 916-921. doi: 10.1016/j.ifacol.2019.06.179.

Badr, K., Roberts, N., He, Q.P., Wang, J., 2018. Understanding the stability and robustness of a methanotroph-cyanobacterium coculture through kinetic modeling and experimental verification. 2018 AIChE Annu. Conf.

Béchet, Q., Shilton, A., Guieysse, B., 2013. Modeling the effects of light and temperature on algae growth: state of the art and critical assessment for productivity prediction during outdoor cultivation. Biotechnol. Adv. 31, 1648-1663.

Becker, E. W. (2007). Micro-algae as a source of protein. Biotechnol. Adv. 25, 207-210.

Biller, P., and Ross, A. B. (2011). Potential yields and properties of oil from the hydrothermal liquefaction of microalgae with different biochemical content. Bioresour. Technol. 102, 215-225.

11. Biller, P., and Ross, A. B. (2012). Hydrothermal processing of algal biomass for the production of biofuels and chemicals. Biofuels 3, 603-623.

Christenson, L. B. & Sims, R. C. Rotating algal biofilm reactor and spool harvester for wastewater treatment with biofuels by-products. Biotechnol. Bioeng. 109, 1674-1684 (2012).

Driscoll, C., Whitall, D., Aber, J., Boyer, E., Castro, M., Cronan, C., et al. (2003). Nitrogen pollution: Sources and consequences in the US northeast. Environ. Sci. Policy Sustain. Dev. 45, 8-22.

Fei, Q., Guarnieri, M. T., Tao, L., Laurens, L. M. L., Dowe, N., and Pienkos, P. T. (2014). Bioconversion of natural gas to liquid fuel: Opportunities and challenges. Biotechnol. Adv 32, 596-614.

Galloway, J. N., Dentener, F. J., Capone, D. G., Boyer, E. W., Howarth, R. W., Seitzinger, S. P., et al. (2004). Nitrogen cycles: past, present, and future. Biogeochemistry 70, 153-226.

Gamboa-Delgado, J., and Márquez-Reyes, J. M. (2018). Potential of microbial-derived nutrients for aquaculture development. Rev. Aquac. 10, 224-246.

Garcia Alba, L., Torri, C., Samori, C., van der Spek, J., Fabbri, D., Kersten, S. R. A., et al. (2011). Hydrothermal treatment (HTT) of microalgae: evaluation of the process as conversion method in an algae biorefinery concept. Energy & fuels 26, 642-657.

Gross, M., Henry, W., Michael, C. & Wen, Z. Development of a rotating algal biofilm growth system for attached microalgae growth with in situ biomass harvest. Bioresour. Technol. 150, 195-201 (2013).

Gross, M. & Wen, Z. Yearlong evaluation of performance and durability of a pilot-scale revolving algal biofilm (RAB) cultivation system Bioresour. Technol. 171, 50-58 (2014).

Haynes, C. A., and Gonzalez, R. (2014). Rethinking biological activation of methane and conversion to liquid fuels. Nat. Chem. Biol. 10, 331-339.

Henard, C. A., Smith, H., Dowe, N., Kalyuzhnaya, M. G., Pienkos, P. T., and Guarnieri, M. T. (2016). Bioconversion of methane to lactate by an obligate methanotrophic bacterium. Sci. Rep. 6.

Hende, S. Van Den, Carré, E., Cocaud, E., Beelen, V., Boon, N., and Vervaeren, H. (2014). Treatment of industrial wastewaters by microalgal bacterial flocs in sequencing batch reactors. Bioresour. Technol. 161, 245-254.

Hill, E.A., Chrisler, W.B., Beliaev, A.S., Bernstein, H.C., 2017. A flexible microbial co-culture platform for simultaneous utilization of methane and carbon dioxide from gas feedstocks. Bioresour. Technol.

Hoh, D., Watson, S. & Kan, E. Algal biofilm reactors for integrated wastewater treatment and biofuel production: a review. Chem. Eng. J. 287, 466-473 (2016).

Kip, N., van Winden, J.F., Pan, Y., Bodrossy, L., Reichart, G.-J., Smolders, A.J., Jetten, M.S., Damsté, J.S.S., den Camp, H.J.O., 2010. Global prevalence of methane oxidation by symbiotic bacteria in peat-moss ecosystems. Nat. Geosci. 3, 617-621.

Johnson, M. B. & Wen, Z. Development of an attached microalgal growth system for biofuel production. Appl. Microbiol. Biotechnol. 85, 525-534 (2010).

Lee, S. A., Lee, N., Oh, H. M., and Ahn, C. Y. (2019). Enhanced and balanced microalgal wastewater treatment (COD, N, and P) by interval inoculation of activated sludge. J. Microbiol. Biotechnol. doi:10.4014/jmb.1905.05034.

(56) References Cited

OTHER PUBLICATIONS

Lee, S. H. et al. Higher biomass productivity of microalgae in an attached growth system, using wastewater. J. Microbiol. Biotechnol 24, 1566-1573 (2014).
Milucka, J., Kirf, M., Lu, L., Krupke, A., Lam, P., Lillmann, S., Kuypers, M.M., Schubert, C.J., 2015. Methane oxidation coupled to oxygenic photosynthesis in anoxic waters. ISME J.
Muñoz, R., Meier, L., Diaz, I., and Jeison, D. (2015). A review on the state-of-the-art of physical/chemical and biological technologies for biogas upgrading Rev. Environ. Sci. Bio/Technology 14, 727-759.
Nasir, I. M., Mohd Ghazi, T. I., and Omar, R. (2012). Anaerobic digestion technology in livestock manure treatment for biogas production: a review. Eng. Life Sci. 12, 258-269.
Olguin, E. J. (2012). Dual purpose microalgae—bacteria-based systems that treat wastewater and produce biodiesel and chemical products within a Biorefinery. Biotechnol. Adv 30, 1031-1046.
Overland, M., Tauson, A.-H., Shearer, K., and Skrede, A. (2010). Evaluation of methane-utilising bacteria products as feed ingredients for monogastric animals. Arch. Anim. Nutr. 64, 171-189.
Qi, Y., Beecher, N., and Finn, M. (2013). Biogas Production and Use at Water Resource Recovery Facilities in the United States. Water Environ. Fed.
Qu, W., Zhang, C., Zhang, Y., and Ho, S. H. (2019). Optimizing real swine wastewater treatment with maximum carbohydrate production by a newly isolated indigenous microalga *Parachlorella kessleri* QWY28. Bioresour. Technol. doi:10.1016/j.biortech.2019.121702.
Raghoebarsing, A.A., Smolders, A.J., Schmid, M.C., Rijpstra, W.I. C., Wolters-Arts, M., Derksen, J., Jetten, M.S., Schouten, S., Damsté, J.S.S., Lamers, L.P., 2005. Methanotrophic symbionts provide carbon for photosynthesis in peat bogs. Nature 436, 1153-1156.
Rahman, A., and Miller, C. D. (2017). "Microalgae as a Source of Bioplastics," in Algal Green Chemistry: Recent Progress in Biotechnology doi:10.1016/B978 0-444-63784-0.00006-0.
Rasouli, Z., Valverde-Pérez, B., D'Este, M., De Francisci, D., Angelidaki, I., 2018. Nutrient recovery from industrial wastewater as single cell protein by a co-culture of green microalgae and methanotrophs. Biochem. Eng. J. 134, 129-135.
Roberts, N.H., M., Bahr, K., He, Q.P., Wang, J., 2018. Efficient and robust biological CH4/CO2 co-utilization through coculture of methanotroph and microalgae. 40th Symp. Biotechnol. Fuels Chem.
Roberts, N., He, Q.P., Wang, J., 2018. Using methanotroph-microalgae coculture for wastewater treatment. 2018 AIChE Annu. Conf.
Romarheim, O. H., Øverland, M., Mydland, L. T., Skrede, A., and Landsverk, T. (2010). Bacteria grown on natural gas prevent soybean meal induced enteritis in Atlantic salmon J. Nutr. 141, 124-130.
Roberts, N., Hilliard, M., Bahr, K., He, Q. P. & Wang, J. Coculture of Methanotrophs and Microalgae—a Flexible Platform for Biological CH4VCO2 Co-Utilization. 2017 AIChE Annu. Conf. (2017).
Stone, K. A., He, Q. P., and Wang, J. (2019). Two Experimental Protocols for Accurate Measurement of Gas Component Uptake and Production Rates in Bioconversion Processes. Sci. Rep. 9, 5899. doi: 10.1038/s41598-019-42469-3.
Stone, K., He, Q.P., Wang, J., 2017. Systematic Carbon and Growth Analysis of a Promising Methanotroph Strain. 2017 AIChE Annu. Conf.
Su, Y., Mennerich, A., and Urban, B. (2012). Comparison of nutrient removal capacity and biomass settleability of four high-potential microalgal species. Bioresour. Technol. 124, 157-162.
Tandon, P., and Jin, Q. (2017). Microalgae culture enhancement through key microbial approaches. Renew. Sustain. Energy Rev. doi:10.1016/j.rser.2017.05.260.
Teimouri, M., Amirkolaie, A. K., and Yeganeh, S. (2013). The effects of Spirulina platensis meal as a feed supplement an growth performance and pigmentation of rainbow trout (*Oncorhynchus mykiss*). Aquaculture 396, 14-19.
Topper, P. A., Graves, R. E., and Richard, T. (2006). The fate of nutrients and pathogens during anaerobic digestion of dairy manure. Lehman Penn State Univ. Coll. Agric. Sci. Coop. Ext. Bull. G 71.
Toyama, T., Kasuya, M., Hanaoka, T., Kobayashi, N., Tanaka, Y., Inoue, D., et al. (2018). Growth promotion of three microalgae, Chlamydomonas reinhardtii, Chlorella vulgaris and Euglena gracilis, by in situ indigenous bacteria in wastewatereffluent. Biotechnol. Biofuels. doi:10.1186/s13068-018-1174-0.
Van der Ha, D., Nachtergaele, L., Kerckhof, F.-M., Rameiyanti, D., Bossier, P., Verstraete, W., Boon, N., 2012. Conversion of biogas to bioproducts by algae and methane oxidizing bacteria. Environ. Sci. & Technol. 46, 13425-13431.
Wang, J., Liu, W. & Liu, T. Biofilm based attached cultivation technology for microalgal biorefineries—a review. Bioresour. Technol. 244, 1245-1253 (2017).
Wang, K., Mandal, A., Ayton, E., Hunt, R., Zeller, M. A., and Sharma, S. (2016). "Chapter 6—Modification of Protein Rich Algal-Biomass to Form Bioplastics and Odor Removal A2—Dhillon, Gurpreet Singh," in Protein Byproducts doi: https://doi.org/10.1016/B978-0-12-802391-4.00006-9.
Wang, Q., Higgins, B., Ji, H., and Zhao, D. (2018). Improved microalgae biomass production and wastewater treatment: Pretreating municipal anaerobic digestate for algae cultivation, in ASABE 2018 Annual International Meeting doi: 10.13031/aim.201801333.
Wen, Y., He, Y., Ji, X., Li, S., Chen, L., Zhou, Y., et al. (2017). Isolation of an indigenous Chlorella vulgaris from swine wastewater and characterization of its nutrient removal ability in undiluted sewage. Bioresour. Technol. doi: 10.1016/j.biortech.2017.06.094.
Whittenbury, R., Phillips, K. C., and Wilkinson, J. F. (1970). Enrichment, isolation and some properties of methane-utilizing bacteria. J. Gen. Microbiol. doi:10.1099/00221287-61-2-205.
Woertz, I., Feffer, A., Lundquist, T., and Nelson, Y. (2009). Algae grown on dairy and municipal wastewater for simultaneous nutrient removal and lipid production for biofuel feedstock. J. Environ. Eng. 135, 1115-1122.
Xia, A., and Murphy, J. D. (2016). Microalgal Cultivation in Treating Liquid Digestate from Biogas Systems. Trends Biotechnol. doi:10.1016/j.tibtech.2015.12.010.
Zeller, M. A., Hunt, R., Jones, A., and Sharma, S. (2013). Bioplastics and their thermoplastic blends from Spirulina and Chlorella microalgae. J. Appl. Polym. Sci. doi:10.1002/app.39559.
Zou, S., Wu, Y., Yang, M., Li, C., and Tong, J. (2009). Thermochemical catalytic liquefaction of the marine microalgae Dunaliella tertiolecta and characterization of bio-oils. Energy & Fuels 23, 3753-3758.
International Search Report and Written Opinion for PCT/US2020/042891 dated Oct. 28, 2020.

\* cited by examiner

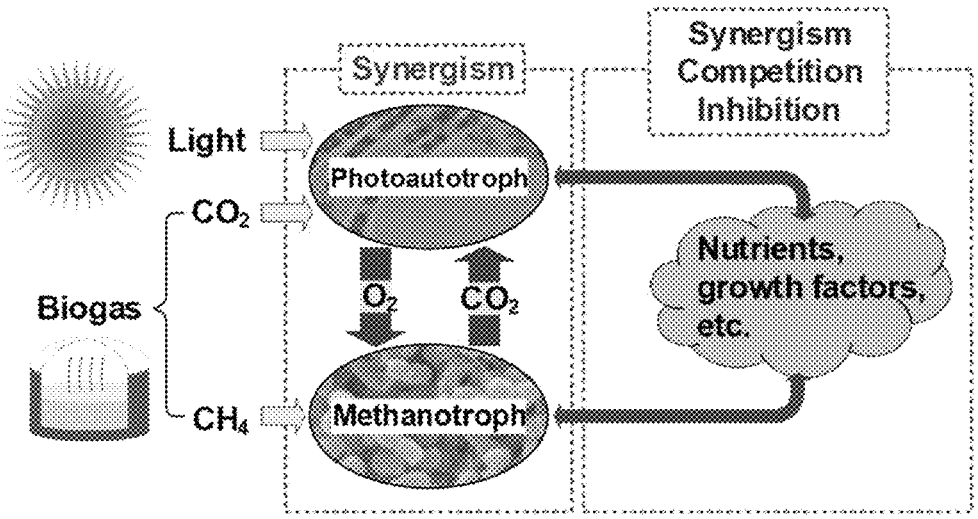

FIG. 3

$$(\Delta CH_4)_{met} = (\Delta CH_4)_{head} \quad (1)$$

$$(\Delta O_2)_{met} = (\Delta CH_4)_{met} \cdot \left(Y_{\frac{O_2}{CH_4}}\right)_{met} \quad (2)$$

$$(\Delta CO_2)_{met} = -(\Delta CH_4)_{met} \cdot \left(Y_{\frac{CO_2}{CH_4}}\right)_{met} \quad (3)$$

$$(\Delta X)_{met} = (\Delta CH_4)_{met} \cdot \left(Y_{\frac{X}{CH_4}}\right)_{met} \quad (4)$$

$$(\Delta O_2)_{head} = (\Delta O_2)_{met} + (\Delta O_2)_{alg} \quad (5)$$

$$(\Delta CO_2)_{head} = (\Delta CO_2)_{met} + (\Delta CO_2)_{alg} + (\Delta CO_2)_{dis} \quad (6)$$

$$(\Delta X)_{alg} = \frac{1}{2}\left[(\Delta CO_2)_{alg} \cdot \left(Y_{\frac{X}{CO_2}}\right)_{alg} + (\Delta O_2)_{alg} \cdot \left(Y_{\frac{X}{O_2}}\right)_{alg}\right] \quad (7)$$

Subscripts:
met: methanotroph; alg: algae;
head: headspace; dis: dissolved.

FIG. 4

CULTURE SYSTEMS AND METHODS OF USING SAME

CROSS-REFERENCE TO RELATED APPLICATIONS

Priority is hereby claimed to provisional application Ser. No. 62/877,126, filed Jul. 22, 2019, and Ser. No. 63/047,114, filed Jul. 1, 2020, the contents of which are incorporated herein by reference in their entireties.

STATEMENT REGARDING FEDERALLY SPONSORED RESEARCH

This invention was made with government support under DE-SC0019181 awarded by the Department of Energy. The government has certain rights in the invention.

FIELD OF THE INVENTION

The invention is directed to culture systems, such as microbial culture systems useful for co-culturing methanotrophs and phototrophs in the presence of biogas and wastewater, and methods of using same.

BACKGROUND

Anaerobic digestion is a biological process in which a consortium of microorganisms breaks down waste, controls odor, and reduces >95% pathogens. Anaerobic digestion is one of the most effective technologies for managing organic waste streams at wastewater treatment plants. As a result, nearly half of the municipal wastewater in the US is treated via Anaerobic digestion. However, plants that utilize anaerobic digestion have faced some key economic challenges including: (1) the high cost of removing high concentrations of ammonia and phosphorus (both of which are environmentally regulated) in the digestate; and (2) the high cost of removing contaminants in the biogas (e.g., hydrogen sulfide, ammonia, volatile organic carbons (VOCs), and moisture) prior to downstream use. These challenges impose an economic burden and have significantly reduced the return on investment for these plants.

Systems and methods for addressing these problems and other problems are needed.

SUMMARY OF THE INVENTION

The invention is directed to systems and methods that can be used to address the aforementioned problems in the art.

The systems of the invention generally include a housing, a headspace, a reservoir, and a surface. The housing comprises a top and sides and defines an inner space extending between the sides and to the top. The headspace is located in an upper portion of the inner space. The reservoir comprises at least a first reservoir portion that is located in a lower portion of the inner space. The headspace and the reservoir are defined with respect to each other within the inner space by a horizontal plane spanning the inner space, and the headspace and the reservoir do not overlap within the inner space. The surface comprises a surface portion capable of being cycled between the headspace and the reservoir.

The methods of the invention can generally comprise culturing a cell adhered to the surface portion of the surface in a system of the invention. The methods can be used to remove at least one of methane and carbon dioxide from gas while simultaneously removing at least one of inorganic nitrogen and inorganic phosphorus from liquid.

An exemplary version of the invention is a system 1 shown in FIG. 1A, which is referred to herein as a circulating coculture biofilm photobioreactor (CCBP). An exemplary placement of the CCBP in an exemplary processing stream of the invention is shown in FIG. 2B. The CCBP enables wastewater treatment plants that utilize anaerobic digestion to valorize their waste and meet regulatory requirements at a fraction of their current costs. The CCBP can employ a coculture of microorganisms (e.g., of phototrophs and methanotrophs) that is capable of consuming both the methane ($CH_4$) and carbon dioxide ($CO_2$) from raw biogas (untreated) produced by anaerobic digestion as well as the ammonia and phosphorus present in the anaerobic digestion digestate. The biomass produced is a suitable candidate for animal feed (e.g., aquafeed) due to its high protein, carbohydrate, and amino acid content and/or a viable feedstock for producing value-added products such as bioplastics and biofuels, rendering the biomass a valuable product that can generate revenue for the wastewater treatment plants. The biofilm is cultivated on a substratum surface 7 (belt material), as shown in FIG. 1A, that is part of a conveying system. The vertical arrangement of the conveying system's rotary shafts 20,21,22,23 provides a large surface area for the biofilm to grow, maximizing productivity while minimizing areal requirement. As the belt rotates, the biofilm is continuously conveyed into a headspace 4 where the cells uptake the $CH_4$ and $CO_2$ from the biogas and subsequently into the liquid phase (e.g., anaerobic digestion digestate, or wastewater from any stage of the treatment, or a mixture of the above) where the cells can uptake nutrients, including ammonia and phosphorus. Ammonia and phosphorus concentration in wastewater treatment plant discharge is tightly regulated. The coculture can remove both ammonia and phosphorus to levels that exceed current regulatory requirements. Once the biofilm has grown to a predetermined thickness, the biomass can be easily harvested at high solids content using a retractable press wheel 13 and retractable blade 14, minimizing energy input and eliminating the need for some downstream processing steps (e.g., dewatering). In summary, the CCBP can convert waste (biogas and anaerobic digestion digestate) into valuable products while concurrently enabling the wastewater treatment plants to meet regulatory requirements, all at a fraction of the current cost for wastewater treatment.

The objects and advantages of the invention will appear more fully from the following detailed description of the preferred embodiment of the invention made in conjunction with the accompanying drawings.

BRIEF DESCRIPTION OF THE DRAWINGS

FIG. 3 shows a schema of synergistic interactions within a microalgae-methanotroph coculture.

FIG. 4 shows a computational procedure to estimate $O_2$ and $CO_2$ consumed/produced by methanotrophs and algae during light cycles.

FIG. 5C shows that with the same inoculum, microalgae produce more $O_2$ in coculture than in single couture; Even with coculture $O_2$ amount injected into methanotroph single culture (Case C), its growth is still slower than coculture as shown in FIG. 5A, suggesting other factors that play a role in enhancing coculture growth. Shaded periods indicate dark cycles and light cycles are denoted as L followed by a number.

FIG. 9A shows growth of total biomass. FIGS. 9B and 9C respectively show calculated growth of *M. capsulatus* and *C. sorokiniana* individually in the coculture, as calculated using the established protocol of Badr et al., 2019. FIGS. 9A-9C reveal better growth performance on AD-CLE than on AD-TW or AD-AMS.

FIG. 12A shows growth of total biomass. FIGS. 12B and 12C respectively show calculated growth of *C. sorokiniana* and *M. capsulatus* individually in the coculture.

DETAILED DESCRIPTION OF THE INVENTION

Figure 1A:
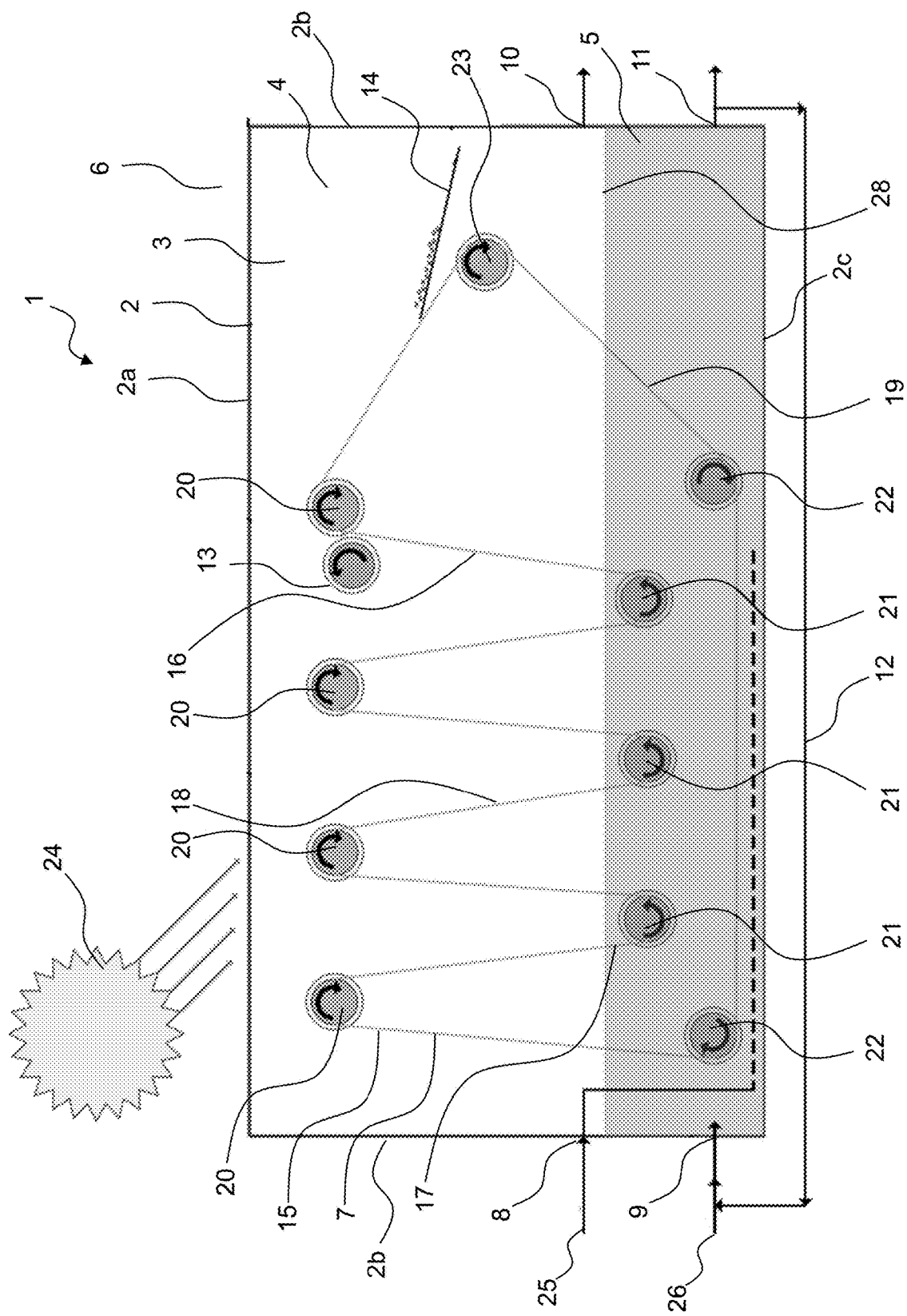
FIG. 1A shows a side elevation view of an exemplary system of the invention.
Figure 1B:
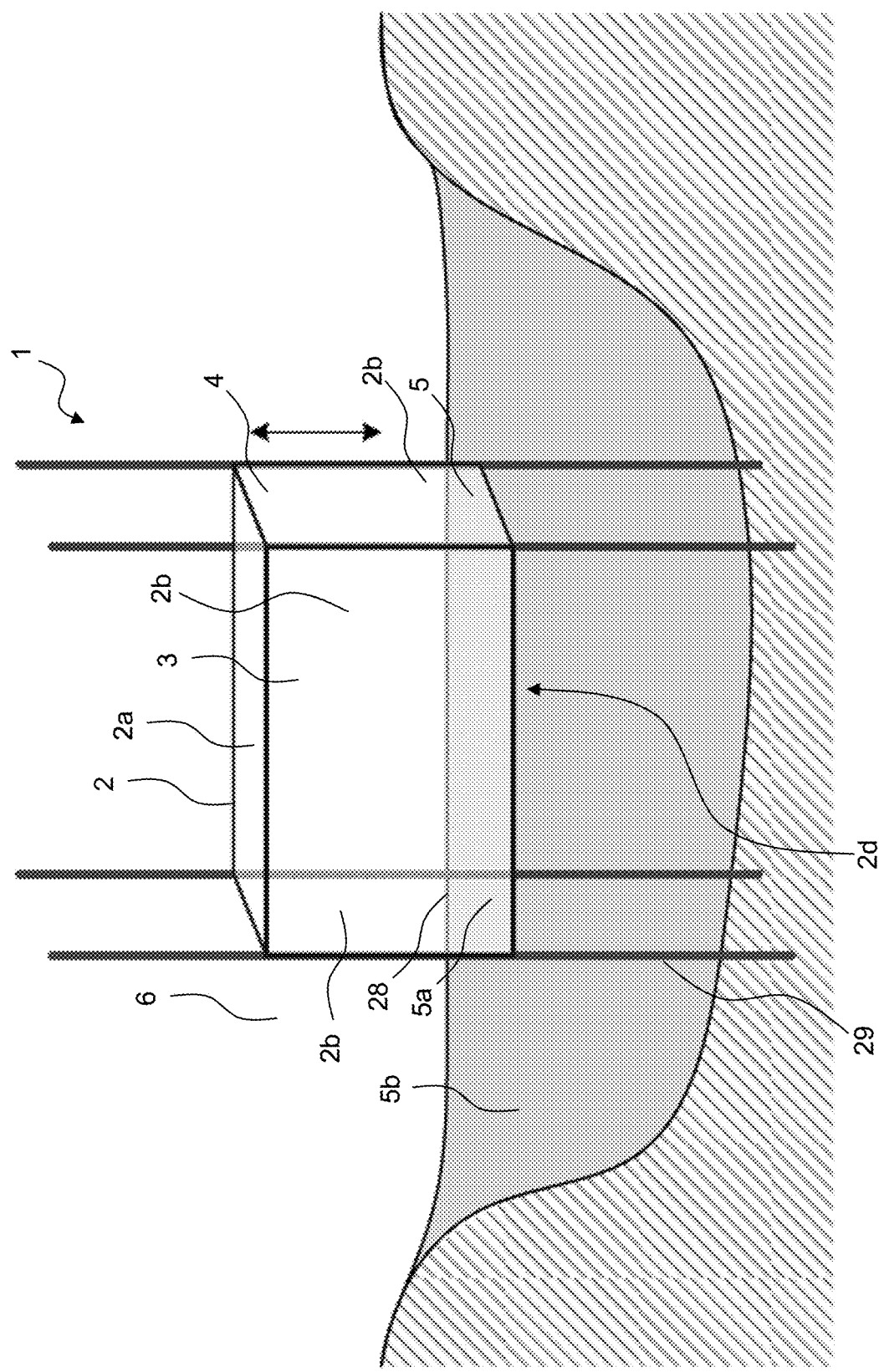
FIG. 1B shows a side elevation view of alternative housing and reservoir configuration than that shown in FIG. 1A. Any elements shown in the exemplary system of FIG. 1A can be incorporated with the elements shown in FIG. 1B.

Reference numbers provided in the following description refer to exemplary versions of the invention as shown in FIGS. 1A and 1B. One aspect of the invention is directed to a system 1. The system 1 generally includes a housing 2. The housing 2 can include at least a top 2a and sides 2b. The top 2a and sides 2b define an inner space 3 extending between the sides 2b and to the top 2a. In some versions, such as the version shown in FIG. 1A, the housing 2 further includes a bottom 2c such that the housing forms an enclosure enclosing the inner space 3. In some versions, such as the version shown in FIG. 1B, the housing 2 includes a bottom opening 2d.

Regardless of whether the housing 2 includes a bottom 2c or a bottom opening 2d, the inner space 3 defined by the housing 2 includes a headspace 4 in an upper portion of the inner space 5 and at least a portion of a reservoir 5 in a lower portion of the inner space. The headspace 4 and the reservoir 5 are defined with respect to each other within the inner space 3 by a horizontal plane 28 spanning the inner space 3, and the headspace 4 and the reservoir 5 do not overlap within the inner space 3.

In some versions, such as the version shown in FIG. 1A, the reservoir 5 is entirely encompassed within the inner space 3. In some versions, such as the version shown in FIG. 1B, the reservoir 5 includes a first reservoir portion 5a and a second reservoir portion 5b. The first reservoir portion 5a is encompassed within the inner space 3. The second reservoir portion 5b is located below the first reservoir portion 5a and is contiguous with both the first reservoir portion 5a and a surrounding space 6 that surrounds the portion of the housing 2 defining the headspace 4. The surrounding space 6 can include the open air of the atmosphere. The reservoir 5 in FIG. 1B can comprise a body of wastewater outdoors, such as a pond or lagoon (e.g., containing wastewater), and the housing 2 and other components of the system can be suspended partially above and partially in the reservoir with housing supports 29.

Figure 2A:
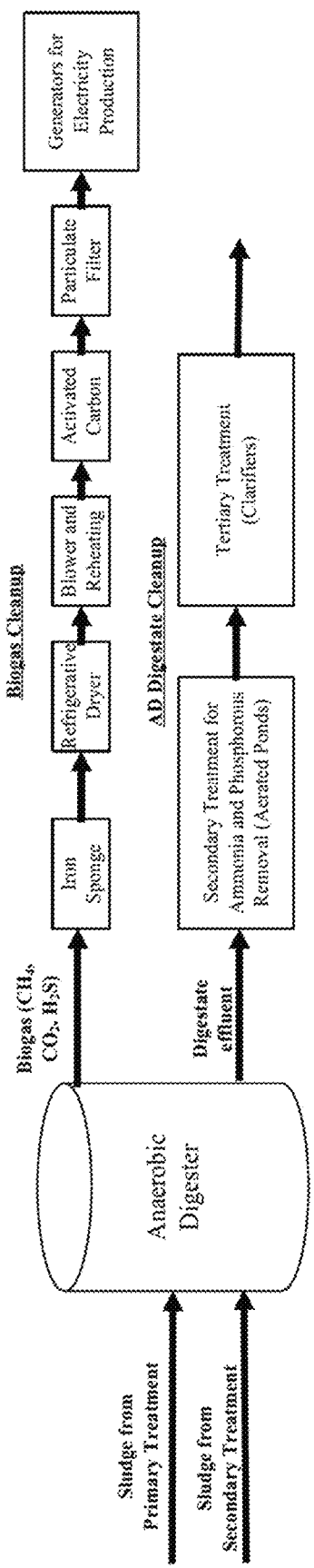
FIGS. 2A and 2B show wastewater treatment plant process flows, with FIG. 2A showing a conventional process flow and FIG. 2B showing an exemplary process flow of the invention, wherein "CCBP" refers to a circulating coculture biofilm photobioreactor system of the invention.
Figure 2B:
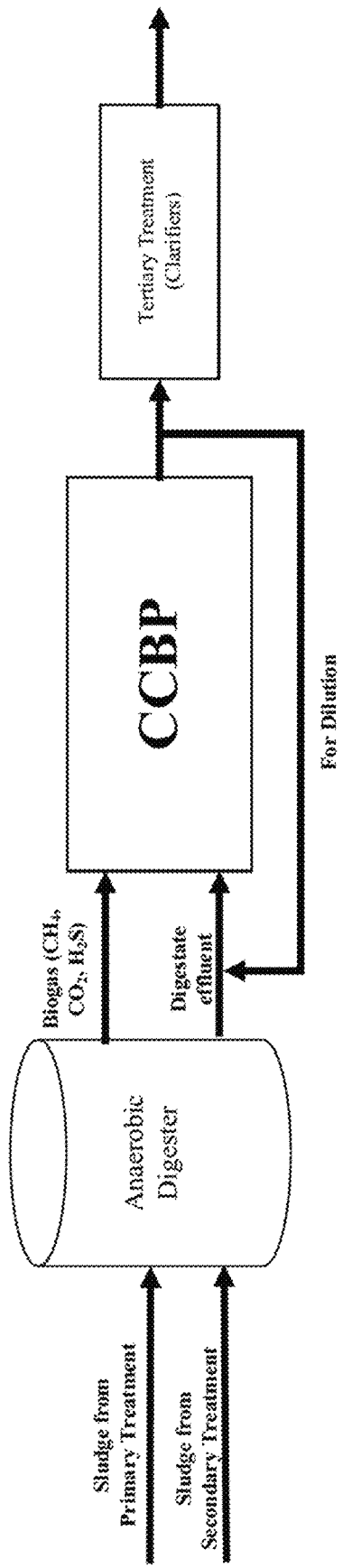

The housing 2 in the exemplary versions shown in both FIGS. 1A and 2B forms a "closed system" around at least the headspace 4 such that the housing 2 is capable of maintaining a gaseous composition of the headspace 4 that is different from a gaseous composition of the surrounding space 6. In the version shown in FIG. 1A, the housing 2 forms a closed system around both the headspace 4 and the reservoir 5. Accordingly, the housing 2 is preferably impermeable or at least substantially impermeable to fluids such as gases and liquids. The housing 2, or at least a portion thereof, is also preferably permeable to visible light, particularly the wavelengths of light involved in photosynthesis. These wavelengths include light falling within the blue (425-450 nm) and red (600-700 nm) ranges. Glass and various plastics, such as acrylics (polymethlamethacrylate), butyrate (cellulose acetate butyrate), lexan (polycarbonate), PETG (glycol modified polyethylene terphthalate), and combinations thereof are impermeable to fluids and are permeable to visible light, making them suitable housing 2 materials.

The system 1 also generally includes a surface 7. The surface 7 includes at least one surface portion. The surface portion can comprise any portion of the surface 15. The surface portion is capable of being cycled between the headspace 4 and the reservoir 5.

The surface 7 is preferably a surface suitable for cell adhesion. The surface can comprise such materials as cotton-based material (i.e., cotton duck), fiberglass, nylon, polypropylene, and combinations or hybrids of any of the foregoing. Any other materials suitable for cell adhesion are also acceptable.

The surface 7 can take any of a variety of forms. In the exemplary system 1, the surface 7 is configured in the form of a continuous conveyor belt. The conveyor belt is capable of being moveable along a conveyor belt path that is capable of proceeding through both the headspace 4 and the reservoir 5. In other versions, the surface 7 takes the form of one or more paddles that are cycled through and between the headspace 4 and the reservoir 5, for example, by being connected to a central rotatable hub. Other configurations are acceptable.

In various versions of the invention, at least about 10%, at least about 20%, at least about 30%, at least about 40%, at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of the length of the conveyor belt path is capable of being disposed in the headspace 4, such as during normal operation. In various versions of the invention, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 30%, at least about 40%, at least about 50%, at least about 60%, at least about 70%, at least about 80%, or at least about 90% of the length of the conveyor belt path is capable of being disposed in the reservoir 5, such as during normal operation. Various ratios of the proportion of the length of the conveyor capable of being disposed in the headspace 4 versus the proportion of the length of the conveyor capable of being disposed in the reservoir 5, such as during normal operation, are permitted. Exemplary acceptable ratios include 99:1 (headspace:reservoir), 95:5 (headspace: reservoir), 90:10 (headspace: reservoir), 85:15 (headspace: reservoir), 80:20 (headspace:reservoir), 75:25 (headspace:reservoir), or 70:30 (headspace: reservoir), or any range between any of the aforementioned ratios. Exemplary ratio ranges include from about 99:1 (headspace:reservoir) to about 70:30 (headspace:reservoir), from about 99:1 (headspace:reservoir) to about 75:25 (headspace:reservoir), or from about 99:1 (headspace:reservoir) to about 80:20 (headspace:reservoir). As discussed in further detail below, 100% of the conveyor belt path can be disposed in the headspace 4 during certain aspects of operation, such as during startup.

The conveyor belt in the exemplary system 1 is positioned with support shafts 20,21,22,23. The support shafts 20,21, 22,23 in the exemplary system 1 include long axes configured in a parallel orientation with respect to each other by being supported by a frame within the inner space 3, by the housing 2 itself, or by any other suitable support mechanism. The support shafts 20,21,22,23 in the exemplary system 1 are preferably rotary shafts that are rotatable about their long axes.

The support shafts 20,21,22,23 in the exemplary system 1 include upper shafts 20, lower shafts 21, return shafts 22, and one or more tensions shafts 23. The upper shafts 20 in the exemplary system 1 are positioned within the headspace 4 and support an inner side of the conveyor belt. The upper shafts 20 guide the conveyor belt to and through the headspace 4. The lower shafts 21 are in the exemplary system 1 are positioned within the reservoir 5 during normal operation and support an outer side of the conveyor belt. The lower shafts 21 in the exemplary system 1 guide the conveyor belt to and through at least a portion of the reservoir 5. The return shafts 22 are positioned under the lower shafts 21 and support an inner side of the conveyor belt. The return shafts 22 guide the conveyor belt from the headspace 4, through the reservoir 5, and back to the headspace 4. The tension shaft(s) 23 can support either the inner or outer side of the conveyor belt and be positioned anywhere in the inner space 3. In the exemplary system 1, a tension shaft 23 is positioned in the headspace 4 and supports the inner side of the conveyor belt.

The tension shaft 23 serves to adjust the tension/slack on the conveyor belt, such as by being moveable in a vertical and/or horizontal direction orthogonal to its long axis within the inner space 3. The tension shaft 23 also serves to angle the conveyor belt for efficient harvesting of cells, which is discussed in further detail below. As shown in the exemplary system 1, it is preferred to position the lower shafts 21 within the reservoir 5. This permits frequent wetting of portions of the conveyor belt (and exposure of cells adhered thereto to liquid nutrients such as inorganic nitrogen and inorganic phosphorus) as it travels along the conveyor belt path through the headspace 4. However, in some versions of the invention, one or more lower shafts 21 can be positioned within the headspace 4.

By virtue of the placement of the upper shafts 20 relative to the lower shafts 21, the conveyor belt path can take the form of a zigzag pattern with portions of the conveyor belt path being positioned along one or more planes angled with respect to the horizontal plane. The zigzag portion includes a first upper end 15, a second upper end 16, and at least one internal lower portion 17. The first upper end 15 is preferably disposed in the headspace. The second upper end 16 is also preferably disposed in the headspace. The at least one internal lower portion 17 is positioned in the conveyor belt path between the first upper end 15 and the second upper end 16 and is positioned in the inner space 3 below the first upper end 15 and the second upper end 16, preferably within the reservoir 5 during normal operation. In some versions, such as the exemplary system 1, multiple internal lower portions 17 are included. Each of these internal lower portions 17 are separated from each other by an internal upper portion 18 positioned within the enclosed space above the internal lower portions, preferably within the headspace 4. As outlined above, it is preferred to position the internal lower portions 17 within the reservoir 5 to permit frequent wetting of portions of the conveyor belt (and exposure of cells adhered thereto to liquid nutrients such as inorganic nitrogen and phosphorus) by dipping the conveyor belt portions in a liquid in the reservoir 5 as they travel along the conveyor belt path. However, in some versions of the invention, one or more internal lower portions 17 can be positioned within the headspace 4.

The planes defined by the conveyor belt path in the zigzag configuration can be angled at any suitable angle for optimizing the amount of light being directed at the surface 7. Exemplary angles include about 5°, about 10°, about 15°, about 20°, about 25°, about 30°, about 35°, about 40°, about 45°, about 50°, about 55, about 60°, about 65°, about 70°, about 75°, about 80°, about 85°, about 90°, or about 95° with respect to the horizontal plane, or any range between any of the foregoing values. Exemplary ranges include from about 15° to about 75°, from about 20° to about 70°, from about 25° to about 65°, from about 30° to about 60°, from about 35° to about 55°, or from about 40° to about 50°.

In some versions of the invention, the angles of the planes defined by the conveyor belt path in the zigzag configuration are capable of being continuously adjustable with respect to the horizontal plane. In some versions, the planes are continuously adjustable along an angle from 10° to 90° with respect to the horizontal plane or any subrange thereof spanning at least 2.5°, at least 5°, at least 10°, at least 15°, at least 20°, at least 25°, at least 30°, at least 35°, at least 40°, at least 45°, at least 50°, at least 55°, at least 60°, at least 65°, at least 70°, or at least 75°. In some versions, the planes are continually adjustable along an angle from 30° to 60° or any subrange thereof spanning at least 2.5°, at least 5°, at least 10°, at least 15°, at least 20°, or at least 25°. In such versions, the planes can be continuously adjustable within any range of angles mentioned above. This can be accomplished by increasing/decreasing the vertical distance between the upper shafts 20 and the lower shafts 21, decreasing/increasing the horizontal distance between the upper shafts 20, and/or increasing/decreasing the horizontal distance between the lower shafts 21. These adjustments can be accomplished by supporting each upper and lower shaft 20,21 on individual, continuously adjustable frames or by supporting each upper and lower shaft 20,21 in moveable elements within a single frame. At least in some versions of the invention, the purpose of the zigzag portion and its adjustability is to expose cells to optimal light intensity for achieving maximum cell growth, as discussed in further detail below.

In order to cycle the conveyor belt path from the second upper end 16 of the zigzag portion to the first upper end 15 of the zigzag portion, the conveyor belt path further comprises a return portion 19. The return portion 19 in the exemplary system 1 is guided by the return shafts 22. The return portion 19 is capable of being at least partially disposed within the reservoir 5, which can be accomplished by positioning one or more of the return shafts 22 in the reservoir 5.

The positioning of the various support shafts 20,21,22,23 and conveyor belt path in either in the headspace 4 or the reservoir 5 as described above is preferred during normal operation of the system 1. In some versions of the invention, the support shafts 20,21,22,23 are supported on a frame that can be entirely moved vertically to raise all the support shafts 20,21,22,23 and the entire surface 7 into the headspace 4. The surface 7 can thereby operate completely above the reservoir 5. In such a case, a liquid sprayer can transport liquid onto the surface 7. This configuration can be employed during system startup to avoid the biofilm from being washed away if passing through the liquid phase. After startup, the frame can then be lowered to drop at least some of the support shafts (preferably the lower shafts 21 and return shafts 22) and portions of the conveyer belt path (preferably the internal lower portions 17 and return portion 19 of the conveyor belt path) into the reservoir 5.

One or more of the support shafts 20,21,22,23 in the system 1 can be translationally moveable with respect to one or more other support shafts 20,21,22,23 while maintaining their parallel orientation. The translational movement is preferably in a direction orthogonal to the long axes of the support shafts 20,21,22,23. The translational movement can be accomplished by supporting any one or more of the support shafts 20,21,22,23 on individual, continuously adjustable frames or by supporting any one or more support shafts 20,21,22,23 in moveable elements within a single frame. The translational movement can be employed to move the upper shafts 20 with respect to the lower shafts 21 to change the angle of various portions of the conveyor belt path, as described above. The translational movement can also be employed to move the tension shaft 23 with respect to the other shafts 20,21,22 to maintain an appropriate level of tension on the conveyor belt.

The system 1 can include one or more ports 8,9,10,11 in fluid connection with the enclosed space to permit selective entry or efflux of fluids such as gas and/or liquid into or from the inner space 3. Each port 8,9,10,11 can independently have either a constitutive fluid connection or a regulatable fluid connection. A port with a constitutive fluid connection is an open port that permits fluid flow in an unregulated manner. A port with a regulatable fluid connection is a port that permits regulated fluid flow through the port, such as with a controllable valve. The exemplary system 1 as shown in FIG. 1A includes a first intake port, a second intake port, 9, a headspace outlet port 10, and a reservoir outlet port 11.

The placement of the ports can facilitate selective efflux of specific contents from the enclosed space. For example, the headspace outlet port 10 is positioned within the headspace 4 to provide direct fluid connection with the headspace 4 and provide selective efflux of headspace 4 contents from the inner space 3. In addition, the reservoir outlet port 11 is positioned in the reservoir 5 to provide direct fluid connection with the reservoir 5 and provide selective efflux of reservoir 5 contents from the inner space 3. As used herein, "direct fluid connection" used with reference to a particular element refers to a fluid connection with that particular element that does not require flow through another element. For example, a direct fluid connection with the headspace 4 does not require flow through the reservoir 5 to reach the headspace 4. Conversely, a direct fluid connection with the reservoir 5 does not require flow through the headspace 4 to reach the reservoir 5.

In some versions of the invention, such as that shown in FIG. 1A, at least one of the ports 8,9,10,11 is in fluid connection with another one of the ports 8,9,10,11 via a channel that at least partially bypasses the enclosed space. This can permit selective recycling of specific contents of the inner space 3 back into the inner space 3. In the exemplary system 1, for example, the reservoir outlet port 11 is in fluid connection with the second intake port 9 via a return channel 12. As described in further detail below, this can permit recycling of liquid from the reservoir 5 back into the inner space 3 to dilute liquid from the liquid source 26.

During operation of the system 1, the headspace 4 can be filled with a gas and the reservoir 5 can be filled with a liquid. The gas can be provided via the first intake port 8 by virtue of the first intake port being in fluid connection with a gas source 25, and the liquid can be provided by the second intake port 9 by virtue of being in fluid connection with a liquid source 26. The system 1 of the invention is particularly suited for simultaneously processing a gas containing methane and/or carbon dioxide and wastewater, such as wastewater containing high levels of inorganic nitrogen and inorganic phosphorus. Accordingly, the gas filling the headspace 4 and/or supplied thereto from the gas source 25 can comprise a gas comprising at least one of methane and/or carbon dioxide, such as biogas or natural gas. The liquid filling the reservoir 5 and/or supplied thereto from the liquid source 26 can comprise wastewater, such as water containing inorganic nitrogen and inorganic phosphorus. An exemplary source of biogas and wastewater than can be processed in the system 1 of the invention is an anaerobic digester, such as an anaerobic digester at a wastewater (sewage or other) treatment plant, wherein the gas is derived from the headspace of the anaerobic digester and the wastewater comprised of digestate effluent from the anaerobic digester. The wastewater, however, can comprise wastewater during any stage of treatment or any mixture of wastewater during any stage of treatment.

"Biogas" as used herein refers to a mixture of gases produced by the breakdown of organic matter in the absence of oxygen (anaerobically), primarily including methane and carbon dioxide but also possibly including hydrogen sulfide ($H_2S$), moisture, and siloxanes, among other components. Biogas can be produced from raw materials such as agricultural waste, manure, municipal waste, plant material, sewage, green waste, or food waste. Biogas can be produced by anaerobic digestion with methanogen or anaerobic organisms, which digest material inside a closed system, or fermentation of biodegradable materials. Such systems include anaerobic digester, biodigesters or bioreactor.

In various versions of the invention, the gas supplied to the inner space 3 of the system 1 and reacted therein includes methane in an amount of at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, or at least about 99% v/v. Biogas, for example, typically contains methane in an amount of about 50-70% v/v.

In various versions of the invention, the gas supplied to the inner space 3 of the system 1 and reacted therein includes carbon dioxide in an amount of at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, or at least about 99% v/v. Biogas, for example, typically contains carbon dioxide in an amount of about 30-40% v/v.

"Wastewater" as used herein refers to water contaminated by human use and can comprise, without limitation, human excreta (feces, urine, blood and other bodily fluids); washing water (personal hygiene, clothes, floors, dishes, cars, etc.), also known as greywater or sullage; surplus manufactured liquids from domestic sources (drinks, cooking oil, pesticides, lubricating oil, paint, cleaning detergents, etc.); industrial site drainage (silt, sand, alkali, oil, chemical residues); industrial processing waters; organic or biodegradable waste, including waste from hospitals, abattoirs, creameries, and food factories; organic or non-biodegradable waste from pharmaceutical or pesticide manufacturing; toxic waste from metal plating, cyanide production, pesticide manufacturing, etc.; water used in hydraulic fracturing; produced water from oil & natural gas production; urban runoff from highways, roads, railway tracks, car parks, roofs, and/or pavements (containing, for example, oils, animal feces/manure, food waste, litter, petrol, diesel, rubber residues from tires, soap scum, metals from vehicle exhausts, de-icing agents, herbicides and pesticides from gardens, etc.); sewage; fecal sludge, agricultural runoff or pollution; among others. An exemplary wastewater is liquid effluent from an anaerobic digester, such as an anaerobic sewage or sludge digester, and an exemplary wastewater source is the liquid reservoir of an anaerobic digester, such as an anaerobic sewage or sludge digester. Particular examples of wastewater include animal farm wastewater, vegetable farm wastewater, food-processing plant wastewater, winery wastewater, landfill wastewater, and fishery wastewater.

In various versions of the invention, the liquid supplied to and/or included in the inner space 3 of the system 1 can include inorganic nitrogen in an amount of about 10 mg/L, about 25 mg/L, about 75 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, or any range between any of the foregoing values. Exemplary ranges include from about 25 mg/L to about 400 mg/L, about 100 mg/L to about 300 mg/L, or about 150 mg/L to about 250 mg/L. The inorganic nitrogen can include any one or more of nitrate, nitrite, ammonia, and ammonium, among others.

In various versions of the invention, the liquid supplied to and/or included in the inner space 3 of the system 1 can include inorganic phosphorus in an amount of about 10 mg/L, about 25 mg/L, about 75 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, or any range between any of the foregoing values. Exemplary ranges include from about 25 mg/L to about 425 mg/L, about 125 mg/L to about 325 mg/L, or about 175 mg/L to about 275 mg/L. The inorganic phosphate can include any one or more of phosphate (orthophosphate) ($[PO_4]^{3-}$), phosphoric acid ($H_3PO_4$), dihydrogen phosphate ($[H_2PO_4]^-$), and hydrogen phosphate ($[HPO_4]^{2-}$).

During operation of the system 1, the surface 7 can have cells adhered thereto for cultivation, and the cells can thereby be cycled between the headspace 4 and reservoir 5 for efficient cultivation. To facilitate harvesting the cells after growth, the system 1 can include a retractable press capable of being reversibly positioned against the surface 7 to remove moisture from the cells by squeezing the cells against the surface 7. In the exemplary system 1, the retractable press includes a retractable press wheel 13 capable of being reversibly positioned against the conveyor belt and pressing the surface against one of the upper shafts 20. As described above with respect to the support shafts 20,21,22,23, the retractable press wheel 13 can be independently moveable by supporting the retractable press wheel 13 on an individual, adjustable frame or by supporting the retractable press wheel 13 on a moveable element within a single frame that supports one or more of the support shafts 20,21,22,23. To further facilitate harvesting the cells, the system 1 can further include a retractable scraper 14 capable of being reversibly positioned against the surface 7 to scrape cells from the surface 7. The activation of the retractable press (such as the retractable press wheel 13) and the retractable scraper 14 can be actuated in an automated manner with a sensor capable of sensing a condition of the surface, such as a particular biofilm thickness on the surface or any other relevant condition.

For processing certain types of substrates, such as methane-containing gases and wastewater, the cells adhered to the surface 7 can include one or both of a methanotroph and a phototroph.

Methanotrophs are organisms that metabolize methane as their source of carbon and energy. Suitable methanotrophs include species of bacteria and/or archaea. Exemplary suitable methanotrophs include species from the genus *Methylococcus*, such as *Methylococcus capsulatus;* species from the genus *Methylocystis;* species from the genus *Methylosinus*, such as *Methylosinus trichosporium* OB3b; species from the genus *Methylomonas*, such as *Methylomonas* sp. LW13; species from the genus *Methylosarcina*, such as *Methylosarcina fibrate, Methylosarcina quisquiliarum,* and *Methylosarcina lacus* sp. nov. LW14T; and species from the genus *Methylomonas*, such as *Methylomonas methanica* S1.

Phototrophs are organisms that convert light into energy. Preferred phototrophs are photoautotrophs that can perform photosynthesis. Suitable phototrophs include but are not limited to algae, including microalgae, and cyanobacteria. Exemplary suitable microalgae species include species from the genus *Chlorella*, such as *Chlorella sorokiniana, Chlorella zofingiensis, Chlorella vulgaris,* and *Chlorella kessleri;* species from the genus *Scenedesmus;* species from the genus *Scenedesmus*, such as *Scenedesmus obliquus* and *Scenedesmus dimorphus;* and species from the genus *Mucidosphaerium*, such as *Mucidosphaerium pulchellum*. Exemplary suitable cyanobacteria include species from the genus *Agmenellum, Anabaena, Aphanocapsa, Arthrosprira, Gloeocapsa, Haplosiphon, Mastigocladus, Nostoc, Oscillatoria, Prochlorococcus, Scytonema, Synechococcus* (e.g., *Synechococcus* sp. PCC 7942 and *Synechococcus* sp. PCC 7002), and *Synechocystis* (e.g., *Synechocystis* sp. PCC 6803).

For growth of phototrophs, the system 1 can be positioned with respect to a light source 24 directed at least to a portion of the surface 7. The light source 24 can include the sun and/or an artificial (i.e., non-solar) light source. In some versions, the light source includes both the sun 24 and an artificial light source, such as an LED light. The artificial light source can be activated to supplement sunlight during low-light situations or can be used in place of sunlight during the night. The intensity of the artificial light source can be automatically controlled or adjusted based on the external natural light intensity, gas phase condition, and biofilm condition on the surface 7. The artificial light source can be powered by an energy store, such as a battery or any other mechanism, system, or device capable of storing energy. The energy store can be charged by a solar panel.

The systems of the invention can be used for culturing cells, such as for the purpose of processing certain gases and liquids. "Processing" as used herein refers to consuming and/or changing the chemical composition of a substance, such as a gas or a liquid.

As described with respect to the exemplary system 1, for example, cells can be adhered to the surface 7, such as the conveyor belt shown in the exemplary system 1. Gas can be introduced into the inner space 3 to fill the headspace 4 from a gas source 25 via the first intake port 8. Liquid can be introduced into the inner space 3 to fill the reservoir 5 from a liquid source 26 via the second intake port 9, as shown in FIG. 1A, or can be introduced into the inner space 3 via the bottom opening 2d, as shown in FIG. 2B. The cells can be cycled through the headspace 4 and the reservoir 5 to both grow the cells and process the gas and/or liquid. If the cells being cultivated include phototrophs, the system 1 can include a light-permeable housing 2 and can be situated with respect to a light source 24, such as the sun and/or an artificial light source. The zigzag portion of the surface 7 can be adjusted to optimize the amount of light reaching the cells on the surface 7. When the cells have reached a desired state of growth, the retractable press wheel 13 and retractable scraper 14 can be activated to dewater the cellular biomass on the surface 7 and scrape the cellular biomass from the surface 7, respectively. When the gas in the headspace 4 has been processed to a desired extent, the gas can be released from the headspace 4 through the headspace outlet port 10 and replaced with gas via the first intake port 8. When the liquid in the reservoir 5 has been processed to a desired extent, the liquid in versions as shown in FIG. 1A can be released from the reservoir 5 through the reservoir outlet port 11 and replaced with liquid via the second intake port 9. The released liquid can be recycled to the second intake port 9 and/or used for downstream purposes. The system 1 can operate in a batch or continuous manner.

A preferred use of the system 1 is for processing gases containing methane and/or carbon dioxide (such as biogas or natural gas) and wastewaters (such as wastewaters containing high levels of inorganic nitrogen and/or inorganic phosphorus) in a cellular coculture containing a methanotroph and a phototroph (such as a photoautotroph). The gas and wastewater can be sourced from an anaerobic digester, or any other source. The methanotroph consumes methane present in the sourced gas and produces carbon dioxide for phototroph growth. The phototroph consumes carbon dioxide from sourced gas and produced by the methanotroph and produces oxygen for methanotroph growth. Both the methanotroph and the phototroph consume nutrients present in the wastewater, such as inorganic nitrogen and inorganic phosphorus, for anabolic growth.

The culturing of the invention preferably produces a processed gas (gas reacted in the headspace 4 and/or exiting through the headspace outlet port 10) from the sourced gas (gas from the gas source 25 and/or passed through the first intake port 8 or otherwise introduced within the inner space 3). In various versions of the invention, an amount of methane by volume in the processed gas is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than an amount of methane by volume in the sourced gas. In various versions of the invention, an amount of carbon dioxide by volume in the processed gas is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than an amount of carbon dioxide by volume in the sourced gas. The systems of the invention can remove up to 100% of the methane and carbon dioxide in the sourced gas without providing an external oxygen supply.

The culturing of the invention preferably produces a processed liquid (liquid reacted in the reservoir 5 and/or exiting through the reservoir outlet port 11) from the sourced liquid (liquid from the liquid source 26 and/or passed through the second intake port 9 or otherwise introduced within the inner space 3). In various versions of the invention, an amount of inorganic nitrogen by mass in the processed liquid is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than an amount of inorganic nitrogen by mass in the sourced liquid. In various versions of the invention, an amount of inorganic phosphorus by mass in the processed liquid is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than an amount of inorganic phosphorus by mass in the sourced liquid. In some versions of the invention, the amount of inorganic nitrogen in the processed liquid is less than about 500 mg/L, less than about 250 mg/L, less than about 100 mg/L, less than about 50 mg/L, less than about 25 mg/L, less than about 10 mg/L, or less than about 5 mg/L. In some versions of the invention, the amount of inorganic phosphorus in the processed liquid is less than about 500 mg/L, less than about 250 mg/L, less than about 100 mg/L, less than about 50 mg/L, less than about 25 mg/L, less than about 10 mg/L, or less than about 5 mg/L.

The systems 1 of the invention can be configured as a solitary system 1 unit or in a multi-system 1 configuration. The systems 1 in the multi-system 1 configuration can be arranged in parallel, in series, or a combination thereof. The parallel arrangement can be useful for high-throughput processing of liquids and gasses. The series arrangement can be useful for removing different components from the liquids and gases, for example, by culturing different cells or combinations of cells and/or culturing under different conditions. The series arrangement can also or alternatively be useful for sequentially removing the same components from the liquids and gases to arrive at low final levels.

The terms "culturing" and "cultivating," and grammatical variants thereof, are used interchangeably herein.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1

Photoautotroph-Methanotroph Coculture—A Flexible Platform for Efficient Biological $CO_2$—$CH_4CO$— Utilization Industrial, municipal, and agricultural waste streams contain stranded organic carbon, which can be converted into biogas through anaerobic digestion. It has been demonstrated that biogas has immense potential as a renewable feedstock for producing high-density fuels and commodity chemicals. However, the utilization of biogas presents a significant challenge due to its low pressure and presence of contaminants such as $H_2S$, ammonia, and volatile organic carbon compounds. To tap into this immense potential, effective biotechnologies that co-utilize both $CO_2$ and $CH_4$ are needed. Using the basic metabolic coupling principles utilized by many natural consortia, we have demonstrated that photoautotroph-methanotroph cocultures offers a flexible and highly promising platform for biological $CO_2$/$CH_4$ co-utilization. In this example, we quantitatively model the growth dynamics of a photoautotroph-methanotroph coculture and present experimental and computational tools that are capable of characterizing the coculture.

Industrial, municipal, and agricultural waste streams containing stranded organic carbon represent a significant and underutilized feedstock to produce fuels and chemicals. Biogas, which contains 50%~70% $CH_4$, 30%~40% $CO_2$ and trace amounts of contaminants such as $H_2S$ and $NH_3$, can be produced during anaerobic digestion of various waste streams. $CO_2$ and $CH_4$ are the two leading greenhouse gases (GHGs) that cause global warming and many detrimental effects to the earth's ecosystem, including climate change. If the anaerobic digestion of waste material happens in an uncontrolled fashion such as in landfill, the produced biogas would be released into atmosphere; at the same time, $CH_4$ is a valuable fuel; if anaerobic digestion happens in a controlled condition such as within an anaerobic digester, the produced biogas can be further processed to generate electricity or simply used for heating.

It has been shown that biogas has immense potential as a renewable feedstock for producing high-density fuels and commodity chemicals. EPA estimates that currently US biogas production potential from animal farms alone is 654 billion cubic feet per year, which could displace 7.5 billion gallon of gasoline (AgSTAR, 2018). However, the utilization of biogas represents a significant challenge due to its low pressure and presence of contaminants such as $H_2S$, ammonia, and volatile organic carbon compounds. As a result, although anaerobic digestion (AD) is a mature technology that can offer significant environmental and social benefits, as well as the enormous energy and economic potential, the deployment of AD is rather limited. For example, As of August 2017, out of 8113 US dairy and swine farms identified by AgSTAR as candidates for profitable AD biogas recovery systems, only 250 (3% of total potential) manure AD biogas recovery systems were in operation (AgSTAR, 2018). In addition, most of the AD produced biogas is currently flared or used for heating/cooking with only a fraction to generate electricity or upgraded to a liquefied transportation fuel. Specifically, among all livestock farms that have AD installed, only ~3% of them use biogas to produce CNG and 30% of them use biogas for electricity generation (Qi et al., 2013). In short, the low value of biogas is the main factor that hinders the wide adoption of AD and exploration of biogas potential as a feedstock for production of high-density fuels and commodity chemicals. To tap into the immense potential of biogas produced from waste streams, effective biotechnologies that can operate at ambient pressure, temperature and are economically viable at small to mid-scale are needed, especially the ones that could co-utilize both $CH_4$ and $CO_2$.

Recent studies have demonstrated that natural microbial communities have developed a highly efficient way to recover the energy and capture carbon from both $CH_4$ and $CO_2$ through metabolic coupling of methane oxidation to oxygenic photosynthesis (Kip et al., 2010; Milucka et al., 2015; Raghoebarsing et al., 2005). This coupling represents a major sink of both $CH_4$ and $CO_2$ at oxic-anoxic interfaces across various aquatic and terrestrial ecosystems, where the methanotrophic activity is fueled by in situ photosynthetic production of $O_2$. Specifically, recent findings suggest that the coupling of methane oxidation (by aerobic methanotroph) and oxygenic photosynthesis (by peat moss or photosynthetic algae) is prevalent in nature (Milucka et al., 2015; Raghoebarsing et al., 2005).

These recent findings suggest that the coculture of photoautotroph and methanotroph presents no only a feasible, but also a highly promising strategy for simultaneous conversion of biogas (both $CO_2$ and $CH_4$) into useful products, including high density fuel, commodity chemicals and animal feed, etc. In fact, such coupling has been partially validated in laboratory settings. (1) It was reported that coculture of *Scenedesmus* sp. (microalgae) and *Methylocystis parvus* (methanotroph) can achieve total microbial conversion of both $CH_4$ (60%) and $CO_2$ (40%) in a synthetic biogas without external $O_2$ supply (van der Ha et al., 2012); (2) coculture of *Synechococcus* PCC 7002 (cyanobacteria) and *Methylomicrobium alcaliphilum* (methanotroph) exhibit robust growth on diverse gas mixtures including raw biogas and synthetic natural gas (Hill et al., 2017); (3) coculture of *Chlorella sorokiniana* (microalgae) and *Methylococcus capsulatus* (methanotroph) can recovery nutrient contained in waste water from a potato processing plant and produce single cell protein as animal feed (Rasouli et al., 2018).

As the very first attempts to explore the potential of photoautotroph-methanotroph for biogas conversion, these published research mainly aimed to demonstrate the feasibility of the coculture for $CO_2/CH_4$ co-utilization, without any efforts to mathematically model the coculture and to examine the potential interactions within the cocultures. In addition, it is important to realize that currently how to effectively characterize the coculture still present significant challenges to such research effort. Specifically, how to track the individual biomass concentration in a mixed culture in real-time is still an unsolved problem; in addition, in the photoautotroph-methanotroph coculture, both strains contribute to the production and consumption of $CO_2$ and $O_2$, which adds additional difficulty to the characterization of the coculture.

Using the principles that drive the natural consortia, we have assembled and investigated several different photoautotroph-methanotroph cocultures that exhibit stable growth under varying substrate delivery and illumination regimes. In addition, we have developed experimental and computation protocols to characterize of the coculture accurately, easily, and frequently. These protocols are the key enables to the quantitative examination of the photoautotroph-methanotroph coculture systems. Finally, we have developed an unstructured kinetic model that can accurately capture the growth of each of the individual strains in the coculture under various growth conditions. In this work, we briefly present our progress in understanding the photoautotroph-methanotroph coculture.

From an engineering perspective, coupling photosynthesis to methanotrophic metabolism offers several advantages for the design of robust microbial catalysts for biogas conversion. For example, exchange of in situ produced $O_2$ and $CO_2$ dramatically reduces mass transfer resistance of the two gas substrates. In situ $O_2$ consumption removes inhibition on photoautotroph and eliminates risk of explosion. Interdependent yet compartmentalized configuration of the coculture offers flexibility and more options for metabolic engineering. FIG. 3 shows that the exchange of the in situ produced $O_2$ and $CO_2$ appears to be a major synergistic interaction between the two strains; in addition, there may be other potential "metabolic links" that could promote or inhibit the growth of the coculture.

However, the synergy caused by substrate exchange could also be achieved through culturing the two strains separately and sequentially (photoautotroph then methanotroph). Therefore, the first question we aimed to answer is the following: are there clear benefits of using the coculture than using single cultures sequentially for biogas conversion. In fact, this is a critical question applicable to any consortia-based biotechnologies, as the operation of the mixed culture can be more challenging than maintaining two single cultures sequentially. To answer this question, we have conducted the comparison experiments for three cases using *Arthrosipira platensis—Methylomicrobium buryatense*—as the model coculture system. Case A is the coculture; Case B is the sequential culture of cyanobacterium followed by methanotroph, with the amount of $O_2$ produced by the cyanobacterium injected into the single culture of methanotroph; Case C simulates the effect of the exchange of in situ produced $O_2$ between the coculture, where the amount of $O_2$ produced by the cyanobacterium in the coculture was injected into the methanotroph single culture.

Figure 5A:
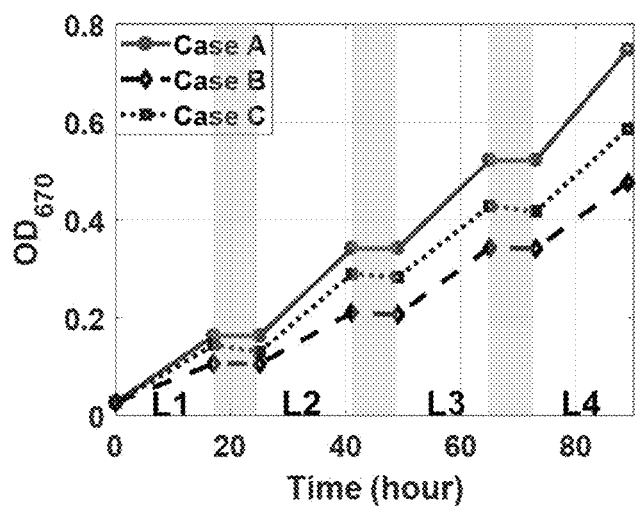
FIGS. 5A-C show results of culturing a methanotroph and microalgae under various conditions. Comparison experiments show that both strains growth much faster in coculture (Case A) than in sequential (Case B) as shown in FIGS. 5A-B.
Figure 5B:
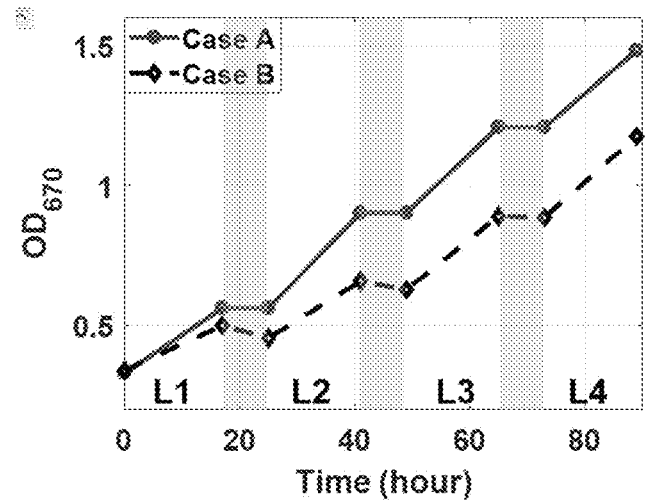
Figure 5C:
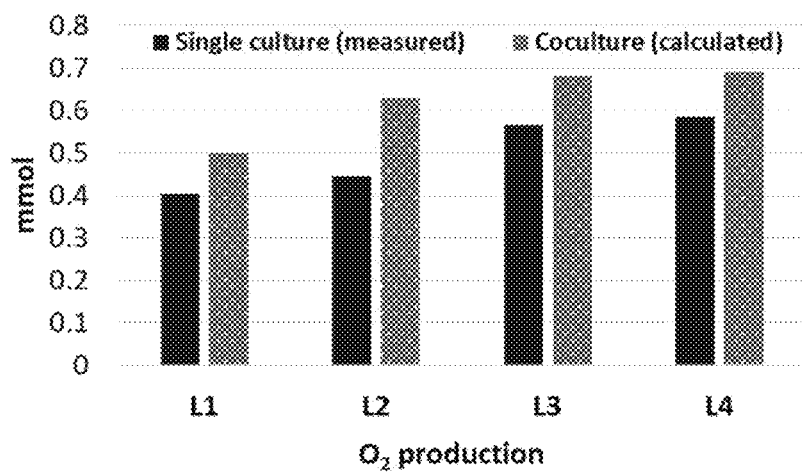

All experiments were carried out in 250 ml serum bottles with 100 ml media under batch operations, with gas phase 70% $CH_4$ and 30% $CO_2$, light:dark cycle of 16:8, and light intensity 180 μmol/m$^2$/s. FIG. 5A compares the methanotroph growth in the three cases over 4 days (4 light periods and 3 dark periods), and FIG. 5B compares the growth of cyanobacterium in case A and B for the same period (as $CO_2$ is available from head space, case C does not apply to cyanobacterium), and FIG. 5C compares the oxygen produced by cyanobacterium in Cases A and B. FIGS. 5A-5C clearly show that both cyanobacterium and methanotroph in coculture (Case A) grew significantly faster than the sequentially operated single cultures (Case B). In addition, the improvement of the methanotroph growth cannot be fully explained by the availability of the extra $O_2$ produced in coculture (Case C). FIGS. 5B and 5C further confirmed that cyanobacterium in the coculture grow faster than the single culture and produce more $O_2$. Together, FIGS. 5A-5C suggest that there could be other factors that promote cell growth of both strains in the coculture; in other words, the photoautotroph-methanotroph coculture offer significantly more benefit than sequentially operated single cultures.

Characterization of the coculture: Multispecies associations are ubiquitous in nature as they provide key ecosystem services such as carbon, nutrient, and metal cycling. It has been recognized that a mixed culture could offer a number of advantages over a conventional single-culture, such as complete utilization of substrate, better stability and robustness, higher product yield, higher growth rate, as well as the capability to carry out multistep transformation that would be impossible for a single organism. Despite these potential significant advantages, utilization of mixed cultures for biotechnological applications in bioenergy and related areas have been limited partially due to the methodological gaps. Specifically, the methodological gap refers to the lack of effective, fast, and low-cost analytical tools to characterize mixed culture systems frequently or in real-time. In this section, we report the experimental and computational protocols we developed to quantitatively characterize the photoautotroph-methanotroph coculture.

Accurate measurement of overall consumption and production rate for $CH_4$, $O_2$ and $CO_2$: Due to gas phase volume/pressure (for batch experiments) or flow rate (for continuous experiments) change, and the pH dependent solubility of $CO_2$, using the direct GC measurements of the headspace or off-gas composition to calculate the gas consumption/production rates can cause large errors. To address these challenges, we have developed two easy-to-implement experimental protocols and associated calculation procedures to obtain accurate measurements of gas component consumption and production rates for batch and continuous bioconversion. For depressurized (i.e., system pressure below 1 atm) batch cultures, we use nitrogen (or other inert gases) to re-pressurize the system to 1 atm before taking sample; while for continuous cultures, we use helium (or other inert gases) as an internal tracer to accurately measure off-gas flow rate. The effectiveness and accuracy of the two protocols and associated calculation procedures were demonstrated using several case studies with both abiotic and biotic systems. For different methanotroph cultures (both batch and continuous experiments), the overall carbon balance was consistently around 98% to 102%, indicating highly reliable and accurate measurements of different gas consumption and production rates (Stone et al., 2017). Details of the measurement protocols and computation procedures can be found in (Stone et al., 2018).

Figure 6A:
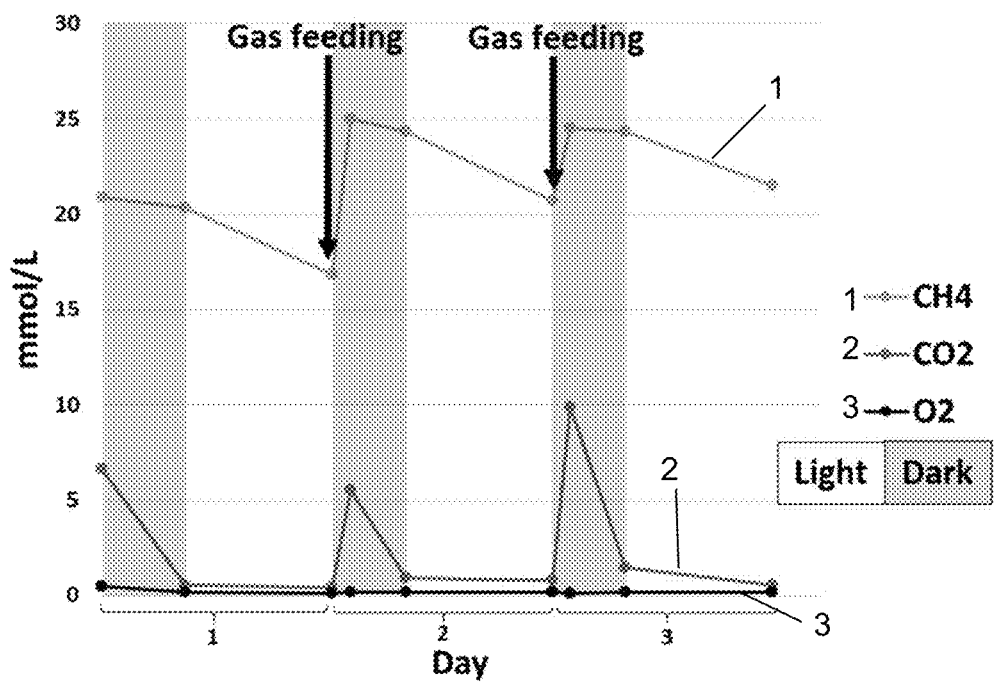
FIGS. 6A-D show gas phase measurement over time (FIG. 6A), individual consumption/production (estimated) and overall change (measured) of $O_2$ (FIG. 6B), and $CO_2$ (FIG. 6C) for photoautotroph-methanotroph coculture during three light cycles. The results are validated by the good agreement between the estimated and measured total biomass during the same cycles (FIG. 6D).
Figure 6B:
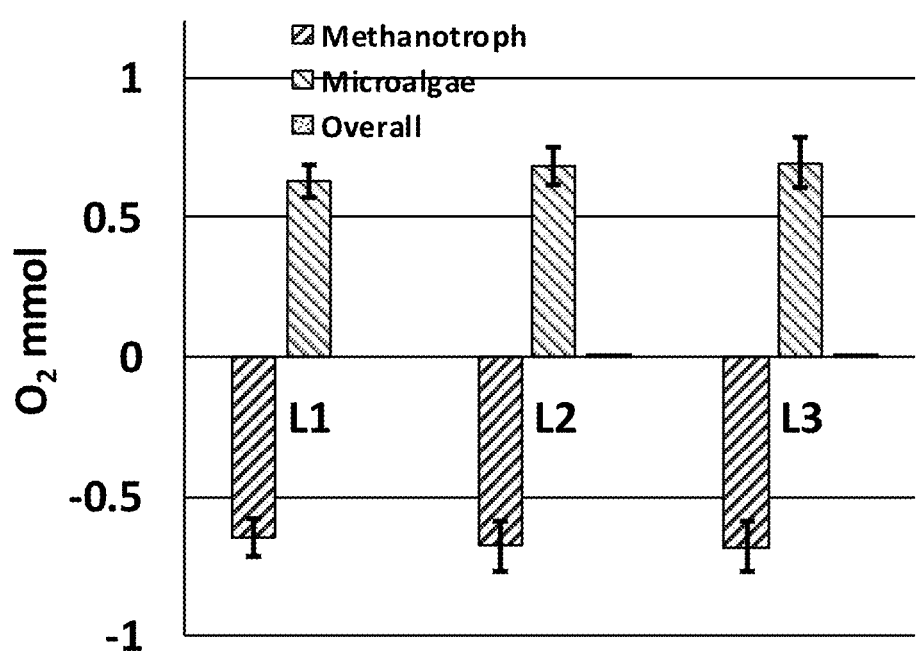
Figure 6C:
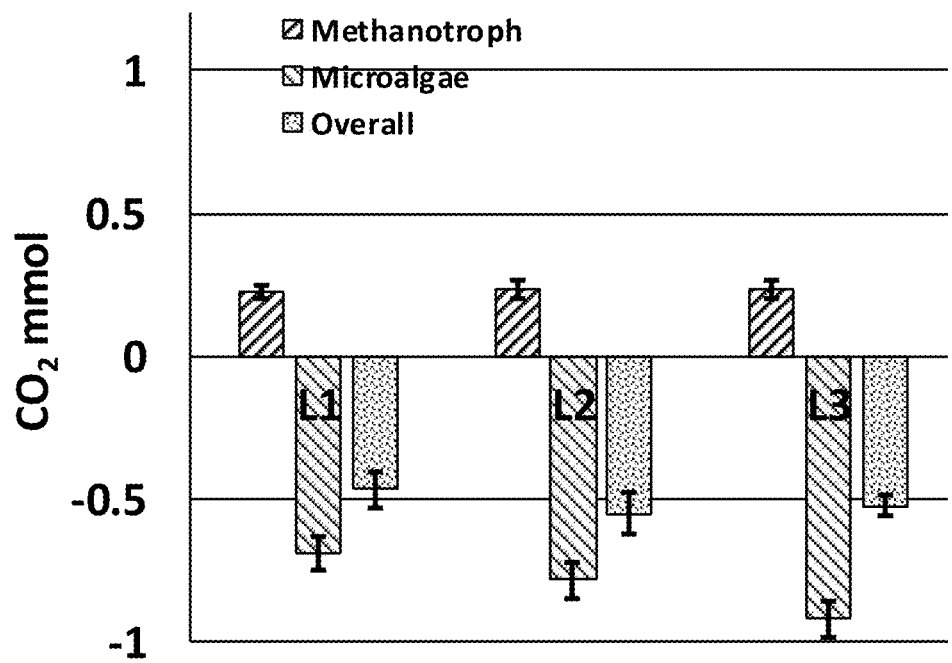
Figure 6D:
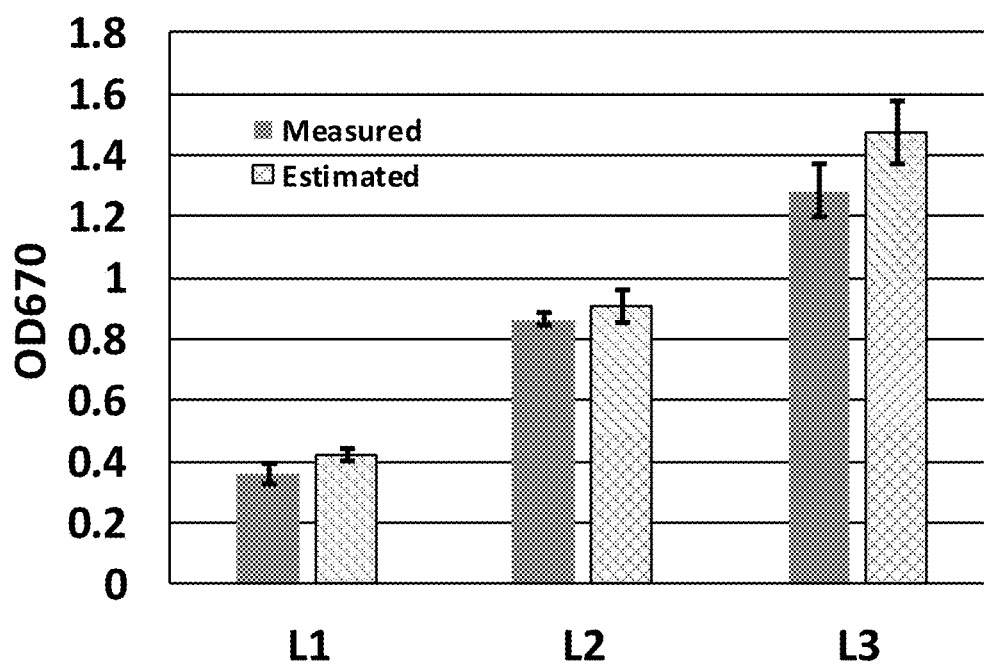

Estimate individual gas consumption and production rates by each organism: Estimating individual consumption/production rate of metabolites that are produced or consumed by multiple species has been challenging. However, in order to better understand the dynamics of the coculture, it is necessary to track how much $CH_4$, $O_2$ and $CO_2$ are consumed or produced by each organism. It should be noted that the individual consumption/production rate of $CO_2$ and $O_2$ cannot be measured directly because of the coupling between photoautotroph and methanotroph. In addition, the amount of dissolved $CO_2$ in the liquid medium has to be considered due to its high solubility. To address this challenge, we have developed a computational procedure based on mass balances and growth stoichiometric information (such as biomass yield) to compute the amount of $O_2$ and $CO_2$ consumed or produced by each organism as shown in FIG. 4. To examine the accuracy of the procedure, we compared the total biomass estimated through the procedure with measured total biomass for multiple light cycles. FIG. 6A shows the gas phase measurements over time, and FIG. 6D shows the estimated vs. measured total biomass. The good agreement between the estimates and measurement suggests that the procedure will yield meaningful and reliable track of $CO_2$ and $O_2$ consumption and production rates.

Kinetic modelling of the coculture: The development of multi-organism platforms for commercial biogas conversion present significant challenges which center around our ability to control function and composition of species in the coculture. An essential tool for the optimization, design, and analysis of the coculture based biogas conversion is the development and validation of kinetics models that can accurately describe and predict the coculture growth under different conditions. In this work, we present an unstructured dynamic model we recently developed to capture the growth dynamic of the coculture under wide culture conditions.

The unstructured kinetic model: Monod model is most commonly applied to describe cell growth for single cultures, where substrate uptake is described by conventional Michaelis-Menten kinetics ($[S]/K_s+[S]$. However, Michaelis-Menten kinetics has its limitation, particularly for mass transfer limited processes such as the case of gas phase substrate. When mass transfer is the limiting step, the concentration of the dissolved substrate would become zero, as substrates transferred into the culture broth would be consumed by the cells. If Michaelis-Menten kinetics is utilized, the predicted cell growth rate would be zero because $[S]=0$. Substrate update is even more complex for the coculture system, as in situ produced $CO_2$ and $O_2$ would be consumed first due to minimum mass transfer resistance. To capture such effective, we derived the following substrate uptake. For the photoautotroph, the specific $CO_2$ uptake is:

$$q^A_{CO2} = \max \begin{cases} \frac{v^A_{max}[CO2]}{K_{mA} + [CO2]} \\ \frac{1}{Y^M_{X/CO2}} \mu^M \end{cases};$$

For the methanotroph, the specific $O_2$ uptake is:

$$q^M_{O2} = \max \begin{cases} \frac{v^M_{max}[O2]}{K_{mM} + [O2]} \\ \frac{1}{Y^A_{X/O2}} \mu^A \end{cases},$$

Where the notations are listed in Table 1. It should be pointed out that at the beginning of the experiment, there is no $O_2$ in the head space, and methanotroph will have to rely on photoautotroph produced $O_2$ to grow.

TABLE 1

Notations used in models.

| Parameter | |
|---|---|
| $\mu^A$ | Specific growth rate for photoautotroph |
| $\mu^M$ | Specific growth rate for methanotroph |
| $\mu_{max}^A$ | Maximum growth rate for photoautotroph |
| $K_{SA}$ | Half-substrate saturation constant for carbon dioxide |
| $\mu_{max}^M$ | Maximum growth rate for methanotroph |
| $K_{SM}$ | Half-substrate saturation constant for oxygen |
| $K_{SCM}$ | Half-substrate saturation constant for methane |
| $[O_2], [CH_4], [CO_2]$ | Substrate concentration |
| $v_{max}^A$ | Maximum uptake rate for carbon dioxide |
| $v_{max}^M$ | Maximum uptake rate for oxygen |
| $v_{Mmax}^M$ | Maximum uptake rate for methane |
| $K_{mA}$ | Uptake half-saturation constant for carbon dioxide |
| $K_{mM}$ | Uptake half-saturation constant for oxygen |
| $K_{mMM}$ | Uptake half-saturation constant for methane |
| $Y_{X/CO2}^M$ | Yield coefficient for carbon dioxide |
| $Y_{X/O2}^A$ | Yield coefficient for oxygen |
| $Y_{X/CH4}^m$ | Yield coefficient for methane |
| $q_S^{A,M}$ | Specific substrate uptake rate |
| $X^M$ | Biomass concentration for methanotroph |
| $X^A$ | Biomass concentration for photoautotroph |
| $k_l a$ | Volumetric liquid phase mass transfer coefficient |
| $C^*$ | Dissolved substrate concentration at saturation |
| $I_0$ | Incident light intensity |
| m | Light intensity parameter |
| $I_a$ | Attenuated light intensity |
| $K_{SI}$ | Half-light saturation constant |

With individual cell specific growth rate determined, the rest of the equations for the coculture dynamic model is similar to that of single batch cultures, except that the equation for dissolved substrate concentration should include the contributions from both strains.

For photoautotroph biomass:

$$\frac{dX^A}{dt} = \mu^A X^A$$

For methanotroph biomass:

$$\frac{dX^M}{dt} = \mu^M X^M$$

For different dissolved gas components:

$$\frac{d[CO2]}{dt} = k_l a(C^* - [CO2]) - q^A_{CO2} X^A + \frac{1}{Y^M_{X/CO2}} \mu^M X^M$$

$$\frac{d[CH4]}{dt} = -q^M_{CH4} X^M + k_l a_{CH4}(C^* - [CH4])$$

$$\frac{d[O2]}{dt} = -q^M_{O2} X^M + \frac{1}{Y^A_{X/CO2}} \mu^A X^A$$

Figure 7:
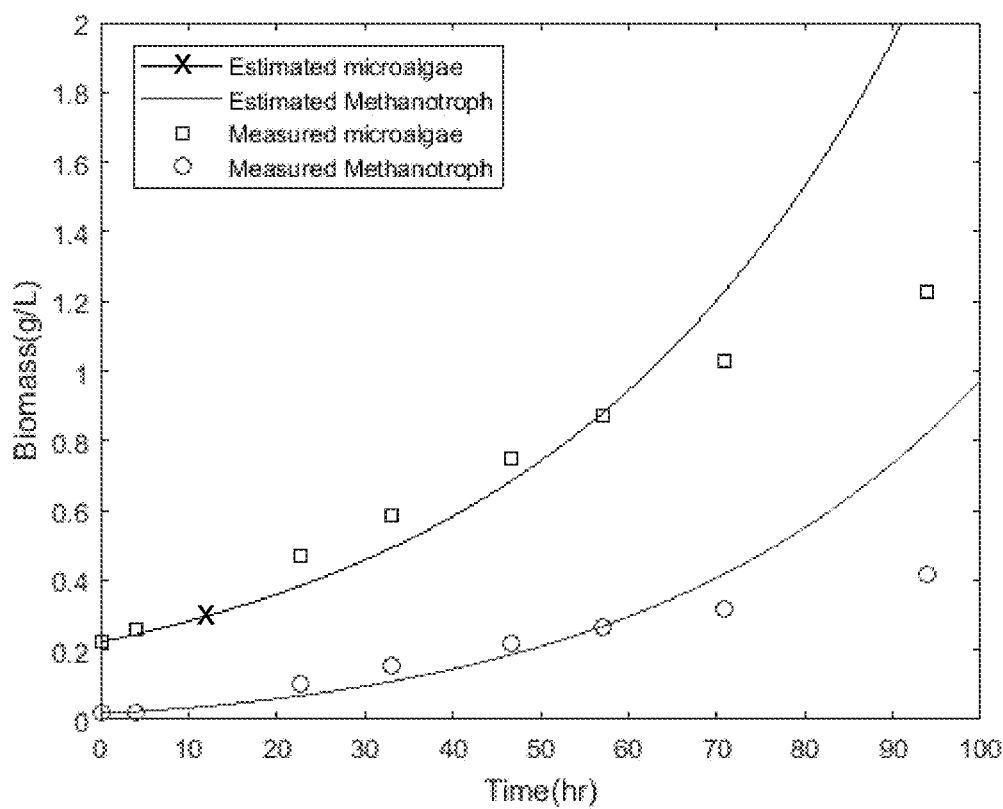
FIG. 7 shows a comparison of model-predicted biomass concentration with measured biomass concentration in methanotroph-microalgae coculture.

When these set of equations are applied to fit the experimental data, it did a reasonably good job in capturing the coculture growth. Using *Arthrosipira platensis—Methylomicrobium buryatense* as the model coculture system, we conducted experiment with continuous illumination for different light intensities. The model fitting results are shown in FIG. 7 for light intensity of 140 μmol/m²/s. The model predicted biomass concentration for each individual strain agree with the trend of the measurement well, particularly for the condition where biomass concentration is not high.

Effect of self-shading on light intensity: The growth of photoautotroph depends on the light intensity, in the models presented above, the effect of the light intensity was lumped into the maximum cell growth rate $\mu^A_{max}$ which is fixed during the whole batch. However, the effect of light intensity depends on the biomass concentration due to the "self-shading" effect (Béchet et al., 2013), which varies throughout the whole batch. To capture such self-shading effect, we modified the Monod model for cell growth rate to the following:

$$\mu^A = \mu^A_{max} q_{[CO2]} \cdot \frac{I_a}{K_{SI} + I_a}$$

where $I_a$ is attenuated light intensity in the coculture system and can be estimated by Beer-Lambert law for light distribution:

$$I_a = I_0 \exp(-mX); X=(X^A+X^M), m=(al_0+b)$$

Figure 8:
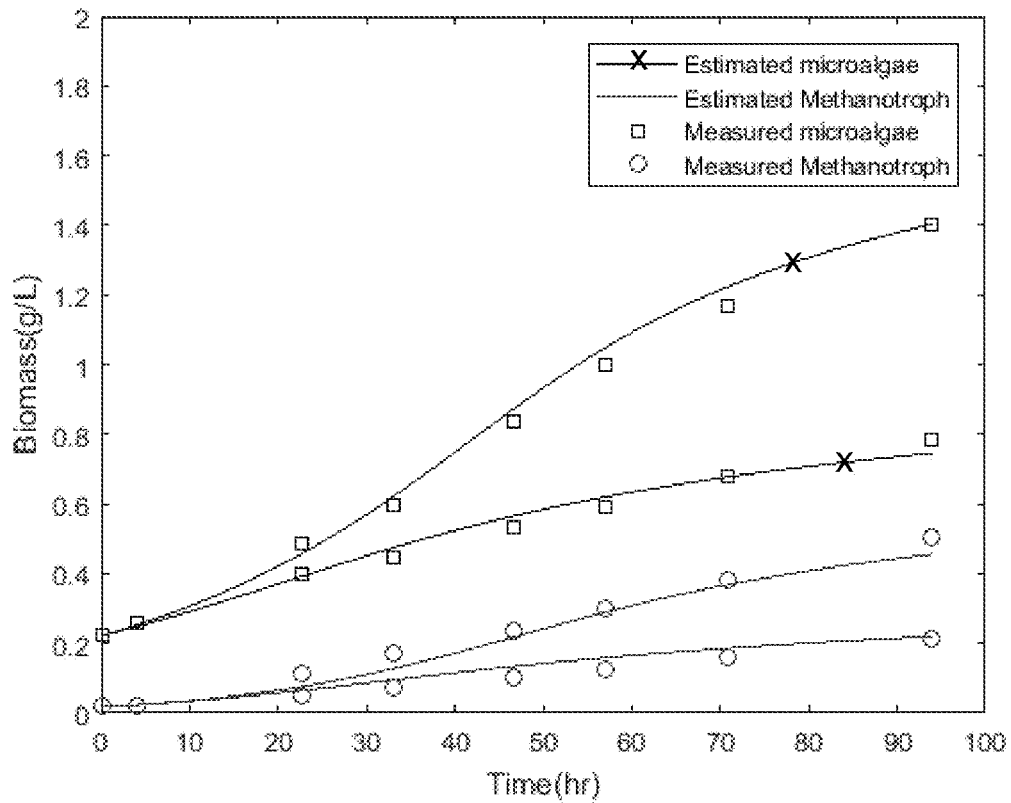
FIG. 8 shows a comparison of alternative model-predicted biomass concentration with measured biomass concentration in methanotroph-microalgae coculture.

FIG. 8 compares the biomass concentration of each strain in the coculture predicted by the modified model with experimental measurements for both 60 and 180 μmol/m²/s. As shown in FIG. 8, by considering the self-shading effect, the modified model was able to capture the coculture growth dynamic accurately throughout the whole batch.

In this experiment, through designed experiments, we demonstrated that besides the synergy due to the exchange of in situ produced $O_2$ and $CO_2$ in a photoautotroph-methanotroph coculture, there exist other "metabolic links" that could further stimulate the growth of both strains in the coculture, and offer significantly more benefit than sequentially operated single cultures. In addition, we have developed necessary experimental and computational protocols to effectively and accurately characterize the photoautotroph-methanotroph coculture, including tracking the individual biomass concentrations in the coculture, estimating individual gas ($O_2$ and $CO_2$) consumption and production rates of each strain from the measured total gas consumption and production rates. Finally, we have developed an unstructured kinetic model to capture the dynamics of the coculture growth. By considering the exchange of in situ produced $O_2$ and $CO_2$, as well as coculture's "self-shading" effect on light intensity, the unstructured model was demonstrated to accurately capture the growth of each strain in the coculture under different culture conditions.

These recent developments laid the foundation for further investigation of the photoautotroph-methanotroph coculture, such as developing a genome-scale metabolic model for the coculture, and identification of potential interactions or "metabolic links" at molecular level, which will enable the further metabolic engineering of the coculture platform for commercial biogas conversion.

Example 2

A Microalgae-Methanotroph Coculture Platform for Fuels and Chemical Production from Wastewater Summary Wastewater resource recovery facilities are major energy consumers in a community, as well as major contributors for greenhouse gas (GHG) emission. Although anaerobic digestion (AD) is widely employed in wastewater treatment to reduce the amount of solid organic waste and the sludge produced, the use of the produced biogas is mostly limited to heating and electricity generation, while the nutrient rich digestate still requires further treatment. In this work, we propose a waste-to-value (W2V) platform based on a microalgae-methanotroph coculture, which can convert AD-generated biogas into value-added products, while simultaneously removing nutrients from digestate. The coculture platform explores the synergistic interactions within a microalgae-methanotroph coculture to achieve significantly improved productivity of microbial biomass and enhanced nutrient recovery performance. Using *Chlorella sorokiniana*—*Methylococcus capsulatus* (Bath) as the model coculture, we demonstrate that the coculture offers a highly promising platform for W2V technologies, which can efficiently recover energy (from $CH_4$) and carbon (from both $CH_4$ and $CO_2$) to produce microbial biomass, while removing nutrients from wastewater to produce treated clean water. Specifically, the coculture could achieve zero GHG emission without external supply of oxygen, as well as complete removal of inorganic nitrogen and phosphorus from AD effluent. Finally, the potential applications of the wastewater-derived coculture biomass are discussed.

Introduction

Municipal, agricultural, and industrial processes generate large volumes of wastewater that are rich in nitrogen, phosphorus, and other nutrients. If not properly treated before released into waterways, wastewater can have detrimental impacts on the local community and environment. In fact, the excessive amount of nitrogen and phosphorus in released wastewater has caused increasingly negative consequences to our ecosystems and public health, including worsening of the greenhouse effect, reduction of the protective ozone layer, adding to smog, contributing to acid rain, and contaminating drinking water (Driscoll et al., 2003; Galloway et al., 2004). At the same time, wastewater contains stranded organic carbon, which represents a significant and underutilized feedstock to produce fuels and chemicals. If wastewater treatment can be integrated with producing value-added products, it will not only reduce the detrimental environmental and social impact of wastewater, but also generate revenue to offset the cost of wastewater treatment and even make the process profitable. As a result, waste-to-value (W2V, e.g., waste-to-energy, waste-to-fuel, waste-to-chemical, etc.) technologies have drawn increasing research attention in the last few decades (Fei et al., 2014; Haynes and Gonzalez, 2014; Henard et al., 2016). However, to date, the only notable commercialized W2V process at scale is anaerobic digestion (AD) which converts organic waste into biogas.

Currently, using AD to convert the stranded organic carbon in wastewater to biogas has been well-recognized and broadly adopted by municipal wastewater resource recovery facilities (WRRFs), particularly large scale WRRFs. In fact, 48% of total municipal wastewater flow in the US is treated by AD (Qi et al., 2013), which corresponds to 1,484 of the 14,780 WRRFs in the US. AD is a commercially proven technology, and arguably the most efficient solution for handling organic waste streams. During the AD process, a large fraction of organic matter is broken down into biogas (50-70% $CH_4$, 30-50% $CO_2$, with trace amounts of other gases such as $H_2S$ and $NH_3$). Treating wastewater with AD offers many advantages including: 1) macronutrients (e.g., nitrogen, phosphorus, potassium, etc.) are transformed into more easily treatable forms which can significantly reduce their environmental impacts; 2) containment of the greenhouse gases (GHGs) as biogas ($CH_4$ and $CO_2$), which not only reduces GHGs emission, but also provides a valuable fuel; 3) effective pathogen (>95%) and odor mitigation (Angelidaki and Ellegaard, 2003; Nasir et al., 2012). However, the low pressure and impurities ($CO_2$, $NH_3$ and $H_2S$ etc.) in biogas limit the utilization of biogas to heating and electricity generation. In addition, due to the cost associated with cleaning and upgrading biogas, AD installation is currently limited to large-scale WRRFs.

At the same time, the liquid effluent of AD (i.e., digestate) contains high concentrations of ammonia and orthophosphate which must be removed by the treatment plant prior to discharge. In WRRFs with AD installed, the nutrient-rich digestate is returned to a biological nutrient removal unit for further treatment. Biological nutrient removal is achieved through the so-called nitrification-denitrification process, where ammonia is converted to dinitrogen gas by activated sludge. However, the nitrification process requires large energy input to provide oxygen to the activated sludge, and the denitrification process often requires supplementation of an organic carbon source (e.g., methanol) to support nitrate reduction. Pumping air and supplying organic carbon sources are the primary contributors to high operational costs for WRRFs.

To address the limitations associated with AD-based W2V technology, we propose a sustainable biological platform to convert AD-produced biogas into value-added products, while simultaneously recovering nutrients (e.g., N and P) from the AD effluent. The proposed platform explores the synergistic interactions within a microalgae-methanotroph coculture to achieve significantly improved productivity of microbial biomass and enhanced nutrient recovery performance. As shown in FIG. 3, through the interspecies coupling of methane oxidation to oxygenic photosynthesis, the microalgae-methanotroph coculture offers several advantages for biogas conversion: (1) exchange of in situ produced $O_2$ and $CO_2$ dramatically reduces mass transfer resistance of the two gas substrates; (2) in situ $O_2$ consumption removes inhibition on microalgae and eliminates/reduces the risk of explosion; (3) potential interspecies metabolic links could significantly enhance the growth of both strains in the coculture. In this work, using *Chlorella sorokiniana*—*Methylococcus capsulatus* (Bath) as the model coculture, we demonstrate that the microalgae-methanotroph coculture offers a highly promising platform for W2V technologies, which can efficiently recover energy (from $CH_4$) and carbon (from both $CH_4$ and $CO_2$) to produce microbial biomass, while removing nutrients from wastewater to produce treated clean water. The wastewater-derived microbial biomass can serve as raw material to produce an array of value-added products, including animal feed, biocrude and bioplastics. Furthermore, through the metabolic coupling of methane oxidation and oxygenic photosynthesis, we could achieve zero GHG emissions without external supply of oxygen, as well as complete removal of inorganic nitrogen and phosphorus from AD effluent.

Materials and Methods

Wastewater collection and pretreatment: Municipal wastewater was collected from Columbus Water Works, a water resources facility in Columbus, Ga. This facility treats an average of 45 million gallons of wastewater per day from homes, businesses, and industries. Anaerobic digestate samples were collected in clean plastic containers from the mesophilic digester #2 through sampling ports. Secondary clarifier effluent (CLE) was also collected from the top of clarifier #2 (water before chlorination and discharge into river). Wastewater samples were stored on ice for transportation to the lab where samples were frozen at −20° C.

Before each experiment, wastewater samples were thawed, and three different pretreatment methods were tested in this work—settled (S), filtered (F) and autoclaved (A). For settled samples, the thawed wastewater sample was set aside in refrigerator for 24 hours to allow the solid fraction to settle down, and the top liquid phase was decanted for experiments; for filtered samples, the settled wastewater sample was filtered through a 0.2 μm filter (nylon, VWR) to remove most bacteria and small floating particles; for autoclaved samples, the filtered wastewater sample was further autoclaved to completely remove any bacteria contained in the digestate.

Precultures of the methanotroph and microalga: Cultures of $M.$ $capsulatus$ and $C.$ $sorokiniana$ were grown in 250 mL serum bottles sealed with a septum and aluminum cap. Pre-cultures of both strains were maintained on autoclaved anaerobic digestate diluted with the secondary clarifier effluent to ensure sterile monocultures. For methanotrophic growth, methane was supplied to a final concentration of 70% (v/v) $CH_4$ and 30% (v/v) $O_2$ and placed in a rotary shaker set at 200 rpm and 37 ° C. C. sorokiniana was also grown on the wastewater media and carbon dioxide was supplied to a final concentration of 30% (v/v) $CO_2$ and 70% (v/v) $N_2$. The vials were placed in a rotary shaker set at 200 rpm, 37° C. and were cultivated under continuous illumination at 200 μmol m$^{-2}$ s$^{-1}$.

Coculture growth on differently diluted AD effluent: Due to the high ammonia concentration and other potential inhibitors in the AD effluent, dilution of the AD effluent is necessary for microalgae and coculture-based wastewater treatment. This set of experiments were performed to investigate the effect of different diluents. In this work, three diluents were examined for their effect on coculture growth: (1) tap water (TW), (2) secondary clarifier effluent (CLE) and (3) a modified ammonium mineral salts medium (AMS), which is the standard AMS medium (Whittenbury et al., 1970) without $NH_3$—N and $PO_4^{3-}$—P. The coculture mediums were prepared by diluting the settled AD effluent ~6 times using the different diluents to a final $NH_3$—N concentration of 120 mg/L $NH_3$—N. These mediums are denoted as AD-TW, AD-CLE and AD-AMS.

Cocultures were grown in 250 mL serum bottles sealed with a septum and aluminum cap with the differently diluted AD effluent mediums as culture media. Cells were inoculated at a 3:1 ($C.$ $sorokiniana$:$M.$ $capsulatus$) ratio based on the optical density (OD) measured at 750 nm. In each vial, the initial OD for $C.$ $sorokiniana$ was 0.6 and the initial OD for $M.$ $capsulatus$ was 0.2. Synthetic biogas (70% $CH_4$, 30% $CO_2$) was used as carbon substrate and sparged through the medium for 10 minutes. The serum bottles were placed on a rotary shaker set at 200 rpm and 37° C. with continuous illumination at 200 μmol m$^{-2}$ s$^{-1}$. After inoculation, both liquid and gas samples were taken once per day to measure total OD (Beckman Coulter DU Life Science UV/Vis spectrophotometer) and gas composition (Agilent 7890B with FID, TCD, Unibeads IS 60/80 mesh and MolSieve 5A 60/80 SST columns) following an established protocol (Stone et al., 2019). To track the amount of $CO_2$ dissolved in liquid phase, total inorganic carbon (TIC) of the liquid samples were also analyzed (Shimadzu TOC-VCSN analyzer). Individual biomass concentrations were determined based on an established protocol (Badr et al., 2019). Finally, ammonia-nitrogen ($NH_3$—N) and orthophosphate ($PO_4^{3-}$—P) were measured using Hach kits (Hach company, USA).

Coculture growth on differently pretreated AD effluent diluted by CLE: To investigate the effects of different wastewater pretreatment methods on the growth of the coculture, AD effluent diluted with CLE was used as the culture medium. Both the AD effluent and CLE were pretreated by three methods (settled, filtered, and autoclaved) as described in "Wastewater collection and pretreatment". All pretreated AD effluent was diluted using CLE pretreated by the same method to a final NH3-N concentration of 120 mg/L. Cells were inoculated at a 3:1 ($C.$ $sorokiniana$:$M.$ $capsulatus$) ratio based on the optical density at 750 nm. Synthetic biogas (70% $CH_4$, 30% $CO_2$) was sparged through the medium for 10 minutes. Bottles were placed on a rotary shaker set at 200 rpm and 37° C. with continuous illumination at 200 μmol m$^{-2}$ s$^{-1}$. After inoculation, both liquid and gas samples were taken once per day to measure total OD, gas composition, and individual biomass composition.

Assessing carbon recovery without nutrient limitation: These experiments were performed to assess the potential of the coculture for complete carbon recovery from biogas when unlimited nutrients were available. In addition, the coculture performance was compared with sequential single culture, i.e., $C.$ $sorokiniana$ followed by $M.$ $capsulatus$. For this experiment, each 250 mL serum bottle started with 100 mL of the filtered AD effluent diluted 5 times with CLE. The feed gas composition of the coculture was 70% $CH_4$, 30% $CO_2$ while the single cultures feed gas compositions were 70% $N_2$, 30% $CO_2$ for $C.$ $sorokiniana$ and 70% $CH_4$, 30% $N_2$ for $M.$ $capsulatus$. Every 24 hours, the total amount of $O_2$ produced by the single cultures of $C.$ $sorokiniana$ was determined and injected into each vial of $M.$ $capsulatus$ single culture. As a result, the inoculation of $M.$ $capsulatus$ vials occurred 24 hours after the $C.$ $sorokiniana$ vials. The initial inoculum concentrations for each strain in the coculture were the same as that for each single culture; $OD_{750}$ 0.2 for $M.$ $capsulatus$ and $OD_{750}$ 0.6 for $C.$ $sorokiniana$. 48 hours after inoculation, 20 mL of undiluted, filtered AD effluent was added to the bottle to prevent nutrient limitation. After inoculation, both liquid and gas samples were taken once per day to measure total $OD_{750}$, gas composition and individual biomass concentration.

Assessing nutrient recovery by the coculture: These experiments were performed to assess the potential of the coculture for nutrient recovery from wastewater. Similarly, the coculture performance was compared with sequential single culture, i.e., $C.$ $sorokiniana$ followed by $M.$ $capsulatus$. For this experiment, each 250 mL serum bottle started with 100 mL of the filtered AD effluent diluted 5 times with CLE; the feeding gas for the coculture and two single cultures was the same as that in "Assessing carbon recovery without nutrient limitation", so were the initial inoculum concentrations. After inoculation, both liquid and gas samples were taken once per day to measure total OD, gas composition, and individual biomass composition. In addition, to quantify the change in concentrations of the nutrients in the liquid medium, total nitrogen (TN), ammonia-nitrogen ($NH_3$—N), total phosphorus (TP) and orthophosphate ($PO_4^{3-}$—P) were all measured using Hach kits. Liquid samples were centrifuged at 12,000 rpm for 4 mins then filtered (0.2 μm) before analyzing using the Hach kits. Percent nutrient recovery (R) was calculated using the following equation:

$$R = \frac{C_0 - C_f}{C_0} * 100\% \quad (1)$$

Where $C_0$ and $C_f$ are the initial and final nutrient concentrations of NH3-N, $PO_4^{3-}$—P, TN, or TP, respectively.

Data analysis and statistics: All experiments were performed in triplicate. Analysis and standard deviation calculations were performed in Microsoft Excel. One-way ANOVA and Tukey HSD tests were performed in R using the 'multcomp' and 'agricolae' packages at a significance level of α=0.05.

Results

Coculture growth on differently diluted AD effluent: AD effluent often contains various inhibitors, including volatile fatty acids and antibiotics that may severely inhibit the growth of both microalgae and methanotroph in the coculture. For microalgae-based wastewater treatment, the digestate is usually diluted 10 or 20 times to achieve sustained growth of microalgae and enable sufficient nutrient removal rates (Xia and Murphy, 2016; Wen et al., 2017; Wang et al., 2018). However, using freshwater to dilute AD effluent is not practical because freshwater is a limited resource in most locations. In this work, we examine the feasibility of using secondary clarifier effluent (CLE) as a diluent in the proposed coculture technology. The growth performance of the coculture on AD effluent diluted with CLE is compared with that on AD effluent diluted with tap water (TP) and AMS medium (AMS) to determine its feasibility.

Figure 9A:
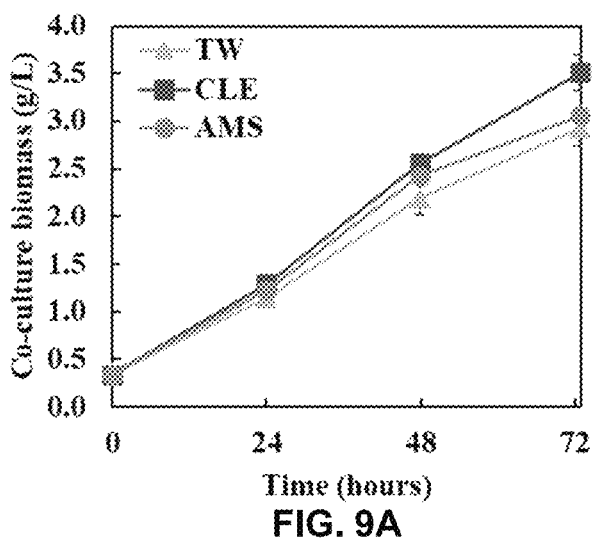
FIGS. 9A-9C show growth profiles of *M. capsulatus* and *C. sorokiniana* cocultures on anaerobic digestate diluted with tap water (AD-TW), anaerobic digestate diluted with secondary clarifier effluent (AD-CLE), and anaerobic digestate diluted with a modified ammonium mineral salts medium (AD-AMS).
Figure 9B:
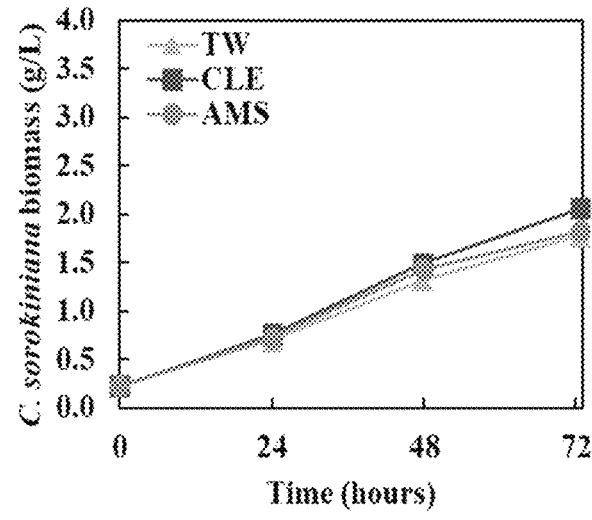
Figure 9C:
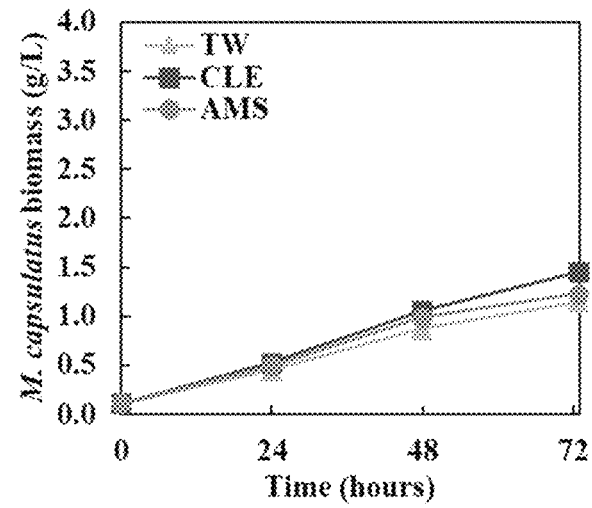

The coculture performance was evaluated by biomass production, biogas utilization and nutrient recovery. The biomass profiles of the coculture over the 72 hour cultivation period are plotted in FIGS. 9A-9C, which show the biomass concentration of the coculture, as well as the calculated concentration of C. sorokiniana and M. capsulatus in the coculture obtained on AD-TW, AD-CLE and AD-AMS. This experiment clearly demonstrates the feasibility of using CLE as diluent: the coculture growth on AD-CLE exhibited the best growth performance compared to those on AD-TW and AD-AMS. The final biomass concentration of the coculture grown on AD-CLE was 3.51±0.19 g/L, which is higher than that of AD-TW (2.93±0.19 g/L, with a p-value of 0.009) and AD-AMS (3.06±0.01 g/L, with a p-value of 0.029). This result suggests that the minerals and other microorganisms present in the AD effluent and CLE might be beneficial to the coculture, which is in agreement with previous studies (Tandon and Jin, 2017; Toyama et al., 2018; Lee et al., 2019; Qu et al., 2019).

Figure 10A:
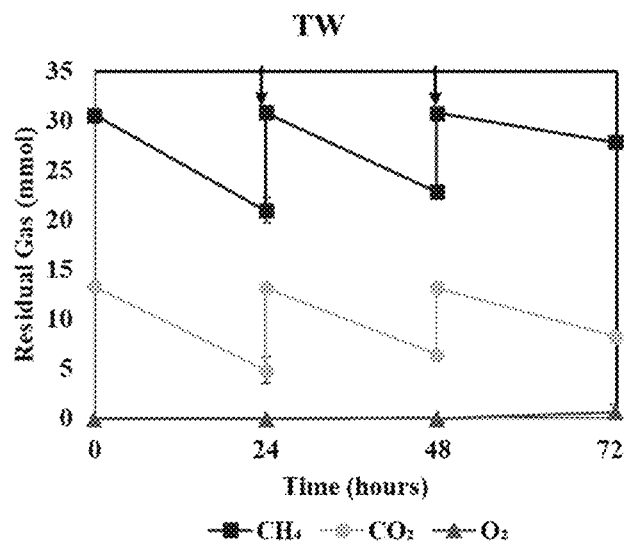
FIGS. 10A-10C show the headspace composition for *M. capsulatus* and *C. sorokiniana* cocultures grown on anaerobic digestate diluted with tap water (AD-TW) (FIG. 10A), anaerobic digestate diluted with secondary clarifier effluent (AD-CLE) (FIG. 10B), and anaerobic digestate diluted with a modified ammonium mineral salts medium (AD-AMS) (FIG. 10C), reveals similar gas consumption performance among the different diluted digestates. Arrows indicate the points at which each bottle was refed with synthetic biogas.
Figure 10C:
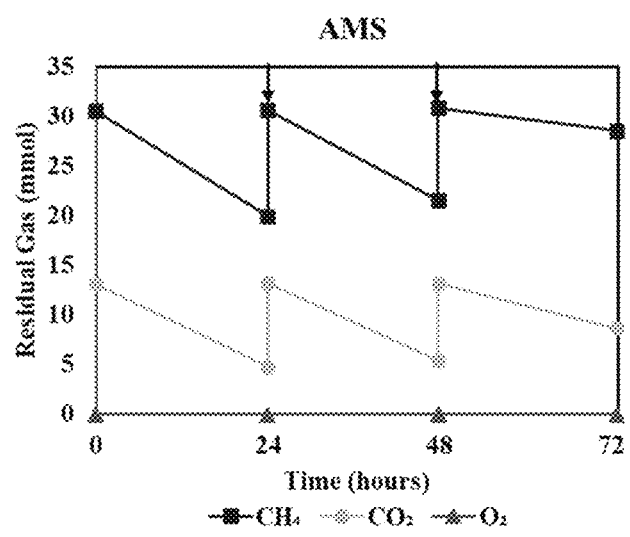
Figure 10B:
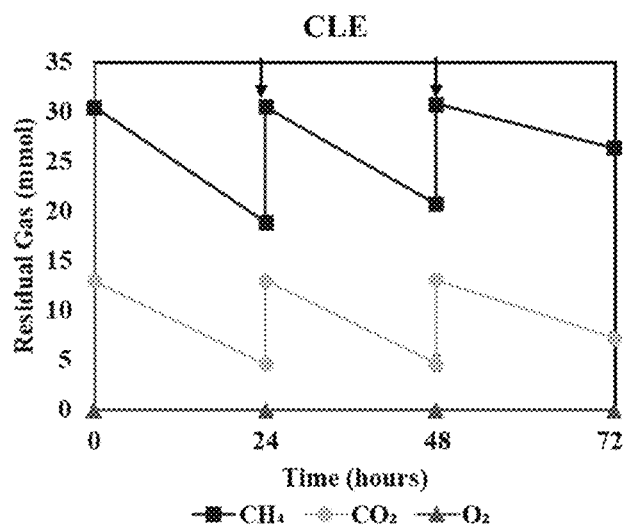
Figure 11A:
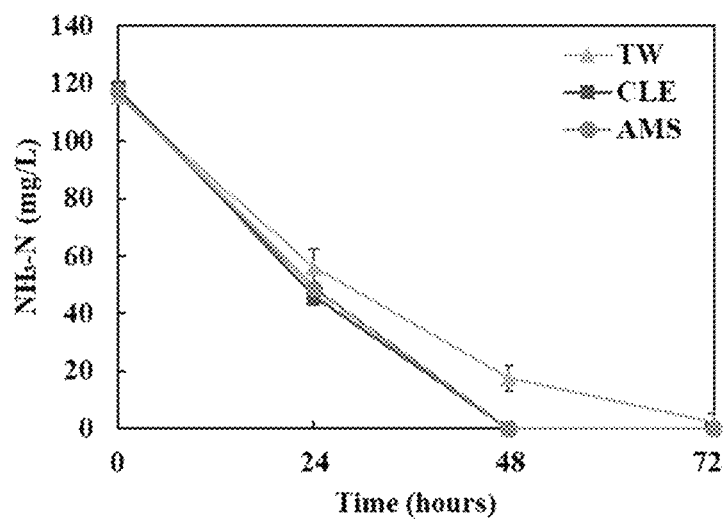
FIGS. 11A-11C show residual inorganic ammonia nitrogen concentrations (FIG. 11A), residual phosphorus concentrations (FIG. 11B), and percent recovery of same in *M. capsulatus* and *C. sorokiniana* cocultures grown on anaerobic digestate diluted with tap water (AD-TW), anaerobic digestate diluted with secondary clarifier effluent (AD-CLE), and anaerobic digestate diluted with a modified ammonium mineral salts medium (AD-AMS). The data suggest that the coculture can effectively recover nutrient from diluted anaerobic digestion (AD) effluent. The nutrient recovery rate calculated based on Eqn. (1) shows near 100% recovery rate in all dilution scenarios (FIG. 11C).
Figure 11B:
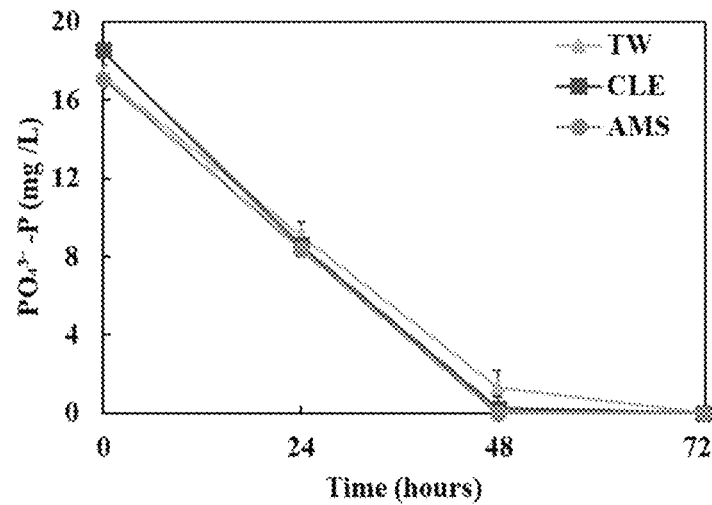
Figure 11C:
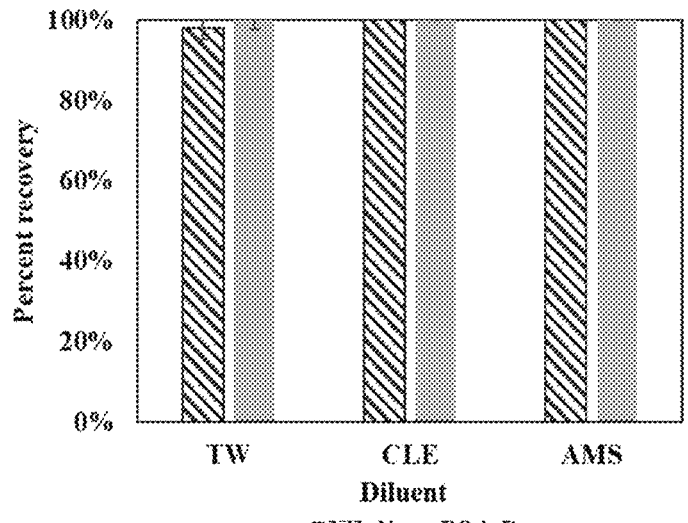

FIGS. 10A-10C show the gas phase composition for different culture media (i.e., AD effluent diluted by different diluent) over time, where the arrows indicate when the bottles were refed during the cultivation period. FIGS. 10A-10C confirm that the coupling of methane oxidation with oxygenic photosynthesis enables continuous consumption of biogas without external oxygen supply. Both $CH_4$ and $CO_2$ were consumed consistently without $O_2$ accumulation, which eliminates the inhibition of excessive oxygen on microalgae growth and the risk of explosion. Both $CH_4$ and $CO_2$ consumption slowed during the third day, potentially due to the depletion of micronutrients in the wastewater. This was confirmed by nutrient measurements, i.e., FIGS. 11A-11C, which plot the inorganic nitrogen ($NH_3$—N) and orthophosphates ($PO_4^{3-}$—P) concentrations over time. FIGS. 11A-11C show that most of the N and P were consumed by 48 hours. This result further confirms the effectiveness of the coculture in recovering the nutrients from wastewater, which shows near 100% recovery of ammonia nitrogen and orthophosphates. In this work nitrate and nitrite were not measured as preliminary analyses revealed they were negligible in the wastewater samples.

Coculture growth on differently pretreated AD effluent diluted by CLE: Liquid medium sterilization represents a major cost for most biotechnologies. Such cost could be justified if the technology produces highly valuable products such as pharmaceuticals. However, this is not the case for wastewater treatment. For the coculture-based technology to be applicable for wastewater treatment, minimum or no sterilization of the AD effluent is necessary. Therefore, we investigated whether the coculture can grow well on non-sterilized AD effluent (diluted with CLE), and compared the coculture growth on differently pretreated AD effluent: settled (S), filtered (F) and autoclaved (A). For comparison purposes, we also compared coculture growth on sterilized, modified AMS medium.

Figure 12A:
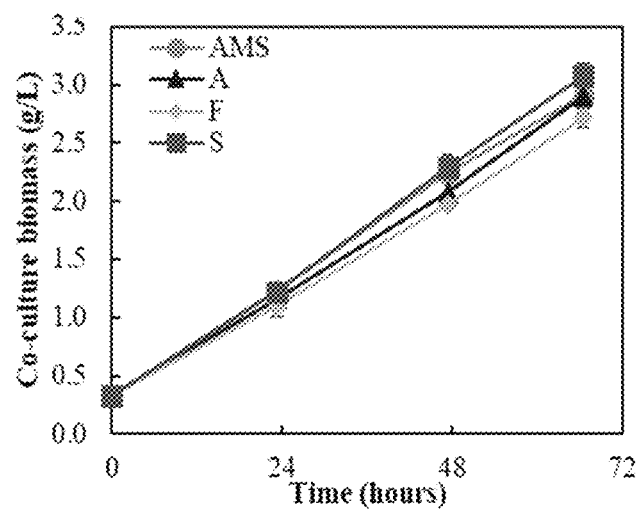
FIGS. 12A-12C show concentration profiles over time for *M. capsulatus* and *C. sorokiniana* cocultures cultivated on differently pre-treated AD effluent (settled (S), filtered (F), and autoclaved (A)), using growth on sterilized, modified AMS medium (AMS) as a comparison.
Figure 12B:
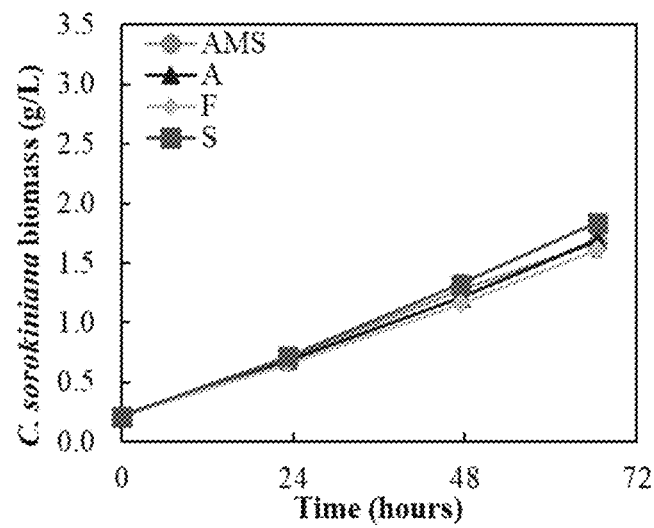
Figure 12C:
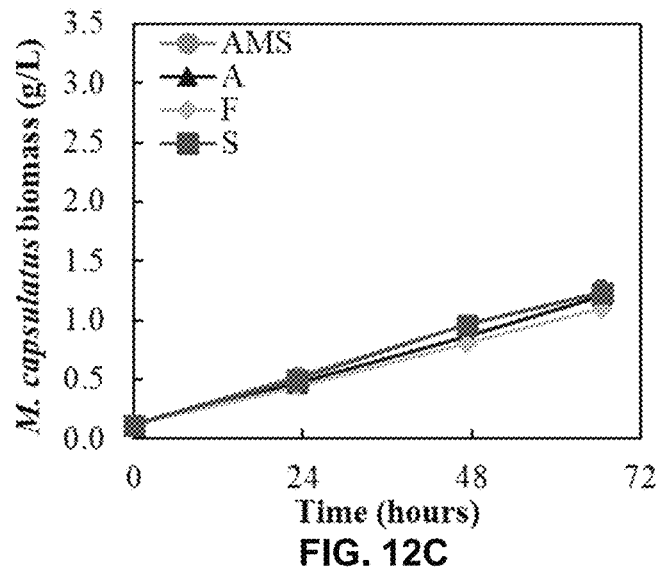

FIGS. 12A-12C plot the biomass concentration profile over time for the coculture and the individual species within the coculture grown on different pretreated AD effluent. FIGS. 12A-12C indicates that the coculture grown on settled wastewater exhibited the highest total biomass production, although there is no statistically significant difference among different pretreatment methods. This result clearly demonstrates the robustness of the coculture, as its growth was not affected by other microorganisms present in the wastewater. In addition, there could be potential synergistic effects between the coculture and microorganisms preexisted in the wastewater.

Carbon recovery by the coculture compared with sequential single culture: In this experiment we examine whether the coculture can achieve complete biogas conversion (i.e., 100% carbon recovery) without external oxygen supply. As nutrient limitation will affect the carbon substrate uptake by the coculture, this experiment was conducted without nutrient limitation. This was achieved by adding 20 mL of undiluted AD effluent 48 hours after inoculation to provide additional nutrients. For comparison, the coculture performance was compared with sequential single cultures of the individual species, i.e., C. sorokiniana followed by M. capsulatus. For this sequential single cultures experiment, oxygen produced by the microalgae single culture was provided to the methanotroph for methane oxidation.

Figure 13A:
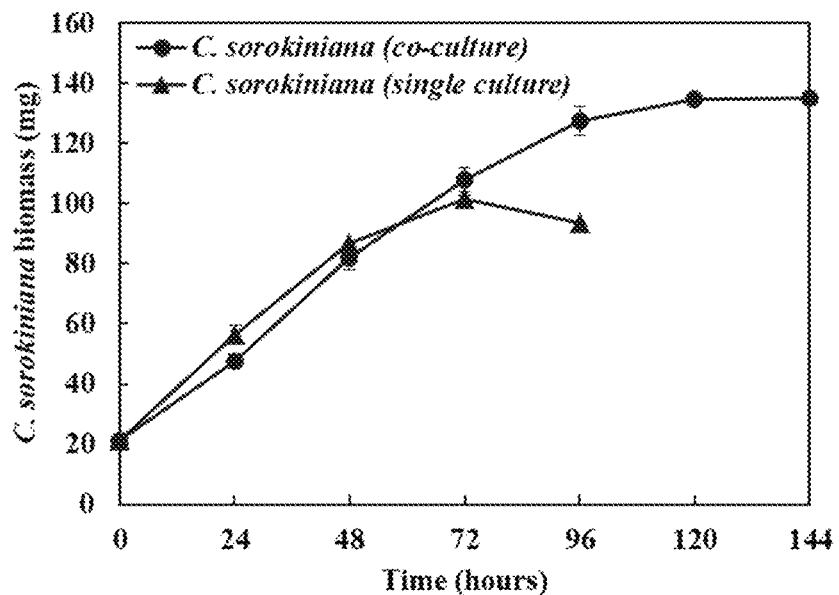
FIGS. 13A and 13B show time-course profiles of *C. sorokiniana* biomass (FIG. 13A) and *M. capsulatus* (FIG. 13B) in coculture compared to sequential single culture.
Figure 13B:
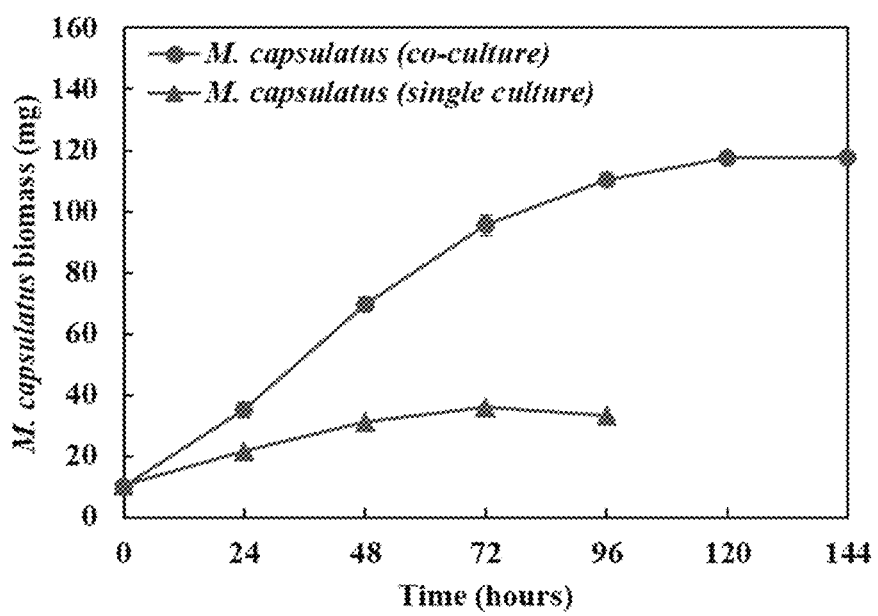
Figure 14A:
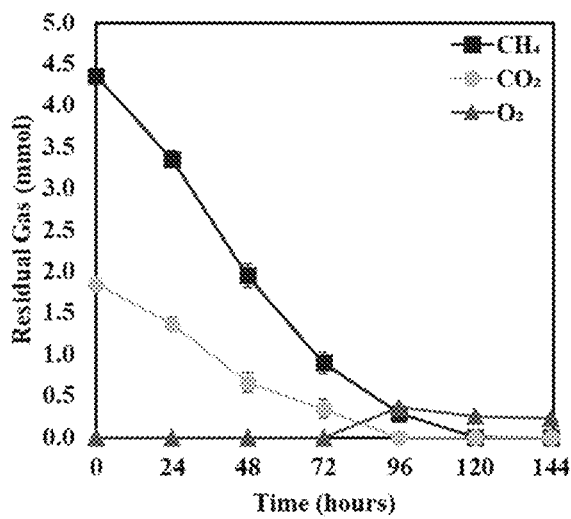
FIGS. 14A-14C show gas phase composition over time for microalga (*C. sorokiniana*) and methanotroph (*M. capsulatus*) coculture (FIG. 14A), sequential single culture microalga (FIG. 14B), and sequential single culture methanotroph (FIG. 14C). (The vacuum created by the net consumption of gas substrates was compensated by filling with $N_2$ to atmospheric pressure, which does not affect the partial pressure of the gas substrates.)
Figure 14B:
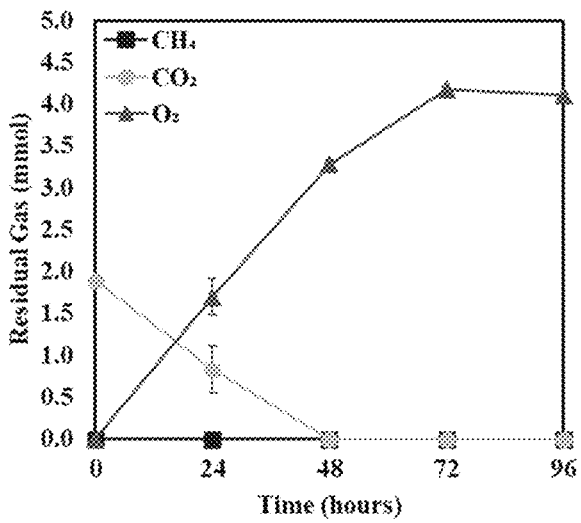
Figure 14C:
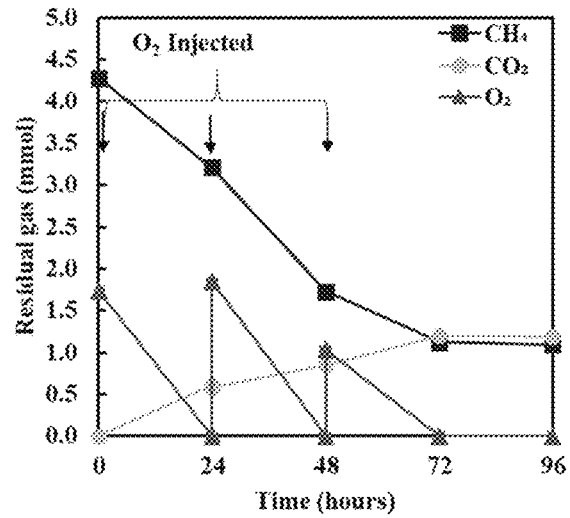

FIGS. 13A and 13B compare the biomass profiles of C. sorokiniana and M. capsulatus in coculture with that of sequential single cultures. FIGS. 13A and 13B clearly show that both C. sorokiniana and M. capsulatus in the coculture demonstrated significantly improved growth compared to the sequential single cultures. In addition, analysis of the gas phase composition (FIGS. 14A-14C) confirmed that the coculture was able to completely convert biogas into microbial biomass without external oxygen supply. It is worth noting that the vacuum created by the net consumption of gas substrates was compensated by filling with $N_2$ to atmospheric pressure, which does not affect the partial pressure of the gas substrates. In this experiment, the biomass production of *C. sorokiniana* in the coculture (113.76±1.09 mg) showed a 57% increase compared to the single culture (72.39±0.73 mg), while the biomass production of *M. capsulatus* in the coculture (108.31±0.06 mg) showed a 371% increase compared to the sequential single culture (22.75±0.46 mg). As shown in FIGS. 14A-14C, in the coculture, $CO_2$ generated during methane oxidation was utilized for photosynthesis. This was reflected in the slower reduction in $CO_2$ concentration in the coculture than that in the microalgae single culture. The methanotroph-generated $CO_2$ was converted to $O_2$ through photosynthesis, which in turn enables additional methane oxidation. This was reflected in the continuous reduction of $CH_4$ in the gas phase. On the other hand, in the sequential single culture, *C. sorokiniana* can only utilize the $CO_2$ contained in biogas, and thus produced less amount of oxygen compared to the coculture; as a result, residual $CH_4$ was observed in the methanotroph bottle due to the limited oxygen supply.

Nutrient recovery by the coculture: This experiment was performed to determine whether the coculture offers an improvement in nutrient recovery compared to the sequential single cultures. The experimental setup was the same as that in the previous section, with the only difference being that no additional nutrient was added after 48 hours. For all cultures, total nitrogen (TN), inorganic nitrogen ($NH_3$—N), total phosphorus (TP) and inorganic phosphorus ($PO_4^{3-}$—P) were measured to assess the nutrient recovery by different cultures.

Figure 15A:
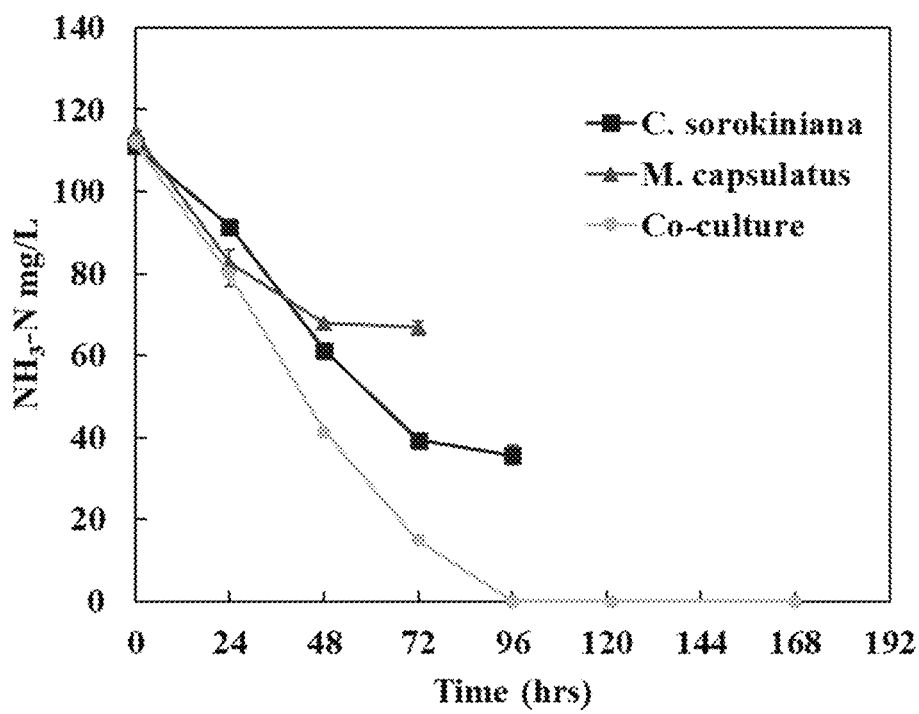
FIGS. 15A-15C show inorganic nutrient removal by sequential microalga (*C. sorokiniana*) and methanotroph (*M. capsulatus*) single cultures and by coculture for $NH_3$—N (FIG. 15A) and $PO_4^{3-}$—P (FIG. 15B), total nitrogen (FIG. 15C), and total phosphorus (FIG. 15D), indicating that the coculture exhibits enhanced nutrient recovery compared to the sequential single cultures.
Figure 15B:
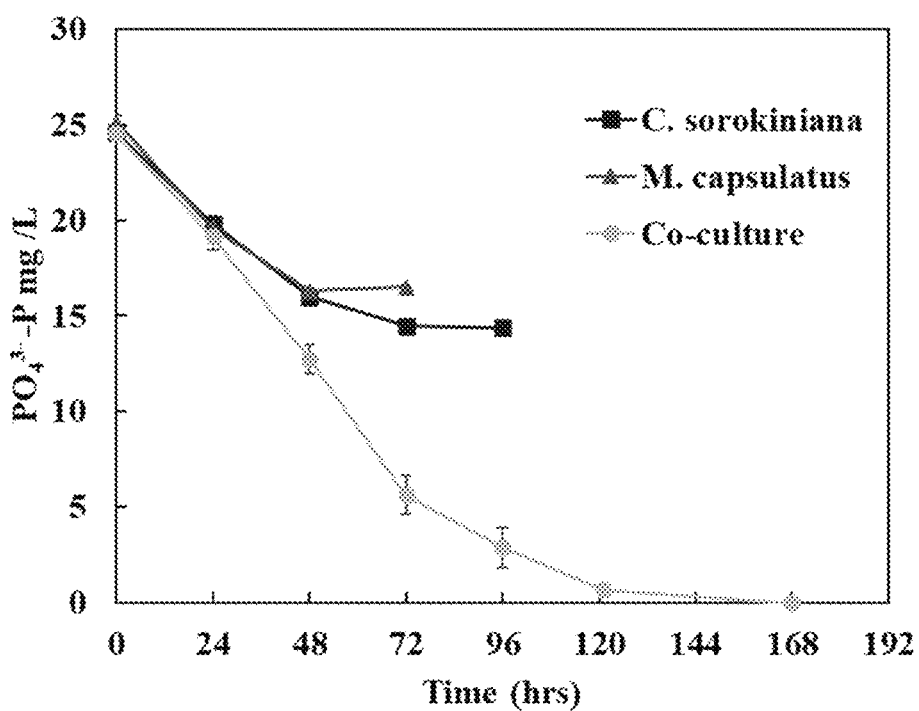
Figure 15C:
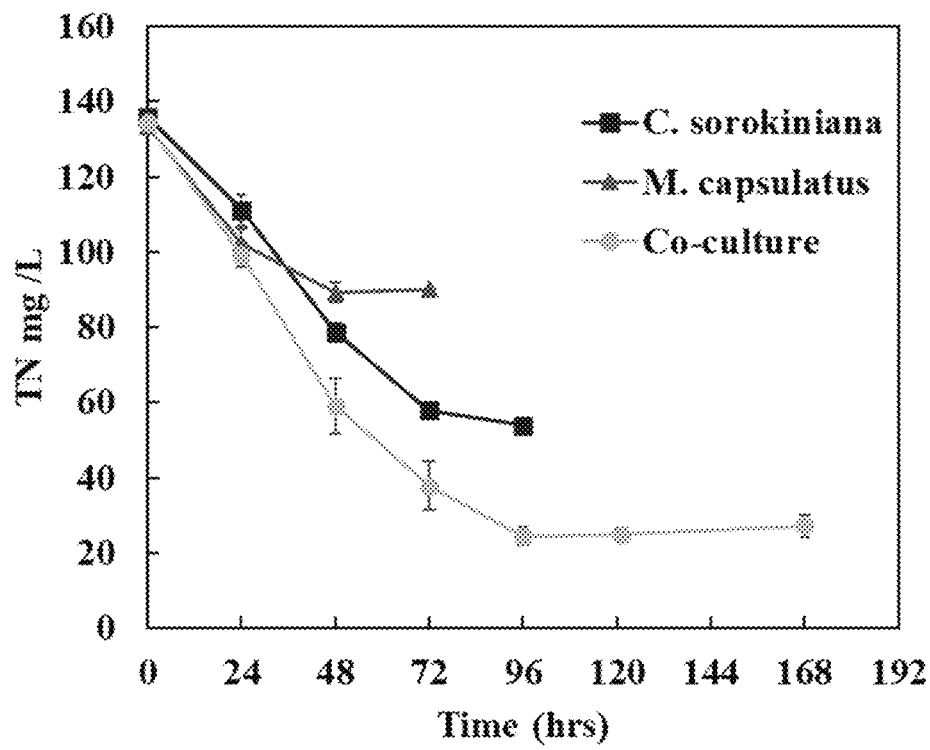
Figure 15D:
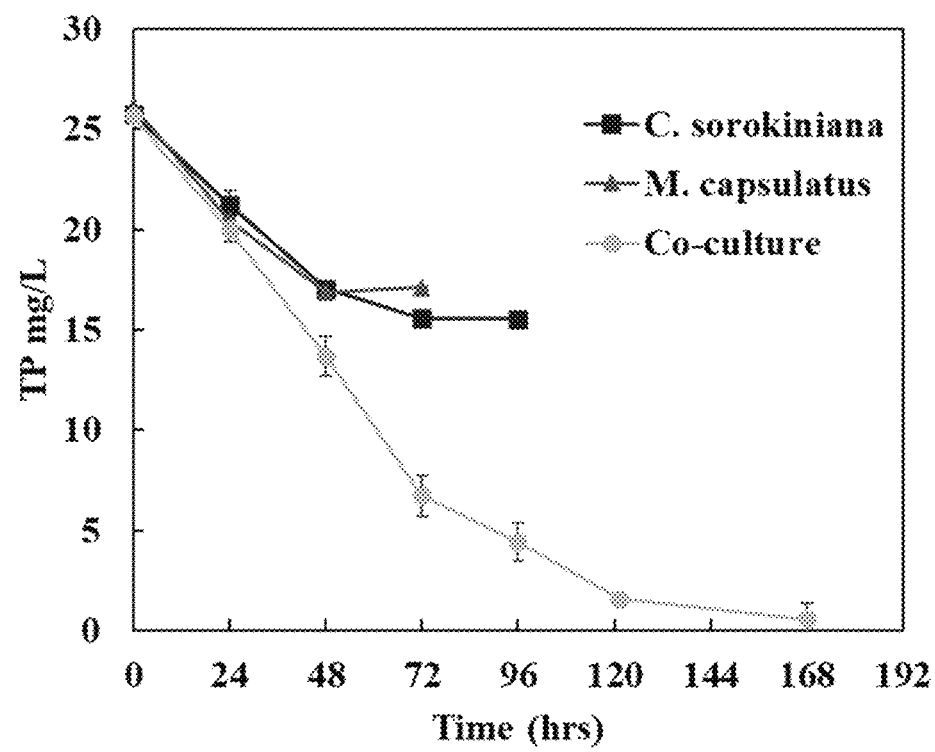

The concentration profiles for different nutrient components are plotted in FIGS. 15A-15D, which compare the coculture with sequential single cultures. FIGS. 15A-15D clearly showed that neither of the single cultures was able to completely remove the inorganic nutrients ($NH_3$—N and $PO_4^{3-}$—P), as the cell growth stopped when the respective carbon source became limited. On the other hand, the coculture was able to completely remove both inorganic nutrients (FIGS. 15A and 15B for N and P, respectively) at a faster rate, which is likely due to the enhanced growth enabled by the in situ exchange of $CO_2$ and $O_2$. When considering the removal of total nitrogen, FIG. 15C indicates that the coculture is not effective in removing organic nitrogen. FIG. 15D suggests that the total phosphorus present in the AD digestate is predominantly inorganic phosphorus, as the total phosphorus profile is very similar to the inorganic phosphate profile (FIG. 15B).

Figure 16:
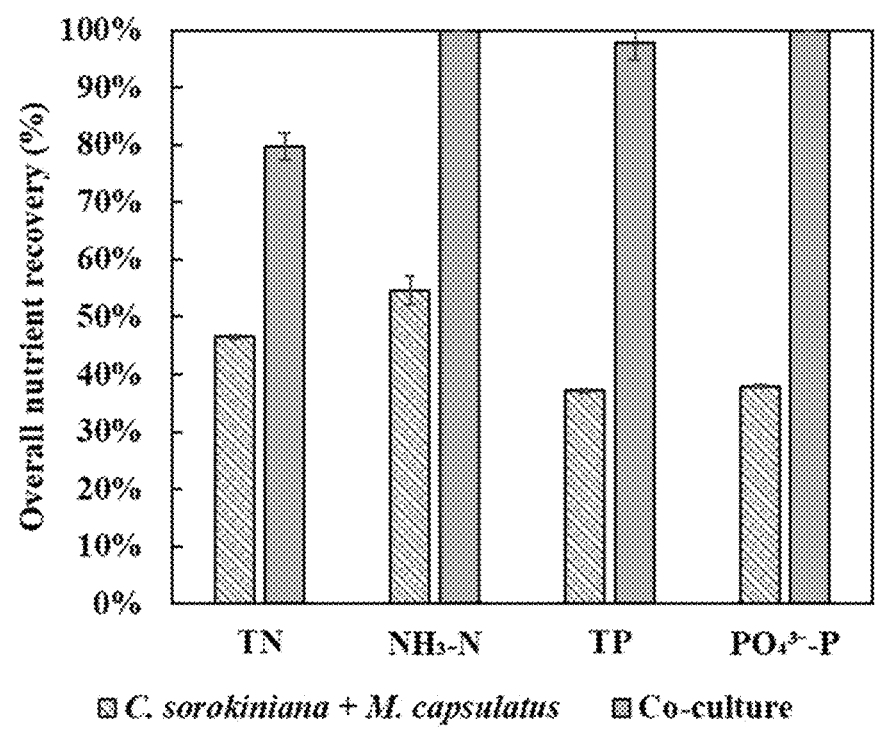
FIG. 16 shows percent nutrient recovery by microalga (*C. sorokiniana*) and methanotroph (*M. capsulatus*) cocultures compared to the sum of the single cultures, revealing the coculture is more effective at removing both inorganic nitrogen and phosphorus.
Figure 17A:
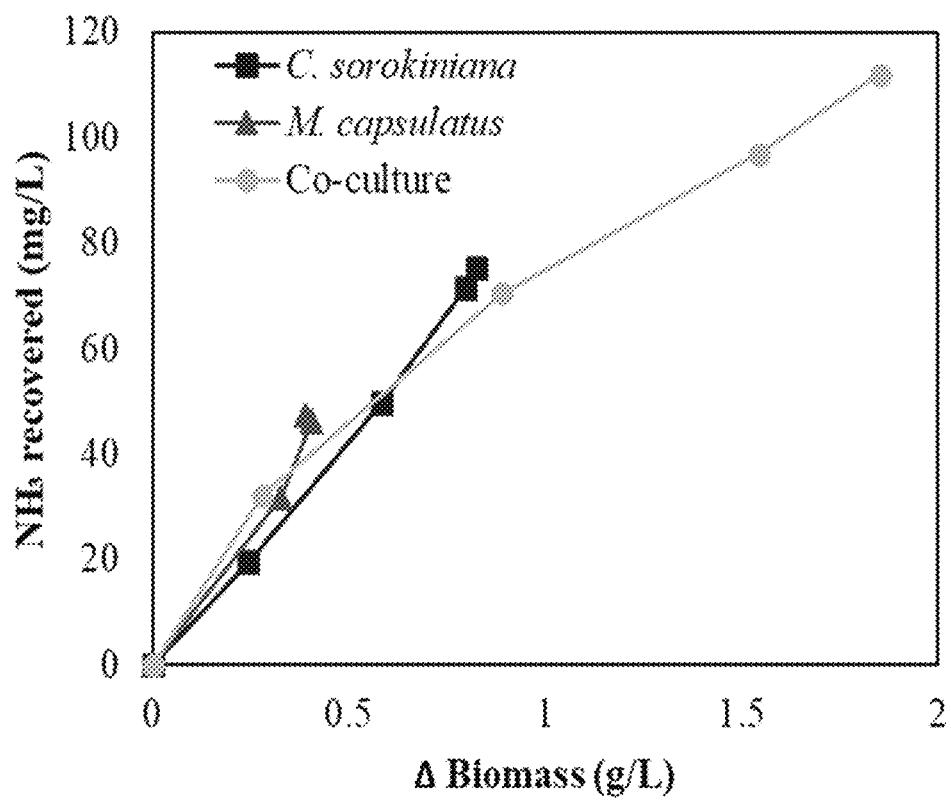
FIGS. 17A and 17B show a correlation of biomass produced with recovery of $NH_3$—N (FIG. 17A) and $PO_4^{3-}$—P (FIG. 17B) in microalga (*C. sorokiniana*) and methanotroph (*M. capsulatus*) coculture, revealing that nutrient recovery is directly related to biomass production and the enhanced nutrient recovery by the coculture is a result of the cocultures prolonged growth on biogas with no external oxygen supply.
Figure 17B:
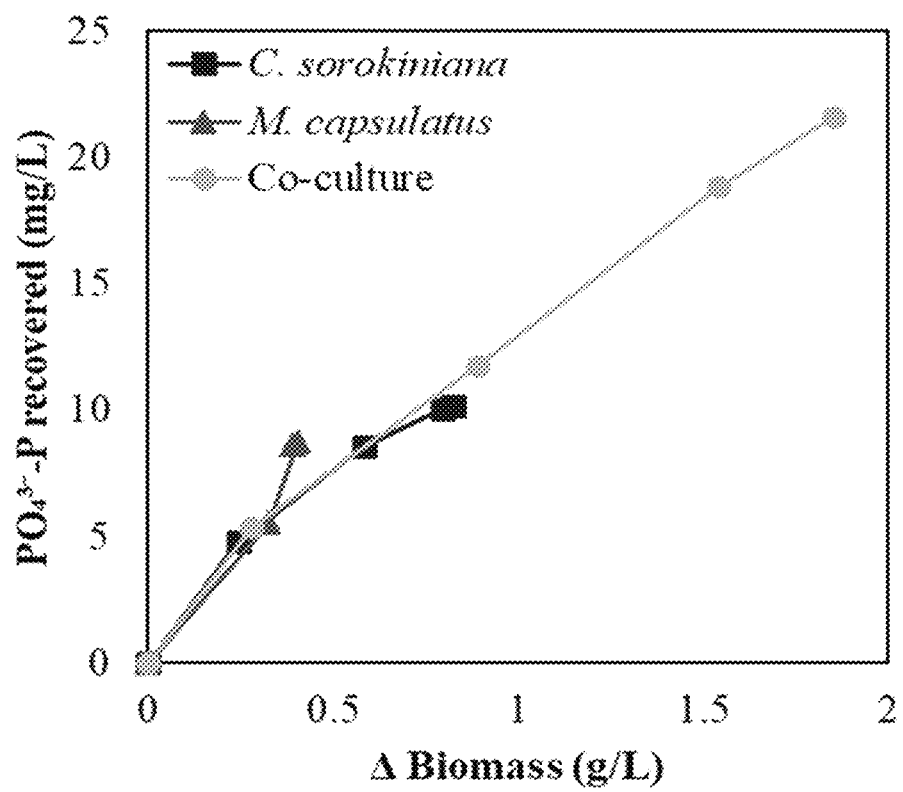

FIG. 16 compares the nutrient recovery performance of the sequential single cultures summed together with that of the coculture, which clearly demonstrates the improvement provided by the coculture for nutrient removal. To determine if the enhanced nutrient removal by the coculture was due to the enhanced growth, we plotted the amount of biomass produced vs. the amount of N and P removed, as shown in FIGS. 17A and 17B. For $NH_3$—N removal, FIG. 17A shows that the coculture appears to recover more N per unit biomass produced than both single cultures at the beginning of the batch culture, while the rate decreases as more biomass was produced. This is likely due the reduced N supply from liquid medium. For $PO_4^{3-}$—P removal (FIG. 17B), the coculture and both single cultures show little differences at the begging of the batch culture, and the recovery rate reduces as more biomass was produced. This result suggests that the enhanced nutrient recovery by the coculture was mainly due to the enhanced coculture growth compared to single cultures.

Discussion

Microalgae vs microalgae-methanotroph coculture for combined biogas upgrade and wastewater treatment: Due to their photosynthetic and nutrient recovery capabilities, microalgae have been studied in municipal wastewater treatment for over 50 years (Olguin, 2012; Su et al., 2012; Hende et al., 2014), and more recently for bioremediation of manure effluents (Woertz et al., 2009; Abou-Shanab et al., 2013). For algal biomass production, using alternative sources such as wastewater to support cell growth is highly attractive since nutrient costs have been one of the major limiting factors for sustained microalgae cultivation. In recent years, it has been shown that supplementing $CO_2$ in the municipal wastewater treatment can increase the algal biomass productivity by almost 3-fold (Abdel-Raouf et al., 2012). Microalgae have also been studied to upgrade biogas produced from AD of swine wastewater, and multiple studies have shown that microalgae or microalgae-bacteria consortia can remove >99% of $H_2S$ in biogas (Muñoz et al., 2015). These studies have demonstrated that using microalgae to remove $CO_2$ and $H_2S$ is a promising method for biogas upgrading.

However, microalgae-based wastewater treatment and biogas upgrading have limitations: (1) when $O_2$ is produced from photosynthesis and mixed with CH4, the treated biogas becomes explosive and poses a serious safety risk; (2) the presence of excessive $O_2$ inhibits the growth of microalgae and reduces its productivity. The proposed microalgae-methanotroph coculture can address these limitations effectively, as the exchange of in situ produced $O_2$ and $CO_2$ not only reduce or remove the explosion risk, but also eliminate the inhibition of excessive oxygen on the growth of the microalgae. In addition, the metabolic coupling of methane oxidation and oxygenic photosynthesis enables significantly improved biomass production for both microalgae and methanotroph, which in turn enabled faster and better nutrient recovery from wastewater as demonstrated in this work.

Potential products from the coculture microbial biomass: Currently, most of the microalgae produced from wastewater treatment process is fed back to the AD to enhance biogas production. This is mainly due to the high cost of downstream processing needed to upgrade microalgae into biodiesel. To address this limitation, we suggest the following potential products for the coculture microbial biomass.

First, if the source of the wastewater is determined to be safe (i.e., low level of heavy metal, antibiotics, etc.), such as the wastewater produced from winery and food processing plants, the wastewater-derived coculture biomass could be used as single cell protein for aquafeed supplement. It is worth noting that both microalgae and methanotroph have been extensively studied and tested as protein supplement for aquafeed supplements. For methanotrophs, trials in fish have shown that the protein meal derived from methanotrophs performs well as an alternative protein source to fish meal in feed formulations for Atlantic salmon (Aas et al., 2006), as well as improved growth performance and health benefits in aquatic and terrestrial animals (verland et al., 2010; Romarheim et al., 2010). For microalgae, positive testing results in fish and shrimp have suggested that a significantly higher dietary inclusion level of microalgal biomass in aquafeeds is expected (Becker, 2007; Teimouri et al., 2013; Gamboa-Delgado and Marquez-Reyes, 2018). These existing research suggest that the coculture biomass of microalgae and methanotroph could be a highly promising source for single cell protein, pending biomass composition analysis of the coculture.

Second, the coculture biomass can be processed through hydrothermal liquefaction (HTL) to produce biocrude. HTL is a promising route for producing renewable fuels and chemicals from wet biomass (Biller and Ross, 2012). It uses water contained in wet biomass at sub- or super-critical temperatures and pressures as a reactant and reaction medium (Gupta and Demirbas, 2010). Compared to conventional thermochemical processes (such as pyrolysis and gasification), HTL does not require dry biomass, which saves a huge amount of energy (Zou et al., 2009). In addition, HTL converts the whole cell, i.e., lipid, protein and carbohydrate, into biocrude, which increases the total oil production (Biller and Ross, 2011; Garcia Alba et al., 2011). Finally, HTL can use various feedstock, such as microbial biomass, woody biomass, and sewage sludge, without pretreatment. Therefore, using coculture biomass as feedstock for biocrude production is also a viable option.

Finally, coculture biomass is a promising source for producing bioplastics. As worldwide usage of plastics continues to increase, it is urgent to find ways of producing bioplastics in large quantities economically with comparable material properties to their petroleum counterparts. This is due the detrimental environmental impact of petroleum-based plastics: preventing biodegradation, increasing demand and size of landfills. In addition, the process of resin production from crude oil further harms the environment by producing waste products, leading to air, water and ground contaminations (Zeller et al., 2013). It has been reported that microalgae derived bioplastics have similar properties as the petroleum-based plastics and thus can be "dropped in" to existing infrastructure and applications (Wang et al., 2016). Furthermore, existing research also suggest that mixed microalgae-bacteria biomass with proper protein content demonstrate similar properties as microalgae biomass for bioplastic production (Rahman and Miller, 2017). Therefore, as long as the microalgae-methanotroph coculture biomass has proper protein content, it could be used to produce bioplastic as well.

In this example, we demonstrated that the microalgae-methanotroph coculture platform offers an energy efficient route for wastewater treatment, which can simultaneously convert low value biogas into microbial biomass while removing nutrient from AD effluent. The coculture platform explored the metabolic coupling of methane oxidation with oxygenic photosynthesis and demonstrated significantly improved biomass productivity compared to microalgae-based wastewater treatment. Through an on-going collaboration with Columbus Water Works (a municipal WRRF in Georgia), we demonstrated that the model coculture *C. sorokiniana* and *M. capsulatus* exhibited robust and stable growth on minimally treated AD effluent. Specifically, the coculture showed the best growth performance on digestate that was simply settled to remove solids without any sterilization. In addition, the coculture grew on AD effluent diluted by clarifier water showed the best growth performance. This is important as it showed that the coculture-based wastewater treatment does not require fresh water supply to dilute the effluent. Enabled by the in-situ exchange of $O_2$ and $CO_2$, the coculture was able to achieve complete biogas conversion, i.e., "zero emission" without external oxygen supply. In addition, the coculture demonstrated complete removal of inorganic nitrogen and phosphorus, and significantly improved nutrient removed efficiency than the single cultures. The enhanced capability of nutrient removal by the coculture was highly correlated to the improved coculture growth due to the synergistic interaction within the culture. Finally, the potential value-added products that can be derived from the coculture.

Example 3

Circulating Coculture Biofilm Photobioreactor (CCBP) for Valorization of Anaerobic Digestion Waste The examples provided above show that methanotrophs and phototrophs (such as microalgae and/or cyanobacteria) can stably grow together in coculture while simultaneously consuming $CH_4$ and $CO_2$ to produce cell biomass, that the coculture pairs can grow in wastewater from a wastewater treatment plant, and that the produced coculture biomass can be used to produce biofuel, biochemicals, and animal feed.

To facilitate the growth of methanotroph-phototroph cocultures for processing wastewater and biogas, we developed a circulating coculture biofilm photobioreactors (CCBPs) as shown in FIGS. 1A and 1B. A conveyor belt (surface 7) that offers cell attachment (or biofilm support) is stretched around support shafts 20,21 to form a zigzag configuration. The lower part of the zigzag configuration is submerged in the liquid reservoir with wastewater (which contains nutrients), while the upper part is exposed to the biogas. By exposing the coculture biofilm directly to the gas phase, the mass transfer resistance from the gas phase to the cells is reduced significantly, as the diffusion through the bulk liquid phase is eliminated. The zigzag configuration not only provides high biomass production area with low land footprint, but also enables sunlight dilution. The housing 2 that holds the biogas can be constructed similar to an enclosed green house for exposure to sunlight. One or multiple motor(s) drive the drive shaft(s) (any one or more of 20,21,23,24), which rotate the conveyor belt, enabling the attached biofilm to alternately access nutrients when submerged in the liquid phase and to access gas substrate ($CH_4$ and $CO_2$) when exposed in the biogas. Gas and liquid inlet ports (e.g., first intake port 8 and second intake port 9) can permit the inflow of biogas and wastewater, respectively. Gas and liquid outlet ports (e.g., headspace outlet port 10 and reservoir outlet port 11) permit the outflow of processed biogas and processed wastewater, respectively. The liquid outflow port (e.g., 11) can be fluidically connected to the liquid inflow port (e.g., 9) via a return channel 12 for dilution of incoming wastewater. Alternatively, the system 1 can include a bottom opening 2*d* in the housing 2 such that liquid can freely flow in and out of the portion of the reservoir 5 surrounded by the housing 2. The system can be equipped with model-based control of the conveyor belt revolving speed for optimized growth. The model captures the effect of light intensity, gas, and liquid substrate composition, and mixed culture growth dynamics. Model predictive control (MPC) can control the conveyor belt revolving speed in real-time to optimize the mixed culture biomass growth. A retractable press wheel 13 can compress the belt against one of the support shafts 20,21,22,23 to remove water from the already high-solids-content biomass for biomass harvesting. A retractable blade 14 can scrape the biomass off the circulating belt for biomass harvesting. The system is capable of simultaneously removing nitrogen and phosphorus from wastewater while removing both $CH_4$ and $CO_2$ from biogas. The implementation of the CCBP system is straightforward as an add-on or a plug-in to existing wastewater treatment plants.

We constructed a small-scale, exemplary CCBP in accordance with the schema shown in FIG. 1A. The exemplary CCBP was a 68-L (72 Qt), bench, scale reactor. The container was 15×18×23-inch (H×L×W) acrylic with a ⅜-inch wall thickness. The lid was made of 1-inch thick acrylic with a ½A-inch deep trough cut out to fit on top of the container. A peristaltic pump was used to circulate the medium in the reactor at 50-1000 mL/min and pH of the medium was configured to be continuously controlled. An Internet-of-Things (IoT) camera, as well as an IoT temperature and pressure sensor (JBtek BMP180) were installed. The IoT devices were connected to a Raspberry Pi computer (Raspberry Pi Trading, UK), enabling continuous and remote monitoring of the inside of the reactor. An aquarium heater (Nuochong H-200) was installed to maintain a reactor temperature of ~31° C. The light source for the prototype was composed of a flexible LED sheet that provides illumination at a measured photosynthetically active radiation (PAR) of ~680 $\mu mol\ m^{-2}\ s^{-1}$ at the belt's highest points. The prototype was placed in a chemical hood with additional safety features (flammable gas detector and auto-shutoff valves) installed. The reactor was capable of being run in either batch mode or continuous mode. We successfully used the exemplary CCBP to achieve growth of methanotroph-phototroph coculture biofilm on the conveyor belt in the presence of wastewater and biogas media.

Usually, photosynthesis efficiency is limited to the available surface area, and the high energy/cost associated with harvesting microbial biomass can significantly reduce the profitability of the overall process. The CCBP addresses these challenges. It not only enables very low-cost cell harvesting and enhanced biomass growth, but also significantly reduces the footprint area. There are several advantages of the proposed biofilm reactor compared to the conventional suspended cultivation: (1) The reactor has large surface area for gas substrate uptake by cells; the thin liquid layer when exposed to biogas also makes gas transfer rates much higher compared to suspended cultivation. These two together make the system ideal for biogas conversion. (2) The zigzag configuration makes the system highly compact with a large surface area, optimal for photosynthesis utilizing sunlight. At the same time, it does not occupy a large land area like conventional open pond cultivation. (3) The revolving conveyor belt periodically exposes the cells to sunlight, preventing light-induced inhibition in algae during the period when the sunlight is too strong. (4) Most parts of the conveyor belt are above the liquid reservoir, which removes most of the water when harvested through scrubbing or spooling at the top of the configuration. This harvesting technique is much simpler and much more energy efficient compared to filtering or centrifugation.

The CCBP system of the invention provides a number of specific advantages over existing bioreactors designed for methane conversion. Existing bioreactors designed for methane conversion are all liquid-phase reactors for suspended cultivation. Because of the small solubility of methane and oxygen in aqueous solutions, mass transfer is the limiting step for methanotroph growth in these systems. Static mixing, air loop, multiple gas injecting points are the common strategies to overcome the problem of mass transfer in these systems. In contrast, the CCBP system is a dual-phase reactor, where cells are immobilized on the conveyor belt and are in direct contact with methane and oxygen gas supply. Such a configuration eliminates the significant mass transfer resistance where gas substrates have to pass from gas phase through bulk liquid phase to reach cell surface. The configuration enables significantly increased cell growth. In addition, immobilized cells on the belt significantly reduce the cost associated with cell harvesting, which conventionally occurs through centrifuging. Finally, the present system offers vastly enhanced robustness, and cells can tolerate much higher inhibitor concentrations, which enables easier operation and control of the bioreactor.

The CCBP system of the invention provides specific advantages over biofilm-based photobioreactors for wastewater treatment. Existing biofilm-based technologies for wastewater treatment are algal based technologies that do not really have a reactor because they are all open systems, that is, they are open to air and consume $CO_2$ from air instead of biogas. In contrast, the present CCBP is a closed reactor system at least with respect to the gas phase. The closed configuration allows much higher concentration of $CO_2$ supply through biogas (up to 50% v/v $CO_2$ or more). Increasing $CO_2$ feed concentration significantly improves microalgae growth, and improves the process productivity and throughput, therefore lowering the cost. In addition, the closed configuration significantly reduces water evaporation, enables temperature control, and, therefore, further improves cell growth performance.

The CCBP system of the invention provides other advantages. Automatic control of the photobioreactor enables superior performance compared to other open or closed reactor configurations. Microalgae cultivation systems rely on energy from sunlight to be economically viable; however, sunlight availability is dynamic depending on time of day and season. Therefore, one important aspect of the CCBP system is the zigzag conveying system that enables the cells to interact with both the liquid phase (the anaerobic digester digestate containing essential nutrients (e.g., ammonia and phosphorus)) and the gas phase (e.g., biogas containing methane and carbon dioxide). The zigzag configuration also plays an important role in exposing the biofilm to light, such as sunlight, which is essential for growth of the phototroph. In order to maximize the sunlight conversion efficiency of the photoautotroph and decrease the areal requirement of the CCBP, the angle of the belt between the upper 20 and lower 21 rotary shafts can be configured to be within 30-60° relative to the horizontal plane. When the daylight is strongest (e.g., 10 am-4 pm), the angle can be steepest to avoid photoinhibition. However, in the morning and evening hours or overcast days, the angle can be decreased to maximize exposure of the cells to the available sunlight. The cell exposure to sunlight can therefore be dynamically controlled based on a model relating cell growth to light intensity and other conditions. This can be achieved by controlling the angle between the upper 20 and lower 21 rotary shafts by, for example, increasing/decreasing the vertical distance between the upper shafts 20 and lower shafts 21, decreasing/increasing the horizontal distance between the upper shafts 20, and/or increasing/decreasing the horizontal distance between the lower shafts 21. Adjustment of slack or tension on the belt introduced by such movements can be addressed by a tension shaft 23 to be extended or retracted. (This could be achieved, for example, by using a telescopic arm to hold the designated shafts).

Cell exposure to sunlight can also be controlled by adjusting the speed of the belt. Such adjustment should consider limitations on speed due to shear on the cells.

Artificial lighting systems, such as LED lighting systems, can supplement sunlight during night-time hours or low-light periods. This permits the CCBP to continue to perform when sunlight is not available. The source of power can be from solar panels which generate power during the day, or it can be drawn from the power grid because the price is significantly lower during the night than during the day.

Other advantages over conventional systems include the use of a press wheel for dewatering to increase the solids content of the harvested biomass as well as an automated harvesting blade. Conventional systems require an operator to inspect the biofilm and determine whether it is ready to be harvested. Once the operator decides the biofilm is ready to be harvested, the operator physically scrapes the biofilm. In the present system, the harvesting blade can be automatically applied to scrape the biofilm from the belt material. The use of a sensor, such as an IoT sensor, which may include but is not limited to a sonar, fluorescence, or light transmission detector, can be used to determine biofilm thickness. A predictive model captures how the growth of the biofilm is affected by its thickness. The model determines an optimal harvesting biofilm thickness. Once the automatic control system determines that the biofilm has reached the harvesting thickness, the press wheel and scraping blade can be applied to harvest the biofilm.

In the present exemplary system, the oxygen produced by the phototroph is consumed by the methanotroph in situ. This removes the mass transfer resistance on oxygen and eliminates the need for oxygen supply, therefore eliminating the potential risk of explosion (methane is explosive when mixed with oxygen). Removal of the produced oxygen in situ by the methanotroph also removes potential inhibition of oxygen on phototroph growth. In addition, both methanotroph and microalgae contribute to metabolite exchange within the coculture, including amino acids and organic acids, which enable improved growth of both species.

The CCBP system can be implemented in an autonomous, self-contained, robust (fault-proof) system. The CCBP system is portable, scalable, and fully automated for remote process monitoring and control. Remote monitoring of the CCBP can be employed using an IoT camera and IoT pressure and temperature sensors.

The CCBP system of the invention is flexible. Beyond treating wastewater and converting biogas as described above, the system can be used to process biogas alone (with fresh or brackish water plus nutrients as the liquid medium) to produce biofuels, chemicals, food supplements and/or animal feed. It can also be used to process natural gas to produce the same products.

REFERENCES

Aas, T. S., Grisdale-Helland, B., Terjesen, B. F., and Helland, S. J. (2006). Improved growth and nutrient utilisation in Atlantic salmon (Salmo salar) fed diets containing a bacterial protein meal. *Aquaculture* 259, 365-376.

Abdel-Raouf, N., Al-Homaidan, A. A., and Ibraheem, I. B. M. (2012). Microalgae and wastewater treatment. *Saudi J. Biol. Sci.* 19, 257-275.

Abou-Shanab, R. A. I., Ji, M.-K., Kim, H.-C., Paeng, K.-J., and Jeon, B.-H. (2013). Microalgal species growing on piggery wastewater as a valuable candidate for nutrient removal and biodiesel production. *J. Environ. Manage.* 115, 257-264.

AgSTAR, U.S., 2018. *Market opportunities for biogas recovery systems at U.S. livestock facilities.*

Angelidaki, I., and Ellegaard, L. (2003). Codigestion of manure and organic wastes in centralized biogas plants. *Appl. Biochem. Biotechnol.* 109, 95-105.

Badr, K., Hilliard, M., Roberts, N., He, Q. P., and Wang, J. (2019). Photoautotroph-Methanotroph Coculture—A Flexible Platform for Efficient Biological $CO_2$-CH4 Co-utilization. *IFAC-PapersOnLine* 52, 916-921. doi: 10.1016/j.ifacol.2019.06.179.

Bahr, K., Roberts, N., He, Q. P., Wang, J., 2018. Understanding the stability and robustness of a methanotroph-cyanobacterium coculture through kinetic modeling and experimental verification. 2018 *AIChE Annu. Conf.*

Béchet, Q., Shilton, A., Guieysse, B., 2013. Modeling the effects of light and temperature on algae growth: state of the art and critical assessment for productivity prediction during outdoor cultivation. *Biotechnol. Adv.* 31, 1648-1663.

Becker, E. W. (2007). Micro-algae as a source of protein. *Biotechnol. Adv.* 25, 207-210.

Biller, P., and Ross, A. B. (2011). Potential yields and properties of oil from the hydrothermal liquefaction of microalgae with different biochemical content. *Bioresour. Technol.* 102, 215-225.

Biller, P., and Ross, A. B. (2012). Hydrothermal processing of algal biomass for the production of biofuels and chemicals. *Biofuels* 3, 603-623.

Christenson, L. B. & Sims, R. C. Rotating algal biofilm reactor and spool harvester for wastewater treatment with biofuels by-products. *Biotechnol. Bioeng.* 109, 1674-1684 (2012).

Driscoll, C., Whitall, D., Aber, J., Boyer, E., Castro, M., Cronan, C., et al. (2003). Nitrogen pollution: Sources and consequences in the US northeast. *Environ. Sci. Policy Sustain. Dev.* 45, 8-22.

Fei, Q., Guarnieri, M. T., Tao, L., Laurens, L. M. L., Dowe, N., and Pienkos, P. T. (2014). Bioconversion of natural gas to liquid fuel: Opportunities and challenges. *Biotechnol. Adv.* 32, 596-614.

Galloway, J. N., Dentener, F. J., Capone, D. G., Boyer, E. W., Howarth, R. W., Seitzinger, S. P., et al. (2004). Nitrogen cycles: past, present, and future. *Biogeochemistry* 70, 153-226.

Gamboa-Delgado, J., and Marquez-Reyes, J. M. (2018). Potential of microbial-derived nutrients for aquaculture development. *Rev. Aquac.* 10,224-246.

Garcia Alba, L., Torri, C., Samori, C., van der Spek, J., Fabbri, D., Kersten, S. R. A., et al. (2011). Hydrothermal treatment (HTT) of microalgae: evaluation of the process as conversion method in an algae biorefinery concept. *Energy & fuels* 26,642-657.

Gross, M., Henry, W., Michael, C. & Wen, Z. Development of a rotating algal biofilm growth system for attached microalgae growth with in situ biomass harvest. *Bioresour. Technol.* 150,195-201 (2013).

Gross, M. & Wen, Z. Yearlong evaluation of performance and durability of a pilot-scale revolving algal biofilm (RAB) cultivation system. *Bioresour. Technol.* 171, 50-58 (2014).

Gupta, R. B., and Demirbas, A. (2010). *Gasoline, diesel, and ethanol biofuels from grasses and plants.* Cambridge University Press.

Haynes, C. A., and Gonzalez, R. (2014). Rethinking biological activation of methane and conversion to liquid fuels. *Nat. Chem. Biol.* 10,331-339.

Henard, C. A., Smith, H., Dowe, N., Kalyuzhnaya, M. G., Pienkos, P. T., and Guarnieri, M. T. (2016). Bioconversion of methane to lactate by an obligate methanotrophic bacterium. *Sci. Rep.* 6.

Hende, S. Van Den, Cane, E., Cocaud, E., Beelen, V., Boon, N., and Vervaeren, H. (2014). Treatment of industrial wastewaters by microalgal bacterial flocs in sequencing batch reactors. *Bioresour. Technol.* 161,245-254.

Hill, E. A., Chrisler, W. B., Beliaev, A. S., Bernstein, H. C., 2017. A flexible microbial co-culture platform for simultaneous utilization of methane and carbon dioxide from gas feedstocks. *Bioresour. Technol.*

Hoh, D., Watson, S. & Kan, E. Algal biofilm reactors for integrated wastewater treatment and biofuel production: a review. *Chem. Eng. J.* 287, 466-473 (2016).

Kip, N., van Winden, J. F., Pan, Y., Bodrossy, L., Reichart, G.-J., Smolders, A. J., Jetten, M S., Damsté, J. S. S., den Camp, H. J. O., 2010. Global prevalence of methane oxidation by symbiotic bacteria in peat-moss ecosystems. *Nat. Geosci.* 3,617-621.

Johnson, M. B. & Wen, Z. Development of an attached microalgal growth system for biofuel production. *Appl. Microbiol. Biotechnol.* 85, 525-534 (2010).

Lee, S. A., Lee, N., Oh, H. M., and Ahn, C. Y. (2019). Enhanced and balanced microalgal wastewater treatment (COD, N, and P) by interval inoculation of activated sludge. *J. Microbiol. Biotechnol.* doi:10.4014/jmb.1905.05034.

Lee, S. H. et al. Higher biomass productivity of microalgae in an attached growth system, using wastewater. *J. Microbiol. Biotechnol* 24, 1566-1573 (2014).

Milucka, J., Kirf, M., Lu, L., Krupke, A., Lam, P., Littmann, S., Kuypers, M. M., Schubert, C. J., 2015. Methane oxidation coupled to oxygenic photosynthesis in anoxic waters. *ISME J.*

Muñoz, R., Meier, L., Diaz, I., and Jeison, D. (2015). A review on the state-of-the-art of physical/chemical and biological technologies for biogas upgrading. *Rev. Environ. Sci. Bio/Technology* 14, 727-759.

Nasir, I. M., Mohd Ghazi, T. I., and Omar, R. (2012). Anaerobic digestion technology in livestock manure treatment for biogas production: a review. *Eng. Life Sci.* 12, 258-269.

Olguin, E. J. (2012). Dual purpose microalgae--bacteria-based systems that treat wastewater and produce biodiesel and chemical products within a Biorefinery. *Biotechnol. Adv.* 30, 1031-1046.

verland, M., Tauson, A.-H., Shearer, K., and Skrede, A. (2010). Evaluation of methane-utilising bacteria products as feed ingredients for monogastric animals. *Arch. Anim. Nutr.* 64, 171-189.

Qi, Y., Beecher, N., and Finn, M. (2013). Biogas Production and Use at Water Resource Recovery Facilities in the United States. *Water Environ. Fed.*

Qu, W., Zhang, C., Zhang, Y., and Ho, S. H. (2019). Optimizing real swine wastewater treatment with maximum carbohydrate production by a newly isolated indigenous microalga Parachlorella kessleri QWY28. *Bioresour. Technol.* doi:10.1016/j.biortech.2019.121702.

Raghoebarsing, A. A., Smolders, A. J., Schmid, M. C., Rijpstra, W. I. C., Wolters-Arts, M., Derksen, J., Jetten, M S Schouten, S., Damsté, J. S. S., Lamers, L. P., 2005. Methanotrophic symbionts provide carbon for photosynthesis in peat bogs. *Nature* 436, 1153-1156.

Rahman, A., and Miller, C. D. (2017). "Microalgae as a Source of Bioplastics," in *Algal Green Chemistry: Recent Progress in Biotechnology* doi: 10.1016/B978-0-444-63784-0.00006-0.

Rasouli, Z., Valverde-Pérez, B., D'Este, M., De Francisci, D., Angelidaki, I., 2018. Nutrient recovery from industrial wastewater as single cell protein by a co-culture of green microalgae and methanotrophs. *Biochem. Eng. J.* 134, 129-135.

Roberts, N. H., M., Bahr, K., He, Q. P., Wang, J., 2018. Efficient and robust biological $CH_4/CO_2$ co-utilization through coculture of methanotroph and microalgae. *40th Symp. Biotechnol. Fuels Chem.*

Roberts, N., He, Q. P., Wang, J., 2018. Using methanotroph-microalgae coculture for wastewater treatment. *2018 AIChE Annu. Conf.*

Romarheim, O. H., Overland, M., Mydland, L. T., Skrede, A., and Landsverk, T. (2010). Bacteria grown on natural gas prevent soybean meal-induced enteritis in Atlantic salmon. *J. Nutr.* 141, 124-130.

Roberts, N., Hilliard, M., Bahr, K., He, Q. P. & Wang, J. Coculture of Methanotrophs and Microalgae—a Flexible Platform for Biological $CH_4\backslash CO_2$ Co-Utilization. *2017 AIChE Annu. Conf.* (2017).

Stone, K. A., He, Q. P., and Wang, J. (2019). Two Experimental Protocols for Accurate Measurement of Gas Component Uptake and Production Rates in Bioconversion Processes. *Sci. Rep.* 9, 5899. doi:10.1038/s41598-019-42469-3.

Stone, K., He, Q. P., Wang, J., 2017. Systematic Carbon and Growth Analysis of a Promising Methanotroph Strain. *2017 AIChE Annu. Conf.*

Su, Y., Mennerich, A., and Urban, B. (2012). Comparison of nutrient removal capacity and biomass settleability of four high-potential microalgal species. *Bioresour. Technol.* 124, 157-162.

Tandon, P., and Jin, Q. (2017). Microalgae culture enhancement through key microbial approaches. *Renew. Sustain. Energy Rev. doi:*10.1016/j.rser.2017. 05.260.

Teimouri, M., Amirkolaie, A. K., and Yeganeh, S. (2013). The effects of Spirulina platensis meal as a feed supplement on growth performance and pigmentation of rainbow trout (Oncorhynchus mykiss). *Aquaculture* 396, 14-19.

Topper, P. A., Graves, R. E., and Richard, T. (2006). The fate of nutrients and pathogens during anaerobic digestion of dairy manure. *Lehman Penn State Univ. Coll. Agric. Sci. Coop. Ext. Bull. G* 71.

Toyama, T., Kasuya, M., Hanaoka, T., Kobayashi, N., Tanaka, Y., Inoue, D., et al. (2018).

Growth promotion of three microalgae, Chlamydomonas reinhardtii, Chlorella vulgaris and Euglena gracilis, by in situ indigenous bacteria in wastewater effluent. *Biotechnol. Biofuels. doi:*10.1186/s13068-018-1174-0.

Van der Ha, D., Nachtergaele, L., Kerckhof, F.-M., Rameiyanti, D., Bossier, P., Verstraete, W., Boon, N., 2012. Conversion of biogas to bioproducts by algae and methane oxidizing bacteria. *Environ. Sci. & Technol.* 46, 13425-13431.

Wang, J., Liu, W. & Liu, T. Biofilm based attached cultivation technology for microalgal biorefineries—a review. *Bioresour. Technol.* 244, 1245-1253 (2017).

Wang, K., Mandal, A., Ayton, E., Hunt, R., Zeller, M. A., and Sharma, S. (2016). "Chapter 6—Modification of Protein Rich Algal-Biomass to Form Bioplastics and Odor Removal A2—Dhillon, Gurpreet Singh," in *Protein Byproducts* doi:https://doi.org/10.1016/B978-0-12-802391-4.00006-9.

Wang, Q., Higgins, B., Ji, H., and Zhao, D. (2018). Improved microalgae biomass production and wastewater treatment: Pre-treating municipal anaerobic digestate for algae cultivation. in *ASABE 2018 Annual International Meeting* doi:10.13031/aim.201801333.

Wen, Y., He, Y., Ji, X., Li, S., Chen, L., Zhou, Y., et al. (2017). Isolation of an indigenous Chlorella vulgaris from swine wastewater and characterization of its nutrient removal ability in undiluted sewage. *Bioresour. Technol.* doi:10.1016/j.biortech.2017.06.094.

Whittenbury, R., Phillips, K. C., and Wilkinson, J. F. (1970). Enrichment, isolation and some properties of methane-utilizing bacteria. *J. Gen. Microbiol.* doi:10.1099/00221287-61-2-205.

Woertz, I., Feffer, A., Lundquist, T., and Nelson, Y. (2009). Algae grown on dairy and municipal wastewater for simultaneous nutrient removal and lipid production for biofuel feedstock. *J. Environ. Eng.* 135, 1115-1122.

Xia, A., and Murphy, J. D. (2016). Microalgal Cultivation in Treating Liquid Digestate from Biogas Systems. *Trends Biotechnol.* doi:10.1016/j.tibtech.2015.12.010.

Zeller, M. A., Hunt, R., Jones, A., and Sharma, S. (2013). Bioplastics and their thermoplastic blends from Spirulina and Chlorella microalgae. *J. Appl. Polym. Sci.* doi: 10.1002/app.39559.

Zou, S., Wu, Y., Yang, M., Li, C., and Tong, J. (2009). Thermochemical catalytic liquefaction of the marine microalgae Dunaliella tertiolecta and characterization of bio-oils. *Energy & Fuels* 23, 3753-3758.

EXEMPLARY EMBODIMENTS OF THE INVENTION

Embodiment 1. A system comprising: a housing comprising a top and sides and defining an inner space extending between the sides and to the top; a headspace in an upper portion of the inner space; a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space; and a surface comprising a surface portion capable of being cycled between the headspace and the reservoir.

Embodiment 2. The system of embodiment 1, wherein the housing separates the headspace from a surrounding space and the housing is capable of maintaining a gaseous composition of the headspace that is different from a gaseous composition of the surrounding space.

Embodiment 3. The system of embodiment 1, wherein the housing forms an enclosure enclosing the inner space, wherein the reservoir is entirely encompassed within the inner space.

Embodiment 4. The system of embodiment 1 wherein the reservoir further includes a second reservoir portion contiguous with the first reservoir portion, wherein the second reservoir portion does not overlap with the first reservoir portion and does not overlap with the inner space.

Embodiment 5. The system of embodiment 4, wherein the housing separates the headspace from a surrounding space and the second reservoir portion is contiguous with the surrounding space.

Embodiment 6. The system of any prior embodiment, wherein the headspace is filled with a gas and the reservoir is filled with a liquid.

Embodiment 7. The system of embodiment 6, wherein the gas comprises at least one of methane and carbon dioxide.

Embodiment 8. The system of any one of embodiments 6-7, wherein the gas comprises at least one of biogas and natural gas.

Embodiment 9. The system of any one of embodiments 6-8, wherein the liquid comprises at least one of inorganic nitrogen and inorganic phosphorus.

Embodiment 10. The system of any one of embodiments 6-9, wherein the liquid comprises wastewater.

Embodiment 11. The system of any prior embodiment, wherein the surface comprises cells adhered thereto.

Embodiment 12. The system of embodiment 11, wherein the cells comprise at least one of a methanotroph and a phototroph.

Embodiment 13. The system of embodiment 11, wherein the cells comprise a methanotroph and a phototroph.

Embodiment 14. The system of any prior embodiment, wherein the surface portion is capable of being positioned along a plane angled from 30° to 60° with respect to the horizontal plane Embodiment 15. The system of any prior embodiment, wherein the surface portion is capable of being continuously positioned along any plane angled from 30° to 60°, or any subrange thereof spanning at least 5°, with respect to the horizontal plane.

Embodiment 16. The system of any prior embodiment, wherein at least a portion of the housing is permeable to visible light.

Embodiment 17. The system of any prior embodiment, wherein the housing comprises ports in fluid connection with the inner space, wherein the fluid connection of each port is independently selected from constitutive fluid connection and regulatable fluid connection.

Embodiment 18. The system of embodiment 17, wherein at least two of the ports are in direct fluid connection with the headspace.

Embodiment 19. The system of any one of embodiments 17-18, wherein at least one of the ports is in direct fluid connection with the headspace and at least another one of the ports is in direct fluid connection with the first reservoir portion.

Embodiment 20. The system of any one of embodiments 17-19, wherein at least one of the ports is in fluid connection with another one of the ports via a channel that at least partially bypasses the inner space.

Embodiment 21. The system of any one of embodiments 17-20, wherein the ports include at least four ports.

Embodiment 22. The system of embodiment 21, wherein: a first port of the at least four ports is in fluid connection with a gas source; a second port of the at least four ports is in fluid connection with a liquid source; a third port of the at least four ports is in direct fluid connection with the headspace; and a fourth port of the at least four ports is in direct fluid connection with the first reservoir portion.

Embodiment 23. The system of embodiment 22, wherein: the gas source comprises a source of at least one of methane and carbon dioxide; and/or the liquid source comprises a source of liquid containing wastewater at least one of inorganic nitrogen and inorganic phosphorus.

Embodiment 24. The system of any one of embodiments 22-23, wherein: the gas source comprises a source of biogas; and/or the liquid source comprises a source of wastewater.

Embodiment 25. The system of any one of embodiments 22-24, wherein the gas source and the liquid source both comprise an anaerobic digester.

Embodiment 26. The system of any one of embodiments 22-25, wherein the fourth port and the second port are in fluid connection with each other via a return channel that at least partially bypasses the inner space.

Embodiment 27. The system of any prior embodiment, further comprising a retractable press capable of being reversibly positioned against the surface.

Embodiment 28. The system of any prior embodiment, further comprising a retractable scraper capable of being reversibly positioned against the surface.

Embodiment 29. The system of any prior embodiment, further comprising: a retractable press capable of being reversibly positioned against the surface; a retractable scraper capable of being reversibly positioned against the surface; and a sensor capable of sensing a condition of the surface, wherein the system is configured to position the retractable press and the retractable scraper against the surface in an automated manner when the condition is sensed by the sensor.

Embodiment 30. The system of embodiment 29, wherein the condition comprises biofilm thickness.

Embodiment 31. The system of any prior embodiment, further comprising an artificial light source directed at the surface.

Embodiment 32. The system of embodiment 31, wherein the artificial light source is powered by an energy store which is charged by a solar panel.

Embodiment 33. The system of any prior embodiment, wherein the surface is configured in the form of a continuous conveyor belt capable of being moveable along a conveyor belt path proceeding through both the headspace and the reservoir.

Embodiment 34. The system of embodiment 33, wherein at least 10% of the length of the conveyor belt path is capable of being disposed in the headspace and at least 10% of the length of the conveyor belt path is capable of being simultaneously disposed in the reservoir. Embodiment 35. The system of any one of embodiments 33-34, wherein one or more portions of the conveyor belt path are capable of being positioned within the headspace along a plane angled from 30° to 60° with respect to the horizontal plane.

Embodiment 36. The system of any one of embodiments 33-35, wherein one or more portions of the conveyor belt path are capable of being continuously positioned within the headspace along any plane angled from 30° to 60°, or any subrange thereof spanning at least 5°, with respect to the horizontal plane.

Embodiment 37. The system of any one of embodiments 33-36, wherein the conveyor belt path comprises a zigzag portion, wherein the zigzag portion includes: a first upper end disposed in the headspace; a second upper end disposed in the headspace; and at least one internal lower portion positioned in the conveyor belt path between the first upper end and the second upper end and capable of being positioned below the first upper end and the second upper end.

Embodiment 38. The system of embodiment 37, wherein the conveyor belt path further comprises a return portion at a position in the conveyor belt path opposite the zigzag portion between the first upper end of the zigzag portion and the second upper end of the zigzag portion, wherein the return portion is capable of being at least partially disposed within the reservoir.

Embodiment 39. The system of any one of embodiments 37-38, wherein the at least one internal lower portion comprises multiple internal lower portions, wherein each of the internal lower portions are separated from each other by an internal upper portion positioned within the inner space above the internal lower portions.

Embodiment 40. The system of any one of embodiments 37-39, wherein each internal lower portion is capable of being positioned within the reservoir.

Embodiment 41. The system of any one of embodiments 37-40, wherein the conveyor belt path within the zigzag portion is positioned along multiple, separate planes angled from 30° to 60° with respect to the horizontal plane.

Embodiment 42. The system of any one of embodiments 37-41, wherein the conveyor belt path within the zigzag portion is capable of being positioned along multiple, separate planes, wherein each separate plane is capable of being continuously angled from 30° to 60°, or any subrange thereof spanning at least 5°, with respect to the horizontal plane.

Embodiment 43. The system of any one of embodiments 33-42, wherein the conveyor belt is positioned along the conveyor belt path by support shafts.

Embodiment 44. The system of embodiment 43, wherein at least some of the support shafts are rotary shafts.

Embodiment 45. The system of any one of embodiments 43-44, wherein at least a subset of the support shafts comprise long axes configured in a parallel orientation with respect to each other.

Embodiment 46. The system of embodiment 45, wherein one or more of the support shafts in the subset are translationally moveable with respect to one or more other of the support shafts in the subset in a direction orthogonal to the long axes while maintaining the parallel orientation.

Embodiment 47. The system of any one of embodiments 45-46, wherein one or more of the support shafts in the subset are continuously translationally moveable with respect to one or more other of the support shafts in the subset in a direction orthogonal to the long axes while maintaining the parallel orientation.

Embodiment 48. The system of any one of embodiments 45-47, wherein translational movement of the one or more of the support shafts in the subset with respect to the one or more other of the support shafts in the subset changes an orientation of at least a portion of the surface with respect to the horizontal plane.

Embodiment 49. The system of any one of embodiments 43-48, further comprising a retractable press wheel capable of being reversibly positioned against the conveyor belt and pressing the surface against at least one of the support shafts.

Embodiment 50. The system of any one of embodiments 33-48, further comprising a retractable press wheel capable of being reversibly positioned against the conveyor belt. Embodiment 51. A method of using the system of any prior embodiment, the method comprising cultivating a cell adhered to the surface portion of the surface.

Embodiment 52. The method of embodiment 51, wherein the cell comprises a methanotroph and a phototroph.

Embodiment 53. The method of any one of embodiments 51-52, wherein the method comprises processing a gas in the headspace.

Embodiment 54. The method of embodiment 53, wherein the gas comprises at least one of methane and carbon dioxide.

Embodiment 55. The method of embodiment 54, wherein the processing comprises removing at least a portion of at least one of the methane and the carbon dioxide from the gas.

Embodiment 56. The method of anyone of embodiments 53-55, wherein the gas comprises biogas.

Embodiment 57. The method of any one of embodiments 51-56, wherein the method comprises processing a liquid in the reservoir.

Embodiment 58. The method of embodiment 57, wherein the liquid comprises wastewater.

Embodiment 59. The method of any one of embodiments 57-58, wherein the liquid comprises at least one of inorganic nitrogen and inorganic phosphorus.

Embodiment 60. The method of embodiment 59, wherein the processing comprises removing at least a portion of at least one of the inorganic nitrogen and the inorganic phosphorus from the liquid.

What is claimed is:

1. A system comprising:
a housing comprising a top and sides and defining an inner space extending between the sides and to the top;
a headspace in an upper portion of the inner space;
a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space; and
a surface comprising a surface portion capable of being cycled between the headspace and the reservoir, wherein the surface comprises cells adhered thereto, wherein the cells comprise a methanotroph and a phototroph.

2. The system of claim 1, wherein the housing separates the headspace from a surrounding space, wherein the housing is capable of maintaining a gaseous composition of the headspace that is different from a gaseous composition of the surrounding space.

3. The system of claim 1, wherein the housing forms an enclosure enclosing the inner space, wherein the reservoir is entirely encompassed within the inner space.

4. The system of claim 1 wherein the reservoir further includes a second reservoir portion contiguous with the first reservoir portion, the second reservoir portion does not overlap with the first reservoir portion and does not overlap with the inner space, the housing separates the headspace from a surrounding space, and the second reservoir portion is contiguous with the surrounding space.

5. The system of claim 1, wherein the headspace is filled with a gas, the gas comprises at least one of methane and carbon dioxide, the reservoir is filled with a liquid, and the liquid comprises at least one of inorganic nitrogen and inorganic phosphorus.

6. The system of claim 1, wherein the headspace is filled with a gas, the gas comprises at least one of biogas and natural gas, the reservoir is filled with a liquid, and the liquid comprises wastewater.

7. The system of claim 1, wherein the housing comprises ports in fluid connection with the inner space and the fluid connection of each port is independently selected from constitutive fluid connection and regulatable fluid connection.

8. The system of claim 7, wherein at least one of the ports is in fluid connection with another one of the ports via a channel that at least partially bypasses the inner space.

9. The system of claim 1, further comprising:
a retractable press capable of being reversibly positioned against the surface;
a retractable scraper capable of being reversibly positioned against the surface; and
a sensor capable of sensing a condition of the surface, wherein the system is configured to position the retractable press and the retractable scraper against the surface in an automated manner when the condition is sensed by the sensor, wherein the condition comprises biofilm thickness.

10. The system of claim 1, wherein the surface is configured in the form of a continuous conveyor belt capable of being moveable along a conveyor belt path proceeding through both the headspace and the reservoir.

11. The system of claim 10, wherein the conveyor belt path comprises a zigzag portion, wherein the zigzag portion includes:
a first upper end disposed in the headspace;
a second upper end disposed in the headspace; and
at least one internal lower portion positioned in the conveyor belt path between the first upper end and the second upper end and capable of being positioned below the first upper end and the second upper end.

12. The system of claim 11, wherein the conveyor belt path further comprises a return portion at a position in the conveyor belt path opposite the zigzag portion between the first upper end of the zigzag portion and the second upper end of the zigzag portion, wherein the return portion is capable of being at least partially disposed within the reservoir.

13. The system of claim 11, wherein each internal lower portion is capable of being positioned within the reservoir.

14. The system of claim 11, wherein the conveyor belt path within the zigzag portion is capable of being positioned along multiple, separate planes angled from 30° to 60° with respect to the horizontal plane.

15. The system of claim 11, wherein the conveyor belt path within the zigzag portion is capable of being positioned along multiple, separate planes, wherein each separate plane is capable of being continuously angled from 30° to 60°, or any subrange thereof spanning at least 5°, with respect to the horizontal plane.

16. The system of claim 10, wherein the conveyor belt is positioned along the conveyor belt path by support shafts.

17. The system of claim 16, wherein:
at least a subset of the support shafts comprise long axes configured in a parallel orientation with respect to each other;
one or more of the support shafts in the subset are translationally moveable with respect to one or more other of the support shafts in the subset in a direction orthogonal to the long axes while maintaining the parallel orientation; and
translational movement of the one or more of the support shafts in the subset with respect to the one or more other of the support shafts in the subset changes an orientation of at least a portion of the surface with respect to the horizontal plane.

18. A method of using the system of claim 1, the method comprising cultivating the cells, wherein the cells are adhered to the surface portion of the surface.

19. The method of claim 18, wherein:
the method comprises processing a gas in the headspace;
the gas comprises at least one of methane and carbon dioxide;
the processing the gas comprises removing at least a portion of at least one of the methane and the carbon dioxide from the gas;
the method comprises processing a liquid in the reservoir;
the liquid comprises at least one of inorganic nitrogen and inorganic phosphorus; and
the processing the liquid comprises removing at least a portion of at least one of the inorganic nitrogen and the inorganic phosphorus from the liquid.

20. A system comprising:
a housing comprising a top and sides and defining an inner space extending between the sides and to the top;
a headspace in an upper portion of the inner space;
a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space;

a surface comprising a surface portion capable of being cycled between the headspace and the reservoir;

a retractable press capable of being reversibly positioned against the surface;

a retractable scraper capable of being reversibly positioned against the surface; and a sensor capable of sensing a condition of the surface, wherein the system is configured to position the retractable press and the retractable scraper against the surface in an automated manner when the condition is sensed by the sensor, wherein the condition comprises biofilm thickness.

21. A system comprising:

a housing comprising a top and sides and defining an inner space extending between the sides and to the top;

a headspace in an upper portion of the inner space;

a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space; and a surface comprising a surface portion capable of being cycled between the headspace and the reservoir, wherein the surface is configured in the form of a continuous conveyor belt capable of being moveable along a conveyor belt path proceeding through both the headspace and the reservoir, wherein the conveyor belt path comprises a zigzag portion, wherein the zigzag portion includes:

a first upper end disposed in the headspace;

a second upper end disposed in the headspace; and at least one internal lower portion positioned in the conveyor belt path between the first upper end and the second upper end and capable of being positioned below the first upper end and the second upper end.

22. The system of claim 21, wherein the conveyor belt path further comprises a return portion at a position in the conveyor belt path opposite the zigzag portion between the first upper end of the zigzag portion and the second upper end of the zigzag portion, wherein the return portion is capable of being at least partially disposed within the reservoir.

23. The system of claim 21, wherein each internal lower portion is capable of being positioned within the reservoir.

24. The system of claim 21, wherein the conveyor belt path within the zigzag portion is capable of being positioned along multiple, separate planes angled from 30° to 60° with respect to the horizontal plane.

25. The system of claim 21, wherein the conveyor belt path within the zigzag portion is capable of being positioned along multiple, separate planes, wherein each separate plane is capable of being continuously angled from 30° to 60°, or any subrange thereof spanning at least 5°, with respect to the horizontal plane.

26. A system comprising:

a housing comprising a top and sides and defining an inner space extending between the sides and to the top;

a headspace in an upper portion of the inner space;

a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space; and a surface comprising a surface portion capable of being cycled between the headspace and the reservoir, wherein:

the surface is configured in the form of a continuous conveyor belt capable of being moveable along a conveyor belt path proceeding through both the headspace and the reservoir;

the conveyor belt is positioned along the conveyor belt path by support shafts;

at least a subset of the support shafts comprise long axes configured in a parallel orientation with respect to each other;

one or more of the support shafts in the subset are translationally moveable with respect to one or more other of the support shafts in the subset in a direction orthogonal to the long axes while maintaining the parallel orientation; and translational movement of the one or more of the support shafts in the subset with respect to the one or more other of the support shafts in the subset changes an orientation of at least a portion of the surface with respect to the horizontal plane.

27. A method comprising:

cultivating cells adhered to a surface portion of a system, wherein:

the cells comprise a methanotroph and a phototroph; and the system comprises:

a housing comprising a top and sides and defining an inner space extending between the sides and to the top;

a headspace in an upper portion of the inner space;

a reservoir comprising at least a first reservoir portion, wherein the first reservoir portion is in a lower portion of the inner space, the headspace and the reservoir are defined with respect to each other within the inner space by a horizontal plane spanning the inner space, and the headspace and the reservoir do not overlap within the inner space; and a surface comprising the surface portion, wherein the surface portion is capable of being cycled between the headspace and the reservoir;

processing a gas in the headspace, wherein the gas comprises at least one of methane and carbon dioxide, and wherein the processing the gas comprises removing at least a portion of at least one of the methane and the carbon dioxide from the gas; and processing a liquid in the reservoir, wherein the liquid comprises at least one of inorganic nitrogen and inorganic phosphorus, and wherein the processing the liquid comprises removing at least a portion of at least one of the inorganic nitrogen and the inorganic phosphorus from the liquid.

* * * * *